(12) United States Patent
Yoshida et al.

(10) Patent No.: US 10,603,417 B2
(45) Date of Patent: Mar. 31, 2020

(54) SYSTEM FOR EXTENDED STORAGE OF RED BLOOD CELLS AND METHODS OF USE

(71) Applicant: New Health Sciences, Inc., Bethesda, MD (US)

(72) Inventors: Tatsuro Yoshida, West Newton, MA (US); Paul Vernucci, Billerica, MA (US)

(73) Assignee: Hemanext Inc., Lexington, MA (US)

( * ) Notice: Subject to any disclaimer, the term of this patent is extended or adjusted under 35 U.S.C. 154(b) by 186 days.

(21) Appl. No.: 15/811,481

(22) Filed: Nov. 13, 2017

(65) Prior Publication Data

US 2018/0064858 A1    Mar. 8, 2018

Related U.S. Application Data

(63) Continuation of application No. 14/924,179, filed on Oct. 27, 2015, now Pat. No. 9,844,615, which is a
(Continued)

(51) Int. Cl.
*A61M 1/02* (2006.01)
*B01D 19/00* (2006.01)
*A01N 1/02* (2006.01)

(52) U.S. Cl.
CPC .......... *A61M 1/0209* (2013.01); *A01N 1/021* (2013.01); *A01N 1/0226* (2013.01);
(Continued)

(58) Field of Classification Search
CPC .... B01D 19/0031; B01D 53/22; B01D 63/02; B01D 2257/104; B01D 2257/504; A61M 1/0209; A61M 1/0231; A61M 1/0272; A61M 1/36; A61M 2205/0205; A61M 2205/0225
See application file for complete search history.

(56) References Cited

U.S. PATENT DOCUMENTS 3,064,647 A    11/1962  Earl
3,361,041 A     1/1968  Grob
(Continued)

FOREIGN PATENT DOCUMENTS

AU    2012279043    7/2016
CA     2477946      9/2003
(Continued)

OTHER PUBLICATIONS

U.S. Appl. No. 10/295,781, filed Nov. 15, 2002, Bitensky et al.
(Continued)

*Primary Examiner* — Jason M Greene
(74) *Attorney, Agent, or Firm* — Arnold & Porter Kaye Scholar LLP

(57) ABSTRACT

A system and methodology for the preservation of red blood cells is described in which red blood cells are oxygen or oxygen and carbon dioxide depleted, treated and are stored in an anaerobic environment to optimize preparation for transfusion. More particularly, a system and method for extended storage of red blood cells from collection to transfusion that optimizes red blood cells prior to transfusion is described.

20 Claims, 27 Drawing Sheets

Related U.S. Application Data continuation of application No. 13/541,554, filed on Jul. 3, 2012, now Pat. No. 9,199,016, which is a continuation-in-part of application No. 12/901,350, filed on Oct. 8, 2010, now Pat. No. 8,535,421, which is a continuation-in-part of application No. 13/289,722, filed on Nov. 4, 2011, now Pat. No. 10,136,635, and a continuation-in-part of application No. 13/115,532, filed on May 25, 2011, now Pat. No. 8,569,052, which is a continuation of application No. 12/903,057, filed on Oct. 12, 2010, now abandoned.

(60) Provisional application No. 61/504,640, filed on Jul. 5, 2011, provisional application No. 61/504,644, filed on Jul. 5, 2011, provisional application No. 61/410,684, filed on Nov. 5, 2010, provisional application No. 61/331,693, filed on May 5, 2010, provisional application No. 61/250,661, filed on Oct. 12, 2009.

(52) U.S. Cl.
CPC ......... *A01N 1/0263* (2013.01); *A01N 1/0294* (2013.01); *A61M 1/0231* (2014.02); *A61M 1/0272* (2013.01); *B01D 19/0031* (2013.01); *A61M 2202/0208* (2013.01); *A61M 2202/0225* (2013.01)

(56) References Cited

U.S. PATENT DOCUMENTS

| | | |
|---|---|---|
| 3,668,837 A | 6/1972 | Gross |
| 3,668,838 A | 6/1972 | McNeil et al. |
| 3,803,810 A | 4/1974 | Rosenberg |
| 3,910,841 A | 10/1975 | Esmond |
| 3,942,529 A | 3/1976 | Waage |
| 4,075,091 A | 2/1978 | Bellhouse |
| 4,086,924 A | 5/1978 | Latham, Jr. |
| 4,093,515 A | 6/1978 | Kolobow |
| 4,131,200 A | 12/1978 | Rinfret |
| 4,162,676 A | 7/1979 | Talcott |
| 4,222,379 A | 9/1980 | Smith |
| 4,225,439 A | 9/1980 | Spranger |
| 4,228,032 A | 10/1980 | Talcott |
| 4,253,458 A | 3/1981 | Bacehowski et al. |
| 4,256,692 A | 3/1981 | Cover |
| 4,262,581 A | 4/1981 | Ferrell |
| 4,300,559 A | 11/1981 | Gajewski et al. |
| 4,314,480 A | 2/1982 | Becker |
| 4,342,723 A | 8/1982 | Sado et al. |
| 4,366,179 A | 12/1982 | Nawata et al. |
| 4,370,160 A | 1/1983 | Ziemelis |
| 4,381,775 A | 5/1983 | Nose' et al. |
| 4,386,069 A | 5/1983 | Estep |
| 4,398,642 A | 8/1983 | Okudaira et al. |
| 4,440,815 A | 4/1984 | Zomorodi et al. |
| 4,455,299 A | 6/1984 | Grode |
| 4,540,416 A | 9/1985 | Hattori et al. |
| 4,568,328 A | 2/1986 | King et al. |
| 4,572,899 A | 2/1986 | Walker et al. |
| 4,579,223 A | 4/1986 | Otsuka et al. |
| 4,585,735 A | 4/1986 | Meryman et al. |
| 4,629,544 A | 12/1986 | Bonaventura et al. |
| 4,639,353 A | 1/1987 | Takemura et al. |
| 4,654,053 A | 3/1987 | Sievers et al. |
| 4,659,549 A | 4/1987 | Hamada et al. |
| 4,670,013 A | 6/1987 | Barnes et al. |
| 4,701,267 A | 10/1987 | Watanabe et al. |
| 4,713,176 A | 12/1987 | Schoendorfer et al. |
| 4,731,978 A | 5/1988 | Martensson |
| 4,748,121 A | 5/1988 | Beaver et al. |
| 4,749,551 A | 6/1988 | Borgione |
| 4,769,175 A | 9/1988 | Inoue |
| 4,769,318 A | 9/1988 | Hamasaki et al. |
| 4,798,728 A | 1/1989 | Sugisawa |
| 4,837,047 A | 6/1989 | Sato et al. |
| 4,859,360 A | 8/1989 | Suzuki et al. |
| 4,861,867 A | 8/1989 | Estep |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 4,986,837 A | 1/1991 | Shibata |
| 4,998,990 A | 3/1991 | Richter et al. |
| 5,000,848 A | 3/1991 | Hodgins et al. |
| 5,023,054 A | 6/1991 | Sato et al. |
| 5,037,419 A | 8/1991 | Valentine et al. |
| 5,120,659 A | 6/1992 | King et al. |
| 5,137,531 A | 8/1992 | Lee et al. |
| 5,139,668 A | 8/1992 | Pan et al. |
| 5,143,763 A | 9/1992 | Yamada et al. |
| 5,152,905 A | 10/1992 | Pall et al. |
| 5,192,320 A | 3/1993 | Anazawa et al. |
| 5,194,158 A | 3/1993 | Matson |
| 5,208,335 A | 5/1993 | Ramprasad et al. |
| 5,229,012 A | 7/1993 | Pall et al. |
| 5,254,248 A | 10/1993 | Nakamura et al. |
| 5,286,407 A | 2/1994 | Inoue et al. |
| 5,328,268 A | 7/1994 | LaFleur |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,368,808 A | 11/1994 | Koike et al. |
| 5,382,526 A | 1/1995 | Gajewski et al. |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,449,617 A | 9/1995 | Falkenberg et al. |
| 5,476,764 A | 12/1995 | Bitensky |
| 5,506,141 A | 4/1996 | Weinreb et al. |
| 5,529,821 A | 6/1996 | Ishikawa et al. |
| 5,605,934 A | 2/1997 | Giertych |
| 5,617,873 A | 4/1997 | Yost et al. |
| 5,624,794 A | 4/1997 | Bitensky et al. |
| 5,635,358 A | 6/1997 | Wilding et al. |
| 5,686,304 A | 11/1997 | Codner |
| 5,691,452 A | 11/1997 | Gawryl et al. |
| 5,693,122 A | 12/1997 | Berndt |
| 5,693,230 A | 12/1997 | Asher |
| 5,698,250 A | 12/1997 | DelDuca et al. |
| 5,709,472 A | 1/1998 | Prusik et al. |
| 5,744,056 A | 4/1998 | Venkateshwaran et al. |
| 5,730,989 A | 5/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,789,152 A | 8/1998 | Black et al. |
| 5,811,142 A | 9/1998 | DelDuca et al. |
| 5,846,427 A | 12/1998 | Kessler et al. |
| 5,858,015 A | 1/1999 | Fini |
| 5,858,643 A | 1/1999 | Ben-Hur et al. |
| 5,863,460 A | 1/1999 | Slovacek et al. |
| 5,895,810 A | 4/1999 | Light et al. |
| 5,902,747 A | 5/1999 | Nemser et al. |
| 5,906,285 A | 5/1999 | Slat |
| 5,955,519 A | 9/1999 | Neri |
| 5,962,650 A | 10/1999 | Osterberg et al. |
| 5,972,710 A | 10/1999 | Weigl et al. |
| 6,007,529 A | 12/1999 | Gustafsson et al. |
| 6,027,623 A | 2/2000 | Ohkawa |
| 6,042,264 A | 3/2000 | Prusik et al. |
| 6,045,701 A | 4/2000 | Ung-Chhun et al. |
| 6,047,203 A | 4/2000 | Sackner et al. |
| 6,076,664 A | 6/2000 | Yeager |
| 6,080,322 A | 6/2000 | Deniega et al. |
| 6,090,062 A | 7/2000 | Sood et al. |
| 6,097,293 A | 8/2000 | Galloway et al. |
| 6,148,536 A | 11/2000 | Iijima |

(56) References Cited

U.S. PATENT DOCUMENTS

| | | | |
|---|---|---|---|
| 6,150,085 A | 11/2000 | Hess et al. | |
| 6,156,231 A | 12/2000 | McKedy | |
| 6,162,396 A * | 12/2000 | Bitensky | A61M 1/0209 422/44 |
| 6,164,821 A | 12/2000 | Randall | |
| 6,187,572 B1 | 2/2001 | Platz et al. | |
| 6,210,601 B1 | 4/2001 | Hottle et al. | |
| 6,231,770 B1 | 5/2001 | Bormann et al. | |
| 6,248,690 B1 | 6/2001 | McKedy | |
| 6,254,628 B1 | 7/2001 | Wallace et al. | |
| 6,287,284 B1 | 9/2001 | Woarburton-Pitt | |
| 6,315,815 B1 | 11/2001 | Spadaccini | |
| 6,337,026 B1 | 1/2002 | Lee et al. | |
| 6,358,678 B1 | 3/2002 | Bakaltcheva et al. | |
| 6,368,871 B1 | 4/2002 | Christel et al. | |
| 6,387,461 B1 | 5/2002 | Ebner et al. | |
| 6,402,818 B1 | 6/2002 | Sengupta et al. | |
| 6,403,124 B1 | 6/2002 | Dottori | |
| 6,413,713 B1 | 7/2002 | Serebrennikov | |
| 6,436,872 B2 | 8/2002 | McKedy | |
| 6,439,577 B2 | 8/2002 | Jorgensen et al. | |
| 6,447,987 B1 | 9/2002 | Hess et al. | |
| 6,468,732 B1 | 10/2002 | Malin et al. | |
| 6,475,147 B1 | 11/2002 | Yost et al. | |
| 6,482,585 B2 | 11/2002 | Dottori | |
| 6,494,909 B2 | 12/2002 | Greenhalgh | |
| 6,527,957 B1 | 3/2003 | Denienga et al. | |
| 6,558,571 B1 | 5/2003 | Powers | |
| 6,564,207 B1 | 5/2003 | Abdoh | |
| 6,582,496 B1 | 6/2003 | Cheng et al. | |
| 6,610,772 B1 | 8/2003 | Clauberg et al. | |
| 6,626,884 B1 | 9/2003 | Dillon et al. | |
| 6,688,476 B2 | 2/2004 | Breillatt, Jr. et al. | |
| 6,695,803 B1 | 2/2004 | Robinson et al. | |
| 6,697,667 B1 | 2/2004 | Lee et al. | |
| 6,709,492 B1 | 3/2004 | Spadaccini | |
| 6,723,051 B2 | 4/2004 | Davidson et al. | |
| 6,761,695 B2 | 7/2004 | Yost et al. | |
| 6,773,407 B2 | 8/2004 | Yost et al. | |
| 6,808,675 B1 | 10/2004 | Coelho et al. | |
| 6,817,979 B2 | 11/2004 | Nihtilä | |
| 6,866,783 B2 | 3/2005 | Baurmeister et al. | |
| 6,878,335 B2 | 4/2005 | Britten et al. | |
| 6,899,822 B2 | 5/2005 | McKedy | |
| 6,955,648 B2 | 10/2005 | Mozayeni et al. | |
| 6,977,105 B1 | 12/2005 | Fujieda et al. | |
| 7,041,800 B1 | 5/2006 | Gawryl et al. | |
| 7,097,690 B2 | 8/2006 | Usher et al. | |
| 7,104,958 B2 | 9/2006 | Crutchfield et al. | |
| 7,125,498 B2 | 10/2006 | McKedy | |
| 7,208,120 B2 | 4/2007 | Bitensky et al. | |
| 7,347,887 B2 | 3/2008 | Bulow et al. | |
| 7,361,277 B2 | 4/2008 | Bormann et al. | |
| 7,431,995 B2 | 10/2008 | Smith et al. | |
| 7,452,601 B2 | 11/2008 | Ebner et al. | |
| 7,517,146 B2 | 4/2009 | Smith et al. | |
| 7,666,486 B2 | 2/2010 | Sato et al. | |
| 7,713,614 B2 | 5/2010 | Chow et al. | |
| 7,721,898 B2 | 5/2010 | Yagi et al. | |
| 7,723,017 B2 | 5/2010 | Bitensky et al. | |
| 7,754,798 B2 | 7/2010 | Ebner et al. | |
| 7,763,097 B2 | 7/2010 | Federspiel | |
| 7,775,376 B2 | 8/2010 | Bonaguidi et al. | |
| 7,784,619 B2 | 8/2010 | Jacobson | |
| 8,070,664 B2 | 12/2011 | Rochat | |
| 8,071,282 B2 | 12/2011 | Bitensky et al. | |
| 8,535,421 B2 | 9/2013 | Yoshida et al. | |
| 8,569,052 B2 | 10/2013 | Federspiel et al. | |
| 8,864,735 B2 | 10/2014 | Sano et al. | |
| 8,887,721 B2 | 11/2014 | Zapol et al. | |
| 9,005,343 B2 | 4/2015 | Yoshida et al. | |
| 9,067,004 B2 | 6/2015 | Yoshida et al. | |
| 9,199,016 B2 | 12/2015 | Yoshida et al. | |
| 9,296,990 B2 | 3/2016 | Federspiel et al. | |
| 9,539,375 B2 | 1/2017 | Yoshida et al. | |
| 9,801,784 B2 | 10/2017 | Yoshida et al. | |
| 9,844,615 B2 * | 12/2017 | Yoshida | A61M 1/0209 |
| 2001/0027156 A1 | 10/2001 | Egozy et al. | |
| 2001/0037078 A1 | 11/2001 | Lynn et al. | |
| 2001/0049089 A1 | 12/2001 | Dottori | |
| 2002/0062078 A1 | 5/2002 | Crutchfield et al. | |
| 2002/0066699 A1 | 6/2002 | Boggs et al. | |
| 2002/0085952 A1 | 7/2002 | Ellingboe et al. | |
| 2002/0086329 A1 | 7/2002 | Shvets et al. | |
| 2002/0099570 A1 | 7/2002 | Knight | |
| 2002/0176798 A1 | 11/2002 | Linker et al. | |
| 2002/0182241 A1 | 12/2002 | Borenstein et al. | |
| 2003/0003575 A1 | 1/2003 | Vacanti et al. | |
| 2003/0039582 A1 | 2/2003 | Chambers et al. | |
| 2003/0040835 A1 | 2/2003 | Ng et al. | |
| 2003/0062299 A1 | 4/2003 | Lee et al. | |
| 2003/0106861 A1 | 6/2003 | Gibbs et al. | |
| 2003/0124504 A1 | 7/2003 | Bitensky et al. | |
| 2003/0153074 A1 | 8/2003 | Bitensky et al. | |
| 2003/0183801 A1 | 10/2003 | Yang et al. | |
| 2003/0189003 A1 | 10/2003 | Kraus et al. | |
| 2003/0190272 A1 | 10/2003 | Raine et al. | |
| 2003/0201160 A1 | 10/2003 | Goodrich et al. | |
| 2003/0215784 A1 | 11/2003 | Dumont et al. | |
| 2003/0233934 A1 | 12/2003 | Wijmans et al. | |
| 2004/0013566 A1 | 1/2004 | Myrick et al. | |
| 2004/0026341 A1 | 2/2004 | Hogberg et al. | |
| 2004/0097862 A1 | 5/2004 | Lampeter et al. | |
| 2004/0126880 A1 | 7/2004 | Manders et al. | |
| 2004/0168982 A1 | 9/2004 | Bitensky et al. | |
| 2004/0254560 A1 | 12/2004 | Coelho et al. | |
| 2005/0038342 A1 | 2/2005 | Mozayeni et al. | |
| 2005/0085785 A1 | 4/2005 | Shang et al. | |
| 2005/0137517 A1 | 6/2005 | Blickhan et al. | |
| 2005/0139806 A1 | 6/2005 | Havens et al. | |
| 2005/0208462 A1 | 9/2005 | Bitensky et al. | |
| 2005/0210141 A1 | 9/2005 | Oyama et al. | |
| 2005/0230856 A1 | 10/2005 | Parekh et al. | |
| 2005/0233302 A1 | 10/2005 | Hess et al. | |
| 2006/0081524 A1 | 4/2006 | Sengupta et al. | |
| 2006/0118479 A1 | 6/2006 | Shevkoplyas et al. | |
| 2006/0160724 A1 | 7/2006 | Gawryl et al. | |
| 2006/0169138 A1 | 8/2006 | Schmidt | |
| 2006/0226087 A1 | 10/2006 | Robinson et al. | |
| 2006/0278073 A1 | 12/2006 | McHugh | |
| 2007/0078113 A1 | 4/2007 | Roth et al. | |
| 2007/0099170 A1 | 5/2007 | Goodrich et al. | |
| 2007/0240569 A1 | 10/2007 | Ooya | |
| 2007/0276508 A1 | 11/2007 | Fischer et al. | |
| 2008/0027368 A1 | 1/2008 | Kollar et al. | |
| 2008/0098894 A1 | 5/2008 | Sabatino | |
| 2008/0160107 A1 | 7/2008 | McCaney et al. | |
| 2008/0234327 A1 * | 9/2008 | Cadieux | C07D 401/12 514/338 |
| 2008/0243045 A1 | 10/2008 | Pasqualini | |
| 2008/0276803 A1 | 11/2008 | Molaison et al. | |
| 2009/0017128 A1 | 1/2009 | Monzyk et al. | |
| 2009/0084720 A1 | 4/2009 | Dannenmaier et al. | |
| 2009/0235619 A1 | 9/2009 | Ostler et al. | |
| 2009/0269837 A1 | 10/2009 | Shevkoplyas et al. | |
| 2010/0021879 A1 | 1/2010 | Delgado et al. | |
| 2010/0133203 A1 | 6/2010 | Walker et al. | |
| 2010/0221697 A1 | 9/2010 | Sehgal | |
| 2010/0282662 A1 | 11/2010 | Lee et al. | |
| 2010/0294128 A1 | 11/2010 | Schmidt | |
| 2010/0313755 A1 | 12/2010 | Koros et al. | |
| 2010/0331767 A1 | 12/2010 | Frankowski | |
| 2011/0092875 A1 | 4/2011 | Beck | |
| 2012/0024156 A1 | 2/2012 | Yoshida et al. | |
| 2012/0077182 A1 | 3/2012 | Bitensky et al. | |
| 2012/0100523 A1 | 4/2012 | Federspiel et al. | |
| 2012/0115124 A1 | 5/2012 | Yoshida et al. | |
| 2012/0129148 A1 | 5/2012 | Hess et al. | |
| 2012/0129149 A1 | 5/2012 | Federspiel et al. | |
| 2012/0146266 A1 | 6/2012 | Oda et al. | |
| 2012/0219633 A1 | 8/2012 | Sowemimo-Coker | |
| 2013/0004937 A1 | 1/2013 | Yoshida et al. | |
| 2013/0144266 A1 | 6/2013 | Borenstein et al. | |
| 2013/0197420 A1 | 8/2013 | Fissell, IV et al. | |

(56) References Cited

U.S. PATENT DOCUMENTS

| | | |
|---|---|---|
| 2013/0259744 A1 | 10/2013 | Yoshida et al. |
| 2013/0327677 A1 | 12/2013 | McDorman |
| 2014/0012185 A1 | 1/2014 | Ishizuka et al. |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2015/0306288 A1 | 10/2015 | Delorme et al. |
| 2016/0007588 A1 | 1/2016 | Levesque et al. |
| 2016/0242410 A9 | 8/2016 | Yoshida et al. |

FOREIGN PATENT DOCUMENTS

| | | |
|---|---|---|
| CN | 1195965 A | 10/1998 |
| CN | 2502700 Y | 7/2002 |
| CN | 1642628 A | 7/2005 |
| CN | 2780207 Y | 5/2006 |
| CN | 2894710 Y | 5/2007 |
| CN | 101039737 A | 9/2007 |
| CN | 103732056 | 4/2014 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1109447 | 10/2003 |
| EP | 1 891 999 A1 | 2/2008 |
| EP | 2389064 | 11/2011 |
| EP | 2635114 | 9/2013 |
| EP | 2459247 A2 | 3/2016 |
| EP | 3 285 711 A1 | 10/2016 |
| EP | 3 268 015 A1 | 1/2018 |
| FR | 2 581 289 A1 | 11/1986 |
| FR | 2 996 413 A1 | 4/2014 |
| GB | 1 044 649 A2 | 10/1966 |
| GB | 2283015 A1 | 4/1995 |
| JP | 58-194879 | 11/1983 |
| JP | 59-115349 | 7/1984 |
| JP | 61-109577 A | 5/1986 |
| JP | 63-63616 A | 3/1988 |
| JP | 01-104271 A | 4/1989 |
| JP | 3-284263 | 12/1991 |
| JP | 5-503075 A | 5/1993 |
| JP | 5-503304 A | 6/1993 |
| JP | H05-148151 A | 6/1993 |
| JP | 5-305123 A | 11/1993 |
| JP | H05-317413 | 12/1993 |
| JP | 06-121920 A | 5/1994 |
| JP | 2668446 | 7/1997 |
| JP | 2700170 B2 | 1/1998 |
| JP | 10-501443 A | 2/1998 |
| JP | H10-507395 | 7/1998 |
| JP | 11-216179 | 8/1999 |
| JP | 2000-516963 A | 12/2000 |
| JP | 2001-500053 | 1/2001 |
| JP | 2001-523225 | 11/2001 |
| JP | 2002-087971 | 3/2002 |
| JP | 2002-253936 A | 9/2002 |
| JP | 2002-541941 | 12/2002 |
| JP | 2004-089495 A | 3/2004 |
| JP | 2005-533041 A | 11/2005 |
| JP | 2005-535279 A | 11/2005 |
| JP | 2005-535289 A | 11/2005 |
| JP | 2006-502078 A | 1/2006 |
| JP | 2006-515279 | 5/2006 |
| JP | 2006-213923 | 8/2006 |
| JP | 2007-260393 A | 10/2007 |
| JP | 2008-86996 | 4/2008 |
| JP | 2008-528066 | 7/2008 |
| JP | 2008-529550 A | 8/2008 |
| JP | 2008-253452 | 10/2008 |
| JP | 2009-513235 | 4/2009 |
| JP | 10/501443 | 2/2010 |
| JP | 2010-503501 A | 2/2010 |
| JP | 2010-509353 | 3/2010 |
| JP | 2010-116626 | 5/2010 |
| JP | 2010-538735 | 12/2010 |
| JP | 2011-92905 | 5/2011 |
| JP | 2013-500794 | 1/2013 |
| JP | 2014-518283 | 7/2014 |
| JP | 2014-527436 | 10/2014 |
| JP | 2007-509206 A | 4/2017 |
| KR | 10-0721054 | 5/2006 |
| SU | 1718766 A1 | 1/1990 |
| WO | WO 1981/02239 A1 | 8/1981 |
| WO | WO 1986/00809 A1 | 2/1986 |
| WO | WO 1989/02274 A1 | 3/1989 |
| WO | WO 1991/04659 A1 | 4/1991 |
| WO | WO 1992/08348 A1 | 5/1992 |
| WO | WO 1995/29662 A2 | 11/1995 |
| WO | WO 1996/29103 A1 | 9/1996 |
| WO | WO 1996/29346 A1 | 9/1996 |
| WO | WO 1996/29864 A1 | 10/1996 |
| WO | WO 1996/39026 A1 | 12/1996 |
| WO | WO 1997/37628 A1 | 10/1997 |
| WO | WO 1998/046073 A1 | 10/1998 |
| WO | WO 1998/51147 A1 | 11/1998 |
| WO | WO 1999/25726 A1 | 5/1999 |
| WO | WO 1999/29346 A1 | 6/1999 |
| WO | WO 1999/48963 A2 | 9/1999 |
| WO | WO 2000/011946 A2 | 3/2000 |
| WO | WO 2000/0062891 | 10/2000 |
| WO | WO 2003/043419 A1 | 5/2003 |
| WO | WO 2003/043571 A2 | 5/2003 |
| WO | WO 2003/086577 A1 | 10/2003 |
| WO | WO 03/103390 A1 | 12/2003 |
| WO | WO 2004/043381 A2 | 5/2004 |
| WO | WO 2006/057473 A1 | 6/2006 |
| WO | WO 2006/088455 A1 | 8/2006 |
| WO | WO 2008/063868 | 5/2008 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 A1 | 4/2011 |
| WO | WO 2011/068897 A1 | 6/2011 |
| WO | WO 2012/027582 A1 | 3/2012 |
| WO | WO 2012/061731 A1 | 5/2012 |
| WO | WO 2012/120927 A1 | 9/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/043658 A1 | 3/2013 |
| WO | WO 2013/153441 A1 | 10/2013 |
| WO | WO 2013/177339 A1 | 11/2013 |
| WO | WO 2014/134503 A1 | 9/2014 |
| WO | WO 2014/194931 A1 | 12/2014 |
| WO | WO 2016/145210 A1 | 9/2016 |
| WO | WO 2016/172645 A1 | 10/2016 |

OTHER PUBLICATIONS

U.S. Appl. No. 62/131,130, filed Mar. 15, 2015, Wolf et al.
U.S. Appl. No. 62/151,957, filed Apr. 23, 2015, Yoshida et al.
U.S. Appl. No. 12/901,350, filed Oct. 8, 2010, Yoshida et al.
Alcantar et al., "Polyethylene glycol-coated biocompatible surfaces," *Journal of Biomedical Materials Research*, 51(3):343-351 (2000).
Anderson et al., "Microfabrication and microfluidics for tissue engineering: state of the art and future opportunities," *Lab Chip*, 4:98-103 (2004).
Barbee et al., "The Fahraeus Effect," *Microvascular Research*, 3:6-16 (1971).
Barclay et al., "A Method for Detecting Chaos in Canine Myocardial Microcirculatory Red Cell Flux," *Microcirculation*, 7(5):335-346 (2000).
Bardy et al., "Technetium-99m Labeling by Means of Stannous Pyrophosphate: Application to Bleomycin and Red Blood Cells," *Journal of Nuclear Medicine*, 16(5):435-437 (1975).
Barras et al., "Influence of Rejuvenation on the Rheological Properties of Stored Erythrocytes," *VASA*, 23(4):305-311 (1994).

(56) References Cited

OTHER PUBLICATIONS

Bensinger et al., "Prolonged maintenance of 2,3-DPG in liquid blood storage: Use of an internal CO.sub.2 trap to stabilize pH," *J. Lab. Clin. Med.*, 89(3):498-503 (1977).
Benson et al., "Accumulation of Pro-Cancer Cytokines in the Plasma Fraction of Stored Packed Red Cells," *J Gastrointest Surg.*, 16:460-468 (2012).
Beutler et al., "Storage of red cell concentrates in CPD-A2 for 42 and 49 days," *The Journal of Laboratory and Clinical Medicine*, 102(1):53-62 (1983).
Borenstein et al., "Microfabrication Technology for Vascularized Tissue Engineering," *Biomedical Microdevices*, 4(3):167-175 (2002).
Brody et al., "Deformation and Flow of Red Blood Cells in a Synthetic Lattice: Evidence for an Active Cytoskeleton," *Biophysical Journal*, 68:2224-2232 (1995).
Burns et al., "Artificial microvascular network: a new tool for measuring rheologic properties of stored red blood cells," Transfusion, 52(5):1010-1023 (2012).
Buskirk et al., "Accumulation of Biologic Response Modifiers During Red Blood Cell Cold Storage," *Transfusion*, 49(Suppl3): 102A-103A (2009).
Carmen, "The Selection of Plastic Materials for Blood Bags," *Transfusion Medicine Reviews*, 7(1):1-10 (1993).
Carr et al., "Nonlinear Dynamics of Microvascular Blood Flow," *Annals of Biomedical Engineering*, 28:641-652 (2000).
Cell Deformability, RheoSCAN (RheoScan-AnD300/RheoScan-D300), obtained on Dec. 11, 2012, from: http://www.rheoscan.com/products/products/products-01.html.
Chaplin et al., "The Proper Use of Previously Frozen Blood Cells for Transfusion," *Blood*, 59:1118-1120 (1982).
Chilton et al., "Privacy Protection of Health Information: Patient Rights and Pediatrician Responsibilities," *Pediatrics*, 104(4):973-977 (1999).
Cognasse et al., "The role of microparticles in inflammation and transfusion: A concise review," *Transfus. Apher. Sci.* 53(2):159-167 (2015).
Cokelet et al., "Fabrication of in Vitro Microvascular Blood Flow Systems by Photolithography," *Microvascular Research*, 46:394-400 (1993).
Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).
De Angelis et al., "Erythrocyte Shape Control in Stored Blood: The Effect of Additive Solutions on Shape Recovery," *Haematologica*, 73:7-12 (1988).
Deible et al., "Molecular barriers to biomaterial thrombosis by modification of surface proteins with polyethylene glycol," *Biomaterials*, 19:1885-1893 (1998).
De Korte et al., "Prolonged maintenance of 2,3-diphosphoglycerate acid and adenosine triphosphate in red blood cells during storage," *Transfusion*, 48:1081-1089 (2008).
De Venuto et al., "Rejuvenation of Human Red Blood Cells During Liquid Storage," *Transfusion*, 14(4):338-344 (1974).
Dumaswala et al., "Studies in Red Blood Cell Preservation: 9. The Role of Glutamine in Red Cell Preservation," *Vox Sang*, 67:255-259 (1994).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumont et al., "Anaerobic storage of red blood cells in a novel additive solution improves in vivo recovery," *Transfusion*, 49(3):458-464 (2009).
Dumont et al., "$CO_2$-dependent metabolic modulation in red cells stored under anaerobic conditions," *Transfusion* 56(2): 392-403 (2016)(epub 2015).

Durapore® Membrane Filters—Filter Discs and Membranes, retrieved on Aug. 26, 2014, from: www.emdmillipore.com/US/en/product/Durapore.
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
European Search Report completed on Feb. 11, 2005, in European Patent Application No. 02 78 2307.9.
Extended European Search Report, dated Aug. 29, 2014 for European Patent Application No. 10823965.8.
Extended European Search Report dated Oct. 30, 2014 in European Patent Application No. 11838889.1.
Extended European Search Report dated Oct. 24, 2014 in European Patent Application No. 12807324.4.
Extended European Search Report dated Mar. 5, 2015, in European Patent Application No. 12821624.9.
Extended European Search Report dated Jun. 15, 2015, in European Patent Application No. 11820660.6.
Fahraeus et al., "The Viscosity of the Blood in Narrow Capillary Tubes," *Am. J. Physiol.*, 96(3):562-568 (1931).
Fage et al., "On transition from laminar to turbulent flow in the boundary layer," The gamma-ray transition of radio-bromine, *Proceedings of the Royal Society*, 178(973):205-227 (1940).
Fang et al., "Inhibition of Lipopolysaccharide-Associated Endotoxin Activities In Vitro and In Vivo by the Human Anti-Lipid A Monoclonal Antibody SdJ5—Jan. 17, 2015," *Infection and Immunity*, 61(9):3873-3878 (1993).
Fatouros et al., "Recombinant factor VII SQ—influence of oxygen, metal ions, pH and ionic strength on its stability in aqueous solution," *International Journal of Pharmaceutics*, 155(1):121-131 (1997).
Frame et al., "A System for Culture of Endothelial Cells in 20-50-µm Branching Tubes," *Microcirculation*, 2(4):377-385 (1995).
"Friction Factor for Flow in Coils and Curved Pipe," Neutrium Available on the world wide web at neutrium.net/fluid_flow/friction-factor-for-flow-in-coils-and-curved-pipe/. (2017).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gifford et al, "Parallel Microchannel-Based Measurements of Individual Erythrocyte Areas and Volumes," *Biophysical Journal*, 84:623-633 (2003).
Gifford et al, "A detailed study of time-dependent changes in human red blood cells: from reticulocyte maturation to erythrocyte senescence," *British Journal of Haematology*, 135:395-404 (2006).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Hamasaki et al., "Acid-citrate-dextrose-phosphoenolpyruvate medium as a rejuvenant for blood storage," *Transfusion*, 23(1):1-7 (1983).
Heaton et al., "Use of Adsol preservation solution for prolonged storage of low viscosity AS-1 red blood cells," *Br J. Haematol*, 57(3):467-478 (1984).

(56) References Cited

OTHER PUBLICATIONS

Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al., "Effects of Oxygen on Red Cells during Liquid Storage at +4° C.," *Vox Sang.*, 51:27-34 (1986).
Högman et al., "Effects of oxygen and mixing on red cells stored in plastic bags at +4° C.," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Högman, "Preparation and Preservation of Red Cells," *Vox Sanguinis* 74(Suppl. 2):177-187 (1998).
Holme et al., "Current Issues Related to the Quality of Stored RBCs," *Transfusion and Apheresis Science*, 33(1):55-61 (2005).
Huang et al., "Continuous Particle Separation Through Deterministic Lateral Displacement," *Science*, 304:987-990 (2004).
International Committee for Standardization in Hematology, "Recommended Methods for Radioisotope Red Cell Survival Studies," *Blood* 38(3):378-386 (1971).
International Preliminary Report on Patentability dated Feb. 18, 2011 (completed on Feb. 8, 2012), in International Patent Application No. PCT/US2010/52084.
International Preliminary Report on Patentability dated May 24, 2012 (completed on May 21, 2012), in International Patent Application No. PCT/US2010/52376.
International Search Report Completed on Feb. 8, 2011, in International Patent Application No. PCT/US10/52084.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report and Written Opinion dated Dec. 6, 2010 for corresponding International Patent Application No. PCT/US2010/052376.
International Search Report dated Apr. 27, 2011(completed on Apr. 26, 2011), in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report and Written Opinion issued in International Application PCT/US2014/019537 dated Jul. 10, 2014.
International Search Report completed on Nov. 9, 2012 issued in International Patent Application No. PCT/US12/045426 (dated Nov. 26, 2012).
International Search Report for PCT/US2016/021794 dated Jul. 18, 2016.
Irsch et al., "Pathogen inactivation of platelet and plasma blood components for transfusion using the INTERCEPT Blood System™," *Transfusion Medicine and Hemotherapy*, 38:19-31 (2011).
Jain, et al., "Determinants of Leukocyte Margination in Rectangular Microchannels," *PLoS ONE*, 4(9):1-8 (2009).
Jarus et al., "Barrier Properties of polypropylene/polyamide blends produced by microlayer coextrusion," *Polymer* 43:2401-2408 (2002).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micromachining to Tissue Engineer Branched Vascular Channels for Liver Fabrication," *Tissue Engineering*, 6(2):105-117 (2000).
Kaiser-Guignard et al., "The clinical and biological impact of new pathogen inactivation technologies on platelet concentrates," *Blood Reviews* 28:235-241 (2014).
Kakaiya et al., "Platelet preservation in large containers," *Vox Sanguinis*, 46(2):111-118 (1984).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Kilkson et al., "Platelet metabolism during storage of platelet concentrates at 22° C.," *Blood* 64(2):406-414 (1984).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Kynar Flex Product Catalog, downloaded May 20, 2015 from Kynar.com.
Lowndes, "Blood Interference in fluorescence spectrum: Experiment, analysis and comparison with intraoperative measurements on brain tumor," *Bachelor Thesis*, Linköping University, pp. 1-42 (2010).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Lundblad, "Factor VIII—Reducing agents, copper ions, and stability," http://lundbladbiotech.com.
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C.," *Transfusion*, 26(6):500-505 (1986).
Meryman et al., "Extending the storage of red cells at 4° C.," *Transfus. Sci.*, 15(2):105-115 (1994).

(56) References Cited

OTHER PUBLICATIONS

Moll et al., "Dean vortices applied to membrane process. Part II: Numerical approach," *Journal of Membrane Science*, 288:321-335 (2007).
Moroff et al., "Factors Influencing Changes in pH during Storage of Platelet Concentrates at 20-24° C.," *Vox Sanguinis*, 42(1):33-45 (1982).
Moroff et al., "Proposed standardization of methods for determining the 24-hour survival of stored red cells," *Transfusion*, 24:109-114 (1984).
Moroff et al., "Concepts about current conditions for the preparation and storage of platelets," *Transfus Med Rev* V(1):48-59 (1991).
Murphy et al., "Platelet storage at 22° C.: role of gas transport across plastic containers in maintenance of viability," *Blood* 46(2):209-218 (1975).
Murphy et al., "Increased Mortality, Postoperative Morbidity, and Cost After Red Blood Cell Transfusion in Patients Having Cardiac Surgery," *Circulation*, 116:2544-2552 (2007).
Musante et al., "Active Focal Segmental Glomerulosclerosis is Associated with Massive Oxidation of Plasma Albumin," *Journal of the American Society of Nephrology*, 18(3):799-810 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Parkkinen et al., "Plasma ascorbate protects coagulation factors against photooxidation," *Thromb Haemost* 75(2):292-297 (1996).
Picker et al., "Current methods for the reduction of blood-borne pathogens: a comprehensive literature review," *Blood Transfusion* 11:343-348 (2013).
Pidcoke et al., "Primary hemostatic capacity of whole blood: a comprehensive analysis of pathogen reduction and refrigeration effects over time," *Transfusion* 53:137S-149S (2013).
Poncelet et al., "Tips and tricks for flow cytometry-based analysis and counting of microparticles," *Transfus. Apher. Sci.* 53(2):110-126 (2015).
Poxton, "Antibodies to lipopolysaccharide," *Journal of Immunological Methods*, 186:1-15 (1995).
Prefiltration before membrane filtration, hydrophobic, 25 μm 142 mm, retrieved on Aug. 26, 2014, from: www.emdmillipore.com/US/en/product/Prefiltration-before-membrane-filtration.
Pries et al., "Biophysical aspects of blood flow in the microvasculature," *Cardiovascular Research*, 32:654-667 (1996).
Ramstack et al., "Shear-induced activation of platelets," *J. Biomech.*, 12:113-125 (1979).
Reynolds et al., "S-nitrosohemoglobin deficiency: A mechanism for loss of physiological activity in banked blood," *Proceedings of the National Academy of Sciences*, 104(43):17058-17062 (2007).
Rock et al., "Nutricel as an additive solution for neonatal transfusion," *Transfusion Science*, 20:29-36 (1999).
Sambuceti et al., "Why should we study the coronary microcirculation?," *Am J Physiol Heart Circ Physiol*, 279:H2581-H2584 (2000).
Schubert et al., "Whole blood treated with riboflavin and ultraviolet light: Quality assessment of all blood components produced by the buffy coat method," *Transfusion* 55(4):815-823 (2014).
Sheffield et al., "Changes in coagulation factor activity and content of di(2-ethylhexyl) phthate in frozen plasma units during refrigerated storage for up to 5 days after thawing," *Transfusion*, 52:494-502 (2012).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).

Sohmer et al., "Phosphoenolypyruvate (PEP) Effects on Fresh and Stored Red Blood Cells," *Proceedings of the Society for Experimental Biology and Medicine*, 171:24-33 (1982).
Su et al., "Impermeable barrier films and protective coatings based on reduced graphene oxide," *Nature Communications* 5 Article No. 4843 (2014).
Supplementary European Search Report dated Jan. 20, 2015 in European Patent Application No. 12822378.2.
Sutera et al., "Deformation and Fragmentation of Human Red Blood Cells in Turbulent Shear Flow," *Biophys. J.*, 15:1-10 (1975).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-days-old AS-1 RBCs," *Transfusion*, 41:550-555 (2001).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).
"Transition and Turbulence," https://www.princeton.edu/~asmits/Bicycle_web/transition.html . Adapted from The Engine and the Atmosphere: An Introduction to Engineering by Z. Warhaft, Cambridge University Press, (1997).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C. in additive solution (AS-1, AS-3, or AS-5) for 42 days and then biochemically modified, frozen, thawed, washed, and stored at 4° C. in sodium chloride and glucose solution for 24 hours," *Transfusion*, 40:1341-1345 (2000).
Wallvik et al., "Platelet Concentrates Stored at 22° C. Need Oxygen the Significance of Plastics in Platelet Preservation," *Vox Sanguinis*, 45(4):303-311 (1983).
Wallvik et al., "The platelet storage capability of different plastic containers," *Vox Sanguinis*, 58(1):40-44 (1990).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely Injured: Does Age of Transfused Blood Affect Outcomes?," *The Journal of TRAUMA*, 65(4):794-798 (2008).
Wilding et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion* 7, 401-408 (1967).
Wu et al., "Polymer microchips bonded by $O_2$-plasma activation," *Electrophoresis*, 23:782-790 (2002).
Yazer et al., "Coagulation factor levels in plasma frozen within 24 hours of phlebotomy over 5 days of storage at 1 to 6° C.," *Transfusion*, 48:2525-2530 (2008).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).
Zimring et al., "Established and theoretical factors to consider in assessing the red cell storage lesion," *Blood*, 125:2185-2190 (2015).
Extended European Search Report dated Oct. 9, 2018, in European Patent Application No. 16784043.8.

(56) References Cited

OTHER PUBLICATIONS

International Search Report for PCT/US2016/051115 dated Nov. 21, 2016.
International Search Report for PCT/US2017/034410 dated Dec. 22, 2017.
Extended European Search Report dated Apr. 16, 2019, in European Patent Application No. 16845192.0.
Gardner, "Problems of Multiple Transfusions," *Official Journal of the California Medical Associate*, 83(2):93-97 (1958).
Peirce et al., "The Membrane Lung: Studies with a New High Permeability Co-Polymer Membrane," *Trans. Amer. Soc. Artif. Int. Organs* vol. XIV:220-226 (1968).
Steurer et al., "Trauma and Massive Blood Transfusions," *Curr. Anesthesiol. Rep* 4:200-208 (2014).
Paillous et al. "Mechanisms of photosensitized DNA cleavage," *J. Photochem. Photobiol. B: Biol.* 20:203-209 (1993).
Pelletier et al., "Pathogen inactivation techniques," *Best Practice & Research Clinical Haematology* 19(1):205-242 (2006).
Seghatchian et al., "Pathogen-reduction systems for blood components: The current position and future trends," *Transfusion and Apheresis Science* 35:189-196 (2006).
Zavizion et al., "Inactivation of mycoplasma species in blood by INACTINE PEN110 process," *Transfusion* 44:286-293 (2004).
Cardo et al., "Pathogen inactivation of *Leishmania donovani infantum* in plasma and platelet concentrates using riboflavin and ultraviolet light," *Vox Sanguinis* 90:85-91 (2006).
Cardo et al., "Pathogent inactivation of *Trypanosoma cruzi* in plasma and platet concentrates using riboflavin and ultraviolet light," *Transfusion and Apheresis Science* 37:131-137 (2007).
Corbin, "Pathogen Inactivation of Blood Components: Current Status and Introduction of an Approach Using Riboflavin as a Photosensitizer," International Journal of Hematology Supplement II 76:253-257 (2002).
Erickson et al., "Evaluation of in vitro Quality of Stored RBC after Treatment with S303 Pathogen Inactivation at Varying Hematocrits," Transfusion DUP—General Collection 48(2) Supplement (2008).
Fast et al., "Inactivation of Human White Blood Cells in Red Blood Cell Products Using the MIRASOL® System for Whole Blood," Blood Abstract #2897 110(11)(pt. 1) (2007).
Goodrich, "The Use of Riboflavin for the Inactivation of Pathogens in Blood Products," Vox Sanguinis Suppl. 2 78:211-215 (2000).
International Search Report for PCT/US2016/033151 dated Oct. 13, 2016.
Janetzko et al., "Pathogen reduction technology (Mirasol®) treated singledonor platelets resuspended in a mixture of autologous plasma and PAS," Vox Sanguinis 97:234-239 (2009).
Vrielink et al., "Transfusion-transmissible infections," Current Opinion in Hematology 5:396-405 (1998).
Agarwal et al., "Effect of pre-storage gamma irradiation on red blood cells," *Indian Journal of Medical Research* 122(5):385 (2005).
Extended European Search Report dated Jun. 5, 2019, in European Patent Application No. 19158815.1.
Apstein, et al., "Effect of erythrocyte storage and oxyhemoglobin affinity changes on cardiac function," Am J. Physiol 248: H508-15 (1985).
Aydogan, et al., "Impaired erythrocytes deformability in H(2)O(2}-induced oxidative stress: protective effect of L-carnosine," Clin Hemorheol Microcirc 39: 93-8 (2008).
Babic, "In vitro function and phagocytosis of galactosylated platelet concentrates after longterm refrigeration," Transfusion 47: 442-51 (2007).
Becker, et al., "Studies of platelet concentrates stored at 22 C. nad 4 C.," *Transfusion* 13: 61-8 (1973).
Benesch, et al., "The effect of organic phosphates from the human erythrocyte on the allosteric properties of hemoglobin," *Biochem Biophys Res Commun* 26: 162-7 (1967).
Bersin. et al., "Importance of oxygen-haemoglobin binding to oxygen transport in congestive heart failure," Br Heart J 70: 443-7 (1993).
Bordbar, et al., "Identified metabolic signature for assessing red blood cell unit quality is associated with endothelial damage markers and clinical outcomes," Transfusion 56: 852-62 (2016).
Browne, et al., "The molecular pathobiology of cell membrane iron: the sickle red cell as a model" *Free Radic Biol Med* 24: 1040-8 (1998).
Browne, et al., "Removal of erythrocyte membrane iron in vivo ameliorates the pathobiology of murine thalassemia," J Clin Invest 100: 1459-64 (1997).
Burns, et al., "Anaerobic Storage Improves the Mechanical Properties of Stored Red Blood Cells," Transfusion 52: 83A (2012).
Burns, et al., "Deterioration of red blood cell mechanical properties is reduced in anaerobic storage," Blood Transfus 14: 80-8 (2016).
Cabrales, et al., "Microvascular pressure and functional capillary density in extreme hemodilution with low-and high-viscosity dextran and a low-viscosity Hb-based O2 carrier," American Journal of Physiology-Heart and Circulatory Physiology 287: H363-H73 (2004).
Cabrales, et al., "Plasma viscosity regulates systemic and microvascular perfusion during acute extreme anemic conditions," Am J. Physiol Heart Circ Physiol 291: H2445-52 (2006).
Cannon et al., "Damage control resuscitation in patients with severe traumatic hemorrhage: A practice management guideline from the Eastern.Association for the Surgery of Trauma," J Trauma Acute Care Surg 82: 605-17 (2017).
Cap et al., "Whole Blood Transfusion," *Military Medicine* 183, 9/10:44 (2018).
Chanutin, et al., "Effect of organic and inorganic phosphates on the oxygen equilibrium of human erythrocytes," Arch Biochem Biophys 121: 96-102 (1967).
Chatpun, et al., "Cardiac mechanoenergetic cost of elevated plasma viscosity after moderate hemodilution," Biorheology 47: 225-37 (2010).
Chatpun, et al., "Cardiac systolic function recovery after hemorrhage determines survivability during shock," J Trauma 70: 787-93 (2011).
Chatpun, et al., "Effects of plasma viscosity modulation on cardiac function during moderate hemodilution," Asian J Transfus Sci 4: 102-8 (2010).
Choi, et al., "Influence of storage temperature on the responsiveness of human platelets to agonists," Ann Clin Lab Sci 33: 79-85 (2003).
Chouchani, et al., "Ischaemic accumulation of succinate controls reperfusion injury through mitochondrial ROS," Nature 515: 431-5 (2014).
Coene. "Paired analysis of plasma proteins and coagulant capacity after treatment with three methods of pathogen reduction," Transfusion 54: 1321-31 (2014).
Cotton et al., "A Randomized Controlled Pilot Trial of Modified Whole Blood Versus Component Therapy in Severely Injured Patients Requiring Large Volume Transfusions," *Annals of Surgery* 258(4) (2013).
D'Alessandro, et al., "Heterogeneity of blood processing and storage additives in different centers impacts stored red blood cell metabolism as much as storage time: lessons from REDS-11I-Omics," Transfusion 59: 89-100 (2019).
D'Alessandro, et al., "Time-course investigation of SAGM-stored leukocyte-filtered red bood cell concentrates: from metabolism to proteomics," Haematologica 97: 107-15 (2012).
D'Alessandro, et al., "Red blood cell metabolism under prolonged anaerobic storage," Mol Biosyst 9: 1196-209 (2013).
D'Alessandro, et al., "Red blood cell metabolic responses to refrigerated storage, rejuvenation, and frozen storage," Transfusion 57: 1019-30 (2017).
D'Alessandro, et al., "Metabolomics of AS-5 RBC supernatants following routine storage," Vox Sang (2014).
D'Alessandro, et al., "An update on red blood cell storage lesions, as gleaned through biochemistry and omics technologies," Transfusion 55: 205-19 (2015).
D'Alessandro et al., "Red blood cell storage and clinical outcomes: new insights," Blood Transfus 15: 101-3 (2017).
D'Alessandro, et al., "Plasma succinate is a predictor of mortality in critically injured patients," Journal of Trauma and Acute Care Surgery 83: 491-5 (2017).

(56) References Cited

OTHER PUBLICATIONS

D'Alessandro, et al., "Plasma First Resuscitation Reduces Lactate Acidosis, Enhances Redox Homeostasis, Amino Acid and Purine Catabolism in a Rat Model of Profound Hemorrhagic Shock," Shock 46: 173-82 (2016).
D'Alessandro, et al., "Anaerobic storage Condition enhances GSH Levels while Maintaining Pentose Phosphate Pathway Activity," Transfusion 56: 51A (2016).
D'Alessandro, et al., "Red blood cell storage in additive solution-7 preserves energy and redox metabolism: a metabolomics approach," Transfusion 55: 2955-66 (2015).
D'Alessandro, et al., "Routine storage of red blood cell (RBC) units in additive solution-3: a comprehensive investigation of the RBC metabolome," Transfusion 55: 1155-68 (2015).
D'Alessandro, et al., "Omics markers of the red cell storage lesion and metabolic linkage," Blood Transfus 15: 137-44 (2017).
D'Alessandro, et al., "AltitudeOmics: Red Blood Cell Metabolic Adaptation to High Altitude Hypoxia," J Proteome Res 15: 3883-95 (2016).
D'Alessandro, et al., "Citrate metabolism in red blood cells stored in additive solution-3," Transfusion 57: 325-36 (2017).
D'Alessandro, et al., "Metabolic effect of alkaline additives and guanosine/gluconate in storage solutions for red blood cells," Transfusion 58: 1992-2002 (2018).
D'Alessandro, et al., "Effects of aged stored autologous red blood cells on human plasma metabolome," Blood Adv 3: 884-96 (2019).
D'Alessandro, et al., "Hitchhiker's guide to the red cell storage galaxy: Omics technologies and the quality issue," Transfus Apher Sci 56: 248-53 (2017).
D'Amici, et al., "Red blood cell storage in SAGM and AS3: a comparison through the membrane two-dimensional electrophoresis proteome," *Blood Transfusion = Trasfusione del sangue* 10 Suppl 2: s46-54 (2012).
Delgado, et al., "Platelet Function in Stored Whole Blood Measured by a Shear-and Von Willebrand Factor-Dependent Methodology is Retained During Storage at 4° C. for up to 7 Days," Transfusion 51: 65A (2011).
Dennis, et al., "Transfusion of 2,3 DPG-enriched red blood cells to improve cardiac function," Ann Thorac Surg 26: 17-6 (1978).
Dennis, et al., "Improved myocardial performance following high 2-3 diphosphoglycerate red cell transfusions," Surgery 77: 741-7 (1975).
De Wolski, et al., "Metabolic pathways that correlate with post-Transfusion circulation of stored murine red blood cells," Haematologica 101: 578-86 (2016).
Dumont, et al., "Performance of Anaerobic Stored Red Blood Cells Prepared Using a Prototype 02 & CO2 Depletion and Storage System," Transfusion 51s: SP89 (2011).
Dumont, et al., "Randomized cross-over in vitro and in vivo evaluation of a prototype anaerobic conditioning and storage system vs. standard aerobic storage," Vox Sang 103: 123 (2012).
European Search Report Jun. 18, 2019, in European Patent Application No. 19163305.6.
Ezuki et al., "Survival and recoery of apheresis platelets stored in a polyolefin container with high oxygen permeability," *Vox Sanguinis* 94:292-298 (2008).
Farber, et al., "Effect of decreased 02 affinity of hemoglobin on work performance during exercise in healthy humans," J Lab Clin Med 104: 166-75 (1984).
Feys. "Oxygen removal during pathogen inactivation with riboflavin and UV light preserves protein function in plasma for Transfusion," Vox Sang 106: 307-15 (2013).
Friesenecker, et al., "Arteriolar vasoconstrictive response: comparing the effects of arginine vasopressin and norepinephrine," Crit Care 10: R75 (2006).
Gehrke, et al., "Metabolomics evaluation of early-storage red blood cell rejuvenation at 4 degrees C. and 37 degrees C.," Transfusion 58: 1980-91 (2018).

Gevi, et al., "Alterations of red blood cell metabolome during cold liquid storage of erythrocyte concentrates in CPD-SAGM," J Proteomics 76 Spec No. 168-80 (2012).
Golan, et al., "Transfusion of fresh whole blood stored (4 degrees C.) for short period fails to improve platelet aggregation on extracellular matrix and clinical hemostasis after cardiopulmonary bypass," J Thorac Cardiovasc Surg 99: 354-60 (1990).
Haddaway, et al., "Hemostatic properties of cold-stored whole blood leukoreduced using a platelet-sparing versus a non-platelet-sparing filter," Transfusion (2019).
Hebbel, et al., Oxidation-induced changes in microrheologic properties of the red blood cell membrane. *Blood* 1990;76: 1015-20.
Hebbel. "Auto-oxidation and a membrane-associated 'Fenton reagent': a possible explanation for development of membrane lesions in sickle erythrocytes," Clin Haematol 14: 129-40 (1985).
Hershko. "Mechanism of iron toxicity and its possible role in red cell membrane damage," Semin Hematol 26: 277-85 (1989).
Hess, et al., "Advances in military, field, and austere Transfusion medicine in the last decade," Transfus Apher Sci 49: 380-6 (2013).
Hornsey, et al., "Cold storage of pooled, buffy-coat-derived, leucoreduced platelets in plasma," Vox Sang 95: 26-32 (2008).
Jagannathan, et al., "Oxidative stress under ambient and physiological oxygen tension in tissue culture," *Curr Pharmacol Rep* 2: 64-72 (2016).
Jarman, et al., "Rural risk: Geographic disparities in trauma mortality," Surgery 160: 1551-9 (2016).
Jarolim, et al., "Effect of hemoglobin oxidation products on the stability of red cell membrane skeletons and the associations of skeletal proteins: correlation with a release of them in," Blood 76: 2125-31 (1990).
Jenkins, et al., "Trauma hemostasis and oxygenation research position paper on remote damage control resuscitation: definitions, current practice, and knowledge gaps," Shock 41 Suppl 1: 3-12 (2014).
Jesch, et al., "Oxygen dissociation after Transfusion of blood stored in ACD or CPD solution," J Thorac Cardiovasc Surg 70: 35-9 (1975).
Jobes, et al., "Toward a definition of "fresh" whole blood: an in vitro characterization of coagulation properties in refrigerated whole blood for Transfusion," Transfusion 51: 43-51 (2011).
Jy, et al., "Release of Microparticles During Blood Storage is Influenced by Residual Platelets, Leukocytes and Oxygen Levels," Blood 120: 3435 (2012).
Kerger, et al., "Systemic and subcutaneous microvascular pO2 dissociation during 4-h hemorrhagic shock in conscious hamsters," Am J. Physiol 270: H827-H36 (1996).
Khorana, et al, "Blood Transfusions, thrombosis, and mortality in hospitalized patients with cancer," Arch Intern Med 168: 2377-81 (2008).
Kohli et al., "Packed red cells versus whole blood transfusion for severe paediatric anaemia, pregnancy-related anaemia and obstetric bleeding. an analysis of clinical proactice buidelines from sub-Saharan Africa and evidence underpinning recommendments," *Tropical Medicine and International Health* 24(1):11-22 (2019).
Korsten, et al., "Determination of %502 in More Than 1300 Fresh Erythrocyte Concentrates by Resonance Raman Spectroscopy," Transfusion 58: 215A (2018).
Kotwal, et al., "The Effect of a Golden Hour Policy on the Morbidity and Mortality of Combat Casualties," JAMA Surg 151: 15-24 (2016).
Kreuger, et al., "A clinical evaluation of citrate-phosphate-dextrose-adenine blood," Vox Sang 29: 81-9 (1975).
Kwan,et al., "Microfluidic analysis of cellular deformability of normal and oxidatively damaged red blood cells," Am J Hematol 88: 682-9 (2013).
Liu, et al., "Beneficial Role of Erythrocyte Adenosine A2B Receptor-Mediated AMP-Activated Protein Kinase Activation in High-Altitude Hypoxia," Circulation 134: 405-21 (2016).
Manno, et al., "Comparison of the hemostatic effects of fresh whole blood, stored whole blood, and components after open heart surgery in children," Blood 77: 930-6 (1991).
Miller. "New evidence in trauma resuscitation-is 1: 1: 1 the answer?" Perioperative medicine 2: 13 (2013).

(56) References Cited

OTHER PUBLICATIONS

Mollison, "The Introduction of Citrate as an Anticoagulant for Transfusion and of Glucose as a Red Cell Preservative," *British Journal of Haematology* 108:1318 (2000).
Mussano et al., "Cytokine, chemokine and growth factor profile of Platelet Rich Plasma," *Universita Degli Studi Di Tornio* 2016.
Nair, et al., "Cold-Stored Platelets in PAS Exhibit Superior Hemostatic Potential" Blood 126: 772 (2015) Abstract.
Nemkov, et al., "Metabolomics in Transfusion medicine," Transfusion 56: 980-93 (2015).
Nemkov, et al., "Hypoxia modulates the purine salvage pathway and decreases red blood cell and supernatant levels of hypoxanthine during refrigerated storage," Haematologica 103: 361-72 (2018).
Nemkov, et al., "Metabolism of Citrate and Other Carboxylic Acids in Erythrocytes as a Function of Oxygen Saturation and Refrigerated Storage," Front Med (Lausanne) 4: 175 (2017).
Nessen et al., "Fresh whole blood use by forward surgical teams in Afghanistan is associated with improved survival compared to component therapy without platelets," *Transfusion* 53:107S-113S (2013).
Nilsson, et al., "Association between venous thromboembolism and perioperative allogeneic Transfusion," Arch Surg 142: 126-32; discussion 33 (2007).
Paglia, et al., "Biomarkers defining the metabolic age of red blood cells during cold storage," Blood 128: e43-50 (2016).
Pallotta, et al., "Storing red blood cells with vitamin C and N-acetylcysteine prevents oxidative stress-related lesions: a metabolomics overview," Blood Transfus 12: 376-87 (2014).
Pallotta, et.al., "Supplementation of anti-oxidants in leucofiltered erythrocyte concentrates: assessment of morphological changes through scanning electron microscopy," Blood Transfus 12: 421-4 (2014).
Pidcoke, et al "Tenyear analysis of Transfusion in Operation Iraqi Freedom and Operation Enduring Freedom: increased plasma and platelet use correlates with improved survival," *Journal of Trauma and Acute Care Surgery*;73: S445-S52 (2012).
Prudent, et al., "Oxygen in Red Blood Cell Concentrates Influence of Donor's Characteristics, Location and Blood Processing," *Vox Sang* 113: 116 (2018).
Reisz. et al., Red blood cells in hemorrhagic shock: a critical role for glutaminolysis in fueling alanine transamination in rats. Blood Advances 2017;1: 1296-305.
Reisz, et al Methylation of protein aspartates and deamidated asparagines as a function of blood bank storage and oxidative stress in human red blood cells, Transfusion 58: 2978-91 (2018).
Reisz, et al., "Metabolic Linkage and Correlations to Storage Capacity in Erythrocytes from Glucose 6-Phosphate Dehydrogenase-Deficient Donors," Front Med (Lausanne) 4: 248 (2017).
Reisz, et al., "Oxidative modifications of glyceraldehyde 3-phosphate dehydrogenase regulate metabolic reprogramming of stored red blood cells," Blood 128: e32-42 (2016).
Risbano, et al., "Effects of Aged Stored Autologous Red Blood Cells on Human Endothelial Function," Am J Respir Crit Care Med 192: 1223-33 (2015).
Rolfsson, et al., "Metabolomics comparison of red cells stored in four additive solutions reveals differences in citrate anticoagulant permeability and metabolism," Vox Sang (2017).
Scott, et al., "Effect of excess alpha-hemoglobin chains on cellular and membrane oxidation in model beta-thalassemic erythrocytes," J Clin Invest 91: 1706-12 (1993).
Seok, et al., "Genomic responses in mouse models poorly mimic human inflammatory diseases," Proceedings of the National Academy of Sciences 110: 3507-12 (2013).
Sivertsen, et al., "Preparation of leukoreduced whole blood for Transfusion in austere environments; effects of forced filtration, storage agitation, and high temperatures on hemostatic function," *J Trauma Acute Care Surg* 84: S93-S103 (2018).
Shalev, et al., "Extremely high avidity association of Fe(III) with the sickle red cell membrane," Blood 88: 349-52 (1996).
Shapiro, "To filter blood or universal leukoreduction: what is the answer?," *Critical Care* 8(Suppl 2): S27-draftS30 (2004).
Snyder, et al., "In vitro and in vivo evaluation of a whole blood platelet-sparing leukoreduction filtration system," Transfusion 50: 2145-51 (2010).
Spinella, et al., "Prehospital hemostatic resuscitation to achieve zero preventable deaths after traumatic injury," Curr Opin Hematol (2017).
Spinella, et al., "Whole blood: back to the future," Curr Opin Hematol 23: 536-42 (2016).
Spinella et al., "Whole blood for hemostatic resuscitation of major bleeding," *Transfusion* 56:S190-S202 (2016).
Strandenes et al., "Emergency Whole-Blood Use in the Field: a Simplified Protocol for Collection and Transfusion," *SHOCK* 41(Suppl 1):76-83 (2014).
Strandenes et al., "Low Titer Group O Whole Blood in Emergency Situations," *SCHOCK* 41(Suppl 1): 70-75 (2014).
Sun, et al., "Purinergic control of red blood cell metabolism: novel strategies to improve red cell storage quality," Blood Transfus 15: 535-42 (2017).
Sun, et al., "Sphingosine-1-phosphate promotes erythrocyte glycolysis and oxygen release for adaptation to high-altitude hypoxia," Nat Commun 7: 12086 (2016).
Tannahill, et al., "Succinate is an inflammatory signal that induces IL-1beta through HIF-1alpha" Nature 496: 238-42 (2013).
Teisseire, et al., "Induced low P50 in anesthetized rats: blood gas, circulatory and metabolic adjustments," Respir Physiol 58: 335-44 (1984).
Tolinski, "Getting the Most out of Polypropylene, Polythylene and TPO," *Additives for Polyolefins*, Second Edition 2015.
Tsai, et al., "Microvascular perfusion upon exchange Transfusion with stored red blood cells in normovolemic anemic conditions," Transfusion 44: 1626-34 (2004).
Tsantes, et al., "Redox imbalance, macrocytosis, and RBC homeostasis," Antioxid Redox Signal 8: 1205-16 (2006).
Valeri, et al., "Improved oxygen delivery to the myocardium during hypothermia by perfusion with 2,3 DPG-enriched red blood cells," Am Thorac Surg 30: 527-35 (1980).
Valeri. "Circulation and hemostatic effectiveness of platelets stored at 4 C. or 22 C.: studies in aspirintreated normal volunteers," Transfusion 16: 20-3 (1976).
Valeri. "Hemostatic effectiveness of liquid-preserved and previously frozen human platelets," N Engl J Med 290: 353-8 (1974).
Van Buskirk, et al., "Comparison of Cytokine, Cell-free Hemoglobin, and Isoprostane Accumulations in Packed Red Blood Cells During Novel Anaerobic and Conventional Cold Storage," Transfusion 54S: SP53 (2014).
Van Buskirk, et al., "Comparison of microparticles production in packed red blood cells stored under anaerobic and conventional cold storage condition," Vox Sang 105 (S1): 150 (2007).
Van Buskirk, et al., "Evaluation of Select Red Blood Cell Biochemical and Coagulation Properties in Whole Blood Stored Using a Novel Anaerobic Storage Platform," Transfusion 56: 54A (2016).
Van Slyke, "An Apparatus for Determination of the Gases in Blood and Other Solutions," *Chemistry* 7:229-231 _1921.
Voigt, et al., "Effects of a restrictive Blood Transfusion protocol on acute pediatric burn care: Transfusion threshold in pediatric burns," J Trauma Acute Care Surg 85: 1048-54 (2018).
Williams, "Blood Transfusion on Cruise Ships; A 36 Month Review of Preliminary Data," *THOR Trauma Hemostasis & Oxygenation Research Network, RDCR Symposium, Bergen* (2013).
Williams, et al., "Transfusion of Anaerobically Stored Red Blood Cells Improves Recovery in Experimental Rat Hemorrhagic Shock Model," Transfusion 57: 33A (2017).
Williams, et al., "Transfusion of Anaerobically Stored Red Blood Cells Improves Recovery in Experimental Rat Hemorrhagic Shock Model," Shock Abstract (2019).
Wolfe, et al., "Molecular defect in the membrane skeleton of blood bank-stored red cells. Abnormal spectrin-protein 4.1-actin complex formation," J Clin Invest 78: 1681-6 (1986).

(56) References Cited

OTHER PUBLICATIONS

Wolfe. "Oxidative injuries to the red cell membrane during conventional blood preservation," Semin Hematol 26: 307-12 (1989).
Woodson. "Functional consequences of altered blood oxygen affinity," *Acta Biol Med Ger* 40: 733-6 (1981).
Yalcin, et al., "Increased hemoglobin O2 affinity protects during acute hypoxia," *Am J. Physiol Heart Circ Physiol* 303: H271-81 (2012).
Yoshida, et al., "Oxygen content—uncontrolled and overlooked parameter associated with stored red cell concentrate: Unexpectedly wide distribution," Vox Sang 112: P-244 (2017) Abstract.
Yoshida, et al., "Enhancing uniformity and overall quality of red cell concentrate with anaerobic storage," Blood Transfus 15: 172-81 (2017).
Yoshida, et al., "Toward a comprehensive biochemical model of human erythrocyte: relationship between metabolic and osmotic state of the cell and the state of hemoglobin," Prog Clin Biol Res 319: 179-93; discussion 94-6 (1989).
Yoshida, et al., "Unexpected Variability of Hemoglobin Oxygen Saturation in Packed Red Blood Cells upon Donation Suggests Uncontrolled and Overlooked Parameter Associated with the Development of the Storage Lesion," Transfusion 57 (2017).
Yoshida, et al., "Red blood cell storage lesion: causes and potential clinical consequences" Blood Transfus 17: 27-52 (2019).
Yoshida, et al., "Reduction of Microparticle Generation During Anaerobic Storage of Red Blood Cells," Transfusion 52: 83A (2012).
Yuasa et al., "Improved extension of platelet storage in a polyolefin container with higher oxygen permeability," *British Journal of Hematology* 126:153-159 (2004).
Zaroulis, et al., "Lactic acidemia in baboons after Transfusion of red blood cells with improved oxygen transport function and exposure to severe arterial hypoxemia," *Transfusion* 19: 420-5 (1979).
Zielinski et al., "Back to the future: The renaissance of whole-blood transfusions for massively hemorrhaging patients," *Surgery* 155(5) 883-886 (2014).
Zielinski, et al., "Prehospital Blood Transfusion programs: Capabilities and lessons learned," *J Trauma Acute Care Surg* 82: S70-s8 (2017).
Zingarelli, et al., "Part I. Minimum Quality Threshold in Preclinical Sepsis Studies (MQTiPSS) for study design and humane modeling endpoints," Shock 51: 10-22 (2019).
Zink, et al., "Noninvasive Evaluation of Active Lower Gastrointestinal Bleeding. Comparison Between Contrast-Enhanced MDCT and 99mTcLabeled RBC Scintigraphy," American Journal of Roentgenology 191: 1107-14 (2008).
Zinkham, et al., "Carboxyhemoglobin levels in an unstable hemoglobin disorder (Hb Zurich): effect on phenotypic expression," Science 209: 406-8 (1980).

\* cited by examiner

SYSTEM FOR EXTENDED STORAGE OF RED BLOOD CELLS AND METHODS OF USE

CROSS REFERENCE TO RELATED APPLICATIONS

This application is a continuation of U.S. application Ser. No. 14/924,179, filed Oct. 27, 2015 (allowed), which is a continuation of U.S. application Ser. No. 13/541,554, filed Jul. 3, 2012 (now U.S. Pat. No. 9,199,016), which claims the benefit of the filing date of U.S. Provisional application 61/504,640, filed on Jul. 5, 2011, and U.S. Provisional Application No. 61/504,644, filed Jul. 5, 2011; is a CIP of U.S. patent application Ser. No. 12/901,350, filed on Oct. 8, 2010 (now U.S. Pat. No. 8,535,421), which claims the benefit of U.S. Provisional Application No. 61/331,693 filed on May 5, 2010; is a CIP of U.S. patent application Ser. No. 13/115,532, filed May 25, 2011 (now U.S. Pat. No. 8,569,052), which is a CON of U.S. patent application Ser. No. 12/903,057, filed on Oct. 12, 2010 (abandoned), which claims the benefit of U.S. Provisional Application No. 61/250,661 filed on Oct. 12, 2009; and is a CIP of U.S. patent application Ser. No. 13/289,722, filed on Nov. 4, 2011 (pending), which claims the benefit of U.S. Provisional Patent Application Ser. No. 61/410,684 filed on Nov. 5, 2010, the contents of each of which are incorporated herein by reference in their entireties.

FIELD OF THE DISCLOSURE

The present disclosure relates to the systems and methods for the preservation of blood and red blood cells. More particularly, the disclosure relates to the systems and methods for the prolonged anaerobic storage of red blood cells from collection to transfusion.

BACKGROUND OF THE INVENTION

The supplies of liquid blood are currently limited by storage systems used in conventional blood storage practice. Using current systems, stored blood expires after a period of about 42 days of refrigerated storage at a temperature above freezing (i.e., 4° C.) as packed blood cell preparations. Expired blood cannot be used and must be discarded because it will harm the ultimate recipient. One of the primary reasons for blood spoilage is its continued metabolic activity after it is stored. For example, in 2007, more than 45 million units of red blood cells (RBCs) were collected and stored globally (15.6 million in the US). During refrigerated storage, RBCs become progressively damaged by storage lesions. When transfused within the current 6-week limit, stored RBCs have lower quality (fraction of RBC removed; compromised $O_2$ delivery capacity) as well as potential toxicity, often manifested as side effects of transfusion therapy. These storage lesions are observed as altered biochemical and physical parameters associated with stored cells. Examples of these include in vitro measured parameters such as reduced metabolite levels (ATP and 2,3-DPG), reduced surface area, echinocytosis, phosphatidylserine exposure, and reduced deformability.

Stored blood undergoes steady deterioration which is partly caused by hemolysis, hemoglobin degradation and reduced adenosine triphosphate (ATP) concentration that occur during the storage period. These reasons and others limit the amount of readily available high quality blood needed for transfusions.

As discussed above, when RBCs are stored under refrigeration at temperatures above freezing (e.g., 1-6° C., standard storage conditions) in a blood storage bag, away from mechanical stress and the constantly cycling environment of the circulation, the senescence process is partially suspended. However, with the lack of constant nutrient replenishment and waste removal under refrigerated storage, RBCs are gradually damaged, resulting in compromised physiological functions. By way of example, the following problems occur during extended storage:

When RBCs are stored for an extended period, storage lesions accumulate and deteriorate RBCs and cause up to 1% of RBCs to be hemolyzed during storage and up to 25% to be removed shortly after transfusion.

Non-viable RBCs cause iron overload in chronically transfused patients.

Transfusion does not always achieve the intended outcome of increased tissue perfusion.

Hemoglobin in RBCs do not release oxygen efficiently at tissues due to loss of 2,3-DPG.

RBCs are not able to enter and perfuse capillary beds due to loss of deformability.

Transfusing RBCs stored for longer periods may result in higher morbidity and longer hospital stays compared to transfusing "fresher" red cells. Higher morbidity and longer hospital stays result with RBCs that are stored longer than 6 weeks, in comparison to fresher red cells. For example, negative clinical outcomes in cardiac surgery occur when using 'older' blood; multiple organ failure in surgical patients reflecting the age of transfused red cells; correlation between older units and increased mortality in severe sepsis; failure to improve $O_2$ utilization attributed to decreased 2,3-DPG and decreased cardiac index associated with increased blood viscosity This evidence suggests that the ineffectiveness and negative consequences of transfusion is attributable at least in part to the compromising effects of extended storage of RBCs. In addition to immediate removal by the recipient of certain RBCs, consequences of RBC storage lesions include: (i) Depletion of ATP (loss of RBC's ability to dilate the pre-capillary arteriole); (ii) Depletion of 2,3-DPG; (iii) Accumulation of oxidative damage caused by reactive oxygen species (ROS) formed by the reaction of denatured hemoglobin with $O_2$; and (iv) Decreased RBC deformability and increased RBC viscosity-caused in part by oxidative damage to membrane and cytoskeleton. Less deformable RBCs are excluded from capillary channels resulting in low capillary occupancy and reduced tissue perfusion. Massive transfusion of un-deformable cells may also contribute to multiple organ failure by blocking the organs' capillary beds. After transfusion, 2,3-DPG is synthesized relatively quickly in vivo to ~50% of the normal level in as little as 7 hours and to ~95% of the normal level in 2-3 days. However, since 2,3-DPG-depleted cells do not recover their levels immediately, $O_2$-carrying capacity is compromised to the detriment of critically ill patients requiring immediate $O_2$ delivery and tissue perfusion. There are numerous reports that emphasize the importance of RBCs with high oxygen carrying capacity in such clinical situations.

Storage of frozen blood is known in the art but such frozen blood has limitations. For a number of years, frozen blood has been used by blood banks and the military for certain high-demand and rare types of blood. However, frozen blood is difficult to handle. It must be thawed which makes it impractical for emergency situations. Once blood is thawed, it must be used within 48 hours. U.S. Pat. No.

6,413,713 to Serebrennikov is directed to a method of storing blood at temperatures below 0° C.

U.S. Pat. No. 4,769,318 to Hamasaki et al. and U.S. Pat. No. 4,880,786 to Sasakawa et al. are directed to additive solutions for blood preservation and activation. U.S. Pat. No. 5,624,794 to Bitensky et al., U.S. Pat. No. 6,162,396 to Bitensky et al., and U.S. Pat. No. 5,476,764 are directed to the storage of red blood cells under oxygen-depleted conditions. U.S. Pat. No. 5,789,151 to Bitensky et al. is directed to blood storage additive solutions.

Additive solutions for blood preservation and activation are known in the art. For example, Rejuvesol (available from enCyte Corp., Braintree, Mass.) is added to blood after cold storage (i.e., 4° C.) just prior to transfusion or prior to freezing (i.e., at −80° C. with glycerol) for extended storage. U.S. Pat. No. 6,447,987 to Hess et al. is directed to additive solutions for the refrigerated storage of human red blood cells.

The effects of elevation and preservation of ATP levels in blood storage situations has been studied. For example, in "Studies In Red Blood Cell Preservation-7. In Vivo and in Vitro Studies With A Modified Phosphate-Ammonium Additive Solution," by Greenwalt et al., Vox Sang 65, 87-94 (1993), the authors determined that the experimental additive solution (EAS-2) containing in mM: 20 $NH_4Cl$, 30 $Na_2HPO_4$, 2 adenine, 110 dextrose, 55 mannitol, pH 7.15, is useful in extending the storage shelf-life of human RBCs from the current standard of 5-6 weeks to an improved standard of 8-9 weeks. Packed RBCs are suitable for transfusion following the removal of the supernatant with a single washing step. Greenwalt et al. also conclude that factors other than ATP concentration appear to play an increasingly important role in determining RBC viability after 50 days of storage. They cite the results of L. Wood and E. Beutler in "The Viability Of Human Blood Stored In Phosphate Adenine Media," Transfusion 7, 401-408 (1967), find in their own experiments that the relationship between ATP concentration and 24-hour RBC survival measurements appear to become less clear after about 8 weeks of storage. E. Beutler and C. West restate that the relationship between red cell ATP concentration and viability is a weak one after prolonged periods of storage in "Storage Of Red Cell Concentrates In CPD-A2 For 42 and 49 Days," J. Lab. Clin. Med. 102, 53-62 (1983).

In "Effects Of Oxygen On Red Cells During Liquid Storage at +4° C.," by Hogman et al., Vox Sang 51, 27-34 (1986), the authors discuss that red cell content of ATP is slightly better maintained in anaerobic chamber than at ambient air storage after 2-3 weeks. Venous blood was refrigerated and deprived of additional oxygen during storage, by placing the oxygen-permeable storage bags in a nitrogen environment and thereby gradually reducing the level of oxygen saturation. The reduction in oxygen concentration occurs slowly during storage at 4° C., and is far from complete, starting at about 60% and reaching about 30% hemoglobin saturation at 5 weeks. No conclusion could be drawn concerning the effects of this procedure on the overall quality of stored cells. These authors did not address or significantly reduce the oxygen-dependent damage to hemoglobin and the oxygen-mediated damage caused by hemoglobin breakdown products.

Many patents have addressed different aspects of blood storage. One such patent is U.S. Pat. No. 4,837,047 to Sato et al. which relates to a container for storing blood for a long period of time to keep the quality of the blood in good condition. Sato et al. is directed at improving the storage life of the stored blood by maintaining a partial pressure of carbon dioxide gas in the blood at a low level. Such partial pressure is apparently obtained through normalization with the outside atmosphere. The container is made of a synthetic resin film which has a high permeability to carbon dioxide gas for the purpose of making it possible for the carbon dioxide gas to easily diffuse from the blood to outside. However, the problems caused by the interaction of the oxygen and hemoglobin in the blood are not addressed.

Another patent, U.S. Pat. No. 5,529,821 to Ishikawa et al. relates to a container and a method for the storage of blood to prevent adhesion of the blood to the container. Blood is stored in containers composed of a sheet material having a plurality of layers where a first sheet which contacts the blood substantially prevents the activation and adhesion of blood platelets to the layer. Again, however, the problems caused by the interaction of the oxygen and hemoglobin in the blood are not addressed.

In light of current technology, there is a need to improve the quality of red blood cells that are to be stored and to extend the storage life of such red blood cells in advance of transfusion to minimize morbidity associated with transfusions.

SUMMARY OF THE INVENTION

To address such needs and others, the present disclosure includes and provides a system and methodology for the preservation of red blood cells is provided in which red blood cells are, e.g., oxygen and carbon dioxide depleted, undergo treatment and are stored in an anaerobic environment to optimize preparation for transfusion.

The present disclosure includes a system and method for extended storage of red blood cells from collection to transfusion that optimizes red blood cells prior to transfusion.

The present disclosure provides for, and includes, a method for preparing red blood cells (RBCs) including obtaining whole blood, separating the RBCs from the whole blood to form packed RBCs, depleting oxygen to form oxygen depleted RBCs or depleting oxygen and carbon dioxide to form oxygen and carbon dioxide depleted RBCs and storing the oxygen depleted or oxygen and carbon dioxide depleted RBCs in an anaerobic storage environment to maintain an oxygen depleted or oxygen and carbon dioxide depleted condition.

In aspects of the present disclosure, the method may further include adding an additive solution to the packed RBCs to form a suspension. In some aspects the additive solution may include AS-1, AS-3, AS-5, SAGM, PAGG-SM, PAGG-GM, MAP, SOLX, ESOL, EAS61, OFAS1 or OFAS3 alone or in combination. In a further aspect, the additive solution may have a pH from 5.0 to 9.0. In another aspect, the additive may include an antioxidant. In some aspects according the present disclosure, the antioxidant may be quercetin, alpha-tocopheral, ascorbic acid, or enzyme inhibitors for oxidases.

In aspects of the present disclosure, an integrated blood storage system and method can include an oxygen and carbon dioxide removal system, a blood storage system and a pre-transfusion procedure to prepare the stored blood for transfusion.

Additionally, the present disclosure also includes a system and a method that may incorporate leukoreduction and editing steps to optimize RBCs in preparation for transfusion. Leukoreduction may include removing white blood cells that can carry viruses and cause fevers. Editing can include removing RBCs that exhibit indications of being compromised.

Accordingly, the present disclosure also provides a novel procedure for blood storage which addresses at least the problems of hemoglobin degradation, red blood cell lysis (hemolysis) and ATP and 2-3 DPG depletion in a manner consistent with the practice of autologous transfusion and enhanced heterologous transfusion logistics, and which achieves significant prolongation of the time during which refrigerated storage of red blood cells is not detrimental to their subsequent use.

The present disclosure further provides for a system and methodology for enhancing the effect of irradiation and stabilizing red cells prior to storage or during/after storage in preparation for transfusion.

The present disclosure further provides for a system and methodology for reducing the growth of aerobic bacteria and parasites present in red blood cells prior to storage or during storage in preparation for transfusion.

The present disclosure further provides for a system and methodology for minimizing hemolysis and morphology changes of red blood cells during storage in non DEHP storage bags.

The present disclosure further provides for a system and methodology for stabilizing and enhancing pathogen inactivation of red blood cells prior to storage or during storage in preparation for transfusion.

The present disclosure, still further provides for a system and methodology for providing nitric oxide to red blood cells during storage, after storage and immediately prior to transfusion, e.g., to permit vasodilation of the vessels of the recipient of the RBCs.

The present disclosure, still yet further provides for a system and methodology for reducing the volume of red blood cells after storage and re-oxygenating such RBCs immediately prior to transfusion.

DETAILED DESCRIPTION

Figure 1:
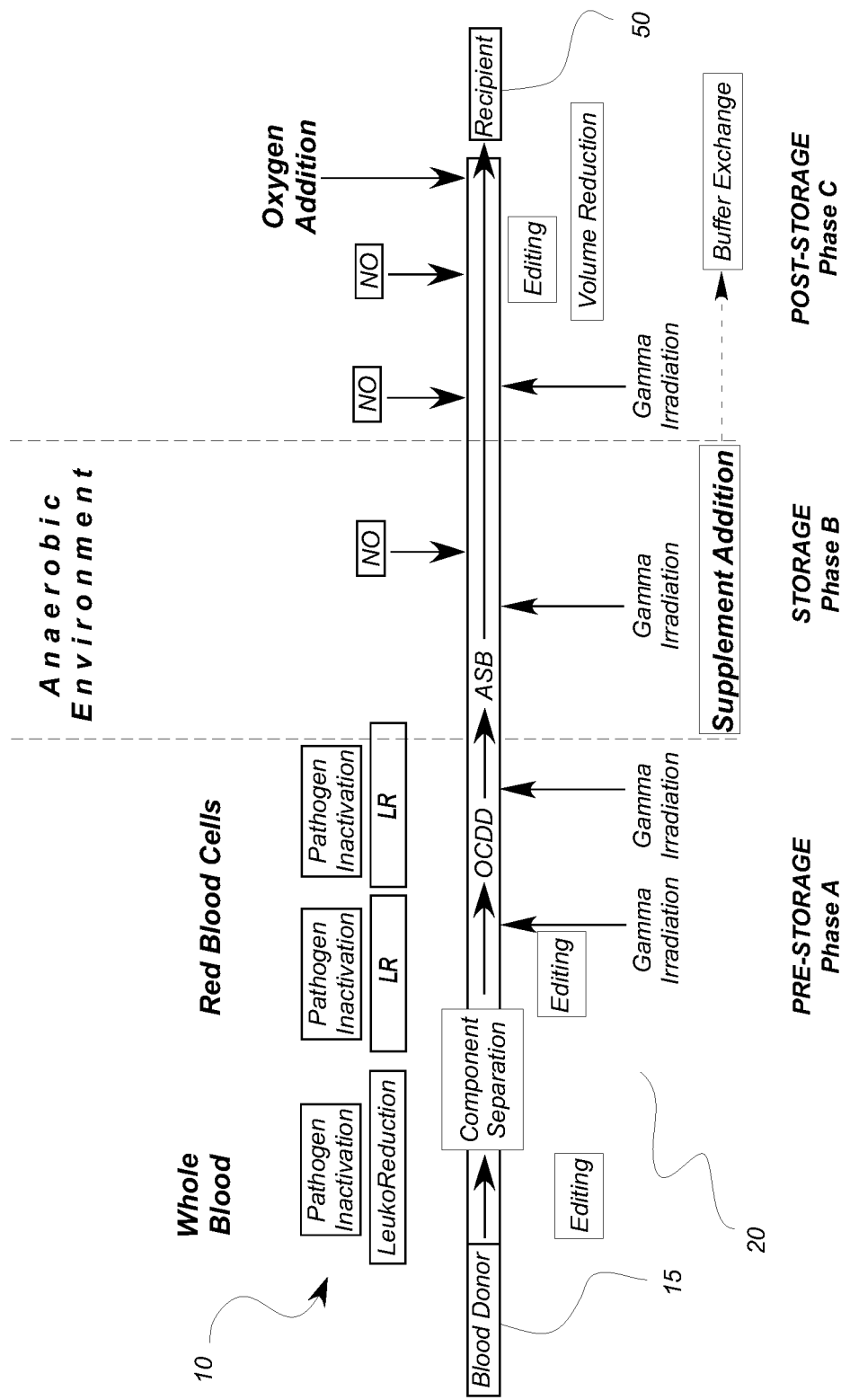
FIG. 1 illustrates an exemplary flowchart of the components and methodology from blood collection to transfusion using a blood anaerobic storage system of the present disclosure.

The transfusion of red blood cells (RBCs) is a life-saving therapy aimed at improving oxygenation of the tissues and vital end organs in severely anemic patients. The majority of RBC units used for transfusion are stored at 1-6° C. for up to 42 days in an oxygen-permeable polyvinylchloride blood bag that contains additive/preservative solution.

Exemplary Definitions:

Blood Donor: Whole blood is preferably donated from a healthy individual or donor and held in a blood bank for later use to be ultimately used by a recipient. Subjects who are scheduled for surgery or other treatment may donate blood for themselves in a process known as autologous blood donation. Alternatively, blood is donated for use by another in a process known as heterologous transfusion. The collection of a whole blood sample drawn from a donor, or in the case of an autologous transfusion from a patient, may be accomplished by techniques known in the art, such as through donation or apheresis.

Whole Blood: Whole blood is a suspension of blood cells that contains red blood cells, white blood cells, platelets suspended in plasma, including electrolytes, hormones, vitamins, antibodies, etc.

Red Blood Cells (RBCs): Human red blood cells in vivo are in a dynamic state. In whole blood, white blood cells are normally present in the range between 4,300 and 10,800 cells/μL and the normal RBC range at sea level is 5.4 million/μL (+ 0.8) for men and 4.8 million μL (+ 0.6) for women. The red blood cells contain hemoglobin, the iron-containing protein that carries oxygen throughout the body and gives red blood its color. The percentage of blood volume composed of red blood cells is called the hematocrit. Packed red blood cells may be prepared from whole blood using centrifugation techniques commonly known in the art. In an aspect according to the present disclosure, the packed red blood cells may be the blood component that is stored in the storage system for later transfusion.

The normal life span of a red blood cell (RBC) is 120 days. Approximately 0.875% of the RBCs are retired every 24 hours by the spleen and new RBCs are made by the bone marrow. Consequently, when blood is drawn from a donor, there are a percentage of white blood cells and a spectrum of cells of different ages.

The main function of RBCs is to exchange oxygen and carbon dioxide at lung and tissues, and unlike other cells in body, it does not rely on oxygen in oxidative phosphorylation but entirely on glycolysis for ATP production. ATP is critical for viability of RBC and together with 2,3-diphosphoglycerate (2,3-DPG), their free cytosolic concentrations are tightly regulated by their function on feedback inhibition to key enzymes in glycolytic pathway. Under a refrigerated storage condition, dis-inhibition of glycolytic pathway is desirable to overcome the gradual depletion of ATP and 2,3-DPG over several weeks of storage. Hemoglobin concentration in RBC is similar to 2,3-DPG and ATP, and its deoxygenated state has a binding pocked with high affinities for 2,3-DPG and ATP compared to oxy-hemoglobin. Thus, stripping this oxygen to few % occupancy (~60% occupied when collected and processed) will cause uptake of 2,3-DPG and ATP, resulting in reduced concentration of free molecules, stimulating glycolytic flux.

Platelets: The platelets are small cellular components of blood that facilitate the clotting process by sticking to the lining of the blood vessels. The platelets like the red blood cells are made by the bone marrow and survive in the circulatory system for 9 to 10 days before they are removed by the spleen. Platelets are typically prepared using a centrifuge to separate the platelets from the plasma.

Plasma: Plasma is a protein-salt solution and the liquid portion of the blood in which red and white blood cells and platelets are suspended. Plasma is 90% water and constitutes about 55 percent of the blood volume. One of the primary functions of plasma is to assist in blood clotting and immunity. Plasma is obtained by separating the liquid portion of the blood from the cells. Typically, plasma is separated from the cells by centrifugation. Centrifugation is the process used to separate the components of the whole blood into the plasma, the white blood cells, the platelets and the packed red blood cells. During centrifugation, the plasma will initially migrate to the top of a vessel during a light spin. The plasma is then removed from the vessel. The white blood cells and platelets are removed during a second centrifugation cycle to produce the packed red blood cells. This application will discuss an efficient alternative to using a centrifuge that minimizes the cost of traditionally used instrumentation.

In its most general form, the present disclosure provides for, and includes, an integrated system and method for the preparation and extended storage of red blood cells, from receipt of whole blood from a donor until transfusion to a recipient. By way of example, FIG. 1 illustrates an exemplary flowchart of the components and methodology from blood collection from a blood donor 15 to transfusion to a recipient 50 using a anaerobic storage method 10 and system 20 through Pre-Storage Phase A, Storage Phase B in an anaerobic environment, and Post-Storage Phase C. However, as understood with reference to the present disclosure, various combinations of the disclosed systems and methods are envisioned as within the scope of the disclosure, and the illustrated components and methodologies may be optionally substituted, eliminated or reordered.

By way of illustration, method 10 describes a storage system 20 that includes an optional additive addition, and oxygen, carbon dioxide, or oxygen and carbon dioxide (collectively referred to herein as O/CD) depletion of RBCs before and during storage, together with enhancing treatments include leukoreduction, editing, pathogen reduction, irradiation and nitric oxide treatment and oxygen addition to enhance the quality of stored RBCs and to optimize the transfusion process to a recipient and reduce morbidity associated with such transfusion.

Again referring to the drawings, and particular to FIG. 1, a method 10 describes storage system 20 from collection from a donor 15 to transfusion to a recipient 50. System 20 shows a method that has three phases during which different sub-processes or steps may occur. The three phases are generally: Pre-Storage Phase A, Storage Phase B and Post-Storage Phase C. As shown in FIG. 1, different steps of the blood storage process 20 can occur at different phases to achieve optimal blood transfusion results. For example, irradiation can optionally occur during Pre-Storage Phase A before oxygen removal, during Storage Phase B, during the Post-Storage Phase C, during Storage Phase B and a portion of Pre-Storage Phase A and Post-Storage Phase C, or combinations thereof, etc. Similarly, editing of RBCs (e.g., to remove moribund RBCs) can occur during Pre-storage Phase A, during Post-storage Phase C, or a combination thereof, etc. The anaerobic environment has synergistic relationships with steps such as the addition of nitric oxide, irradiation and pathogen inactivation, that provide advantages to the RBCs that must occur in such anaerobic environment, as will be discussed below. Accordingly, there exist several different sequences for the blood storage processing according to the present disclosure.

Pre-storage Phase A, includes the time from collection from a donor to storage in an anaerobic environment. During Phase A, whole blood may be collected from a donor, and the blood components, namely, plasma, platelets and RBCs may be separated. An optional additive solution may be added to the whole blood to aid in storage and/or processing, as further described herein. Processing such as pathogen inactivation, leukoreduction and editing may occur during Pre-storage Phase A. During Phase A, oxygen, carbon dioxide, or oxygen and carbon dioxide (O/CD) are depleted prior to Storage Phase B. O/CD may be depleted either by an oxygen, or oxygen and carbon dioxide depletion device (OCDD).

Storage Phase B is an anaerobic storage period, wherein RBCs are stored in an anaerobic storage environment.

Post-Storage Phase C, after storage in an anaerobic storage environment but prior to transfusion to recipient. Post-Storage Phase C may include processing such as volume reduction, editing, cleansing during buffer exchange, the addition of either or both nitric oxide and oxygen, etc.

Figure 2:
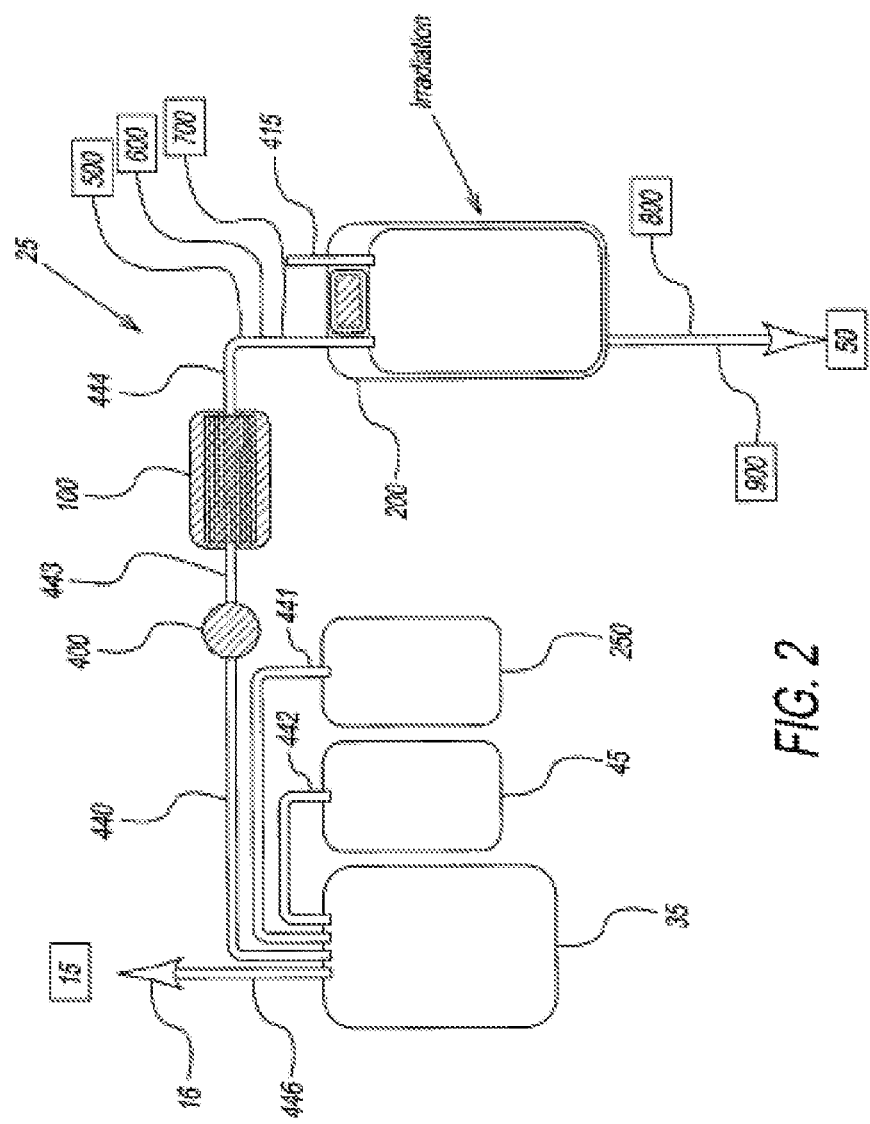
FIG. 2 illustrates an exemplary system according to the FIG. 1 of the present disclosure in which, blood is collected, components are separated, optional additive solution is added to packed RBC, leukoreduced then stored anaerobically.

Referring to the drawings and in particular to FIG. 2, an exemplary anaerobic storage system is shown and referenced using reference numeral 25. In certain embodiments, system 25 may be constructed so as to be disposable. Again, system 25 is an exemplary system, accordingly, different sub-processes or steps can occur at different times or during different phases as discussed above. Blood storage system 25 includes an oxygen/carbon dioxide depletion device 100 (OCDD 100), an anaerobic blood storage bag 200 and an optional additive solution bag 250. Components conventionally associated with the process of blood collection are a phlebotomy needle 16, a blood collection bag 35 containing an anti-coagulant and a bag 45 containing plasma. Tubing can connect the various components of the blood storage system 25 in various configurations (one embodiment shown). OCDD 100 removes oxygen and carbon dioxide from red blood cells traveling therethrough. System 25 may also contains a leukoreduction filter 400, and editing device 500, an irradiation device 600, a pathogen inactivation device 700, a volume reduction device 800 and a nitric oxide device 900 to immediately supply nitric oxide to the RBCs in advance of transfusion to a recipient 50. System 25 can contain all or a combination of such devices 400 through 900 in varying configurations as discussed below.

Components of system 25 are connected in a convention fashion. Tube 440 connects collection bag 35 with leukoreduction filter 400. Tube 441 connects solution bag 250 with collection bag 35. Tube 442 connects plasma bag 45 with collection bag 35. Tube 443 connects leukoreduction filter 400 with OCDD 100. Tube 444 connects OCDD 100 with blood storage bag 200. Blood storage system 25 is preferably a single-use, disposable, low cost system.

System components, namely, leukoreduction filter 400, editing device 500, irradiation device 600, pathogen inactivation device 700, volume reduction device 800 and nitric oxide device 900, perform various therapies for the RBCs prior to transfusion. Depending upon the therapies, such therapies are preferably performed on RBCs before passage through OCDD or after storage in storage bag 200. After being depleted in O/CD, RBCs are maintained in an oxygen, carbon dioxide, or oxygen and carbon dioxide depleted environment to ensure the desired results for the patient and to avoid morbidity commonly associated with transfusions using stored RBCs.

In certain aspects, if desired, after packed RBCs are collected from whole blood obtained from donor 15, an optional additive solution, e.g., from bag 250 may be provided to the packed RBCs to form a suspension of packed RBCs. Additive solutions may generally help to prevent rapid deterioration of RBCs. Additive solution bag 250 may include an additive solution optimized for anaerobic storage. For each of the several embodiments addressed herein, an additive solution from bag 250 may be provided prior to depleting O/CD from the RBCs. By way of example, between 50-300 ml of additive solution/unit of packed RBCs (450-500 ml whole blood draw) may be added. In certain aspects, 100 to 110 ml of additive solution per unit of packed RBCs may be added. In another aspect, 50 to 100 ml of additive solution per unit of packed RBCs may be added. In an aspect according the present disclosure, the 75 to 125 ml of additive solution per unit of packed RBCs may be added. In yet another aspect according the present disclosure, the 90 to 120 ml of additive solution per unit of packed RBCs may be added.

By way of example, the additive solution may include an aqueous solution of adenine, dextrose, mannitol, citrate ion, and dihydrogen phosphate ion. Alternatively, additive solutions may include AS-1, AS-3, AS-5, SAGM, PAGG-SM, PAGG-GM, EAS61, OFAS1, OFAS3, MAP, ESOL, SOLX and any combinations thereof. (See, Rossi's Principles of Transfusion Medicine $4^{th}$ edition, Simon, T; Snyder, E, et al. Wiley-Blackwell; M Shimizu, H Fujii, H Mizoguchi, M Masuda, K Toyama, Rinsho Ketsueki et al., "Multicenter clinical evaluation of red cell concentrates stored up to 6 weeks in MAP, a new additive solution," The Japanese Journal 33:148 (1992); Dumont L J, Yoshida T, AuBuchon J P, "Anaerobic storage of red blood cells in a novel additive solution improves in vivo recovery," Transfusion 49:458-64 (2009); U.S. Pat. No. 5,789,151, issued Aug. 4, 1998, entitled "Prolonged cold storage of red blood cells by oxygen removal and additive usage," issued Aug. 4, 1998; U.S. Pat. No. 4,769,318 issued Sep. 6, 1988 to Hamasaki et al. entitled "Additive Solution for Blood Preservation and Activation"; and U.S. Pat. No. 6,162,396 to Bitensky et al. issued Dec. 19, 2000 entitled "Blood Storage Device and Method for Oxygen Removal"; each of which are hereby incorporated by reference in their entireties).

Additive solution OFAS3 includes adenine, dextrose, mannitol, $NaH_2PO_4$, and optionally NaCl and/or $NH_4Cl$. Additive solution OFAS3 preferably includes ingredients having the following ranges: about 0.5-4.0 mmole/liter of adenine, about 50-150 mmole/liter of dextrose, about 20-70 mmole/liter of mannitol, about 0-100 mmole/liter of NaCl, about 2-20 mmole/liter of $NaH_2PO_4$, and about 0-30 mmole/liter $NH_4Cl$. Preferably OFAS3 has an adjusted pH from about 5.5-7.5 and includes about 2 mmole/liter adenine, about 110 mmole/liter dextrose, about 55 mmole/liter NaCl, and about 12 mmole/liter $NaH_2PO_4$ and an adjusted pH of about 6.5. Additional embodiments of OFAS3 are provided in U.S. Pat. No. 8,071,282, issued Dec. 6, 2011, which is herein incorporated by reference in its entirety.

TABLE 1

| Ingredient | Range (mM) |
| --- | --- |
| Adenine | 0.5-4.0 |
| Dextrose | 50-150 |
| Mannitol | 0-70 |
| NaCl | 0-100 |
| $NaH_2PO_4$ | 2-20 |
| $NH_4Cl$ | 0-30 |
| Effective Osm | 100-300 |
| Adjusted pH | 5.0-7.7 |
| mL added | 100-300 |

Figure 3A:
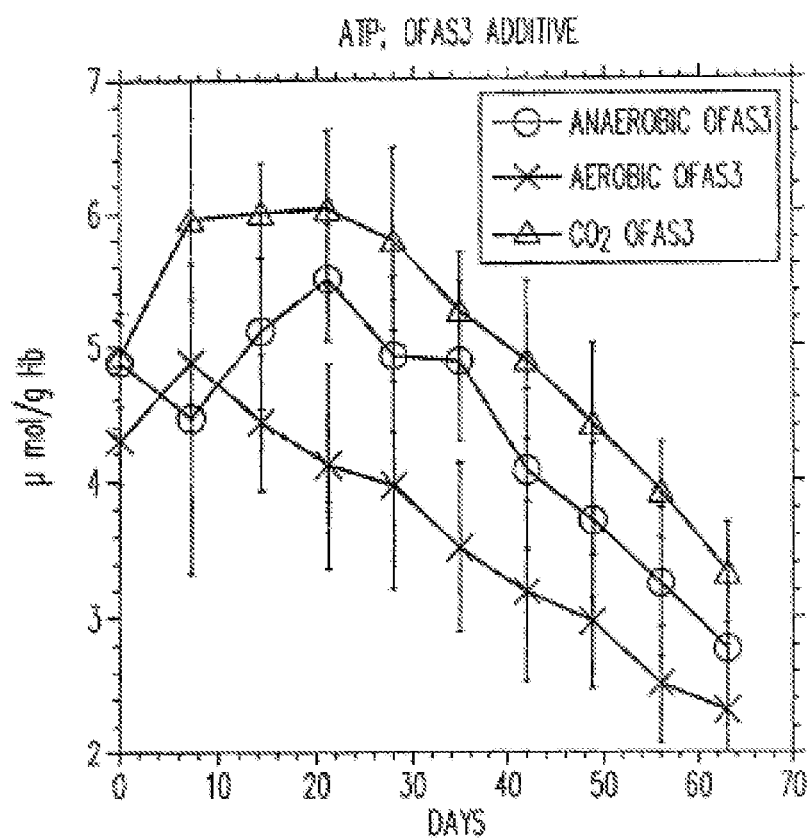
FIGS. 3a and 3b illustrate the effects of, oxygen and oxygen and carbon dioxide depletion on ATP and DPG, respectively, during extended storage in OFAS3 additive solution.
Figure 3B:
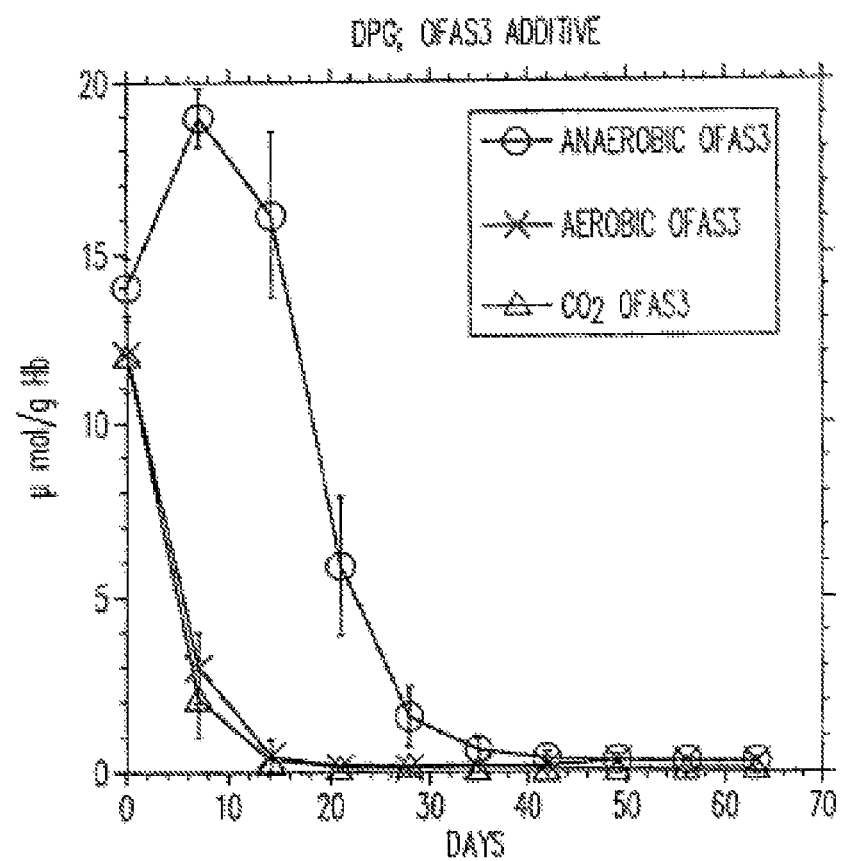

OFAS3 has shown enhanced ATP levels and good in vivo recovery as disclosed herein. FIG. 3a shows the effects of oxygen and oxygen and carbon dioxide depletion on ATP during extended storage in oxygen depleted or anaerobic OFAS3 additive solution. FIG. 3b shows the effects oxygen and oxygen and carbon dioxide depletion on 2, 3 DPG during extended storage in oxygen depleted or anaerobic OFAS3 additive solution. The highest ranges are from 8 to 30 days for ATP and from 0 to 20 days for 2, 3 DPG. Ideally, RBCs would be transfused to recipient 50 during such length of time.

To increase the time of acceptable in vivo recovery of RBCs in liquid storage, attempts have been made to improve additive solutions and storage processes. In "Studies In Red Blood Cell Preservation-7. In vivo and in vitro Studies With A Modified Phosphate-Ammonium Additive Solution," by Greenwalt et al., Vox. Sang. 65:87-94 (1993), the authors determined that the experimental additive solution (EAS-2) containing in mM: 20 $NH_4Cl$, 30 $Na_2HPO_4$, 2 adenine, 110 dextrose, 55 mannitol, pH 7.15, is useful in extending the storage shelf-life of human RBCs from the current standard of 5-6 weeks to an improved standard of 8-9 weeks. However, packed RBCs stored in the medium were not directly infusible but required the removal of the supernatant with a washing step prior to transfusion due to the presence of ammonium in the additive solution.

In other embodiments, the additive solution may include antioxidants. Particularly preferred are antioxidants that may be active under minimal oxygen conditions and therefore, potentially synergistic in their action in an anaerobic storage environment. For instance, the antioxidant may be selected from quercetin and other bioflavonoids, alpha-tocopheral, ascorbic acid, ebselen, oxypurinol, hydrocortisone and other enzyme (oxidase) inhibitor molecules, and combinations thereof. Quercetin, a flavonoid with antioxidant activity is safe and efficient to act as an antioxidant when administered clinically. Quercetin scavenges oxygen radicals, inhibits lipid peroxidation in vitro, and has been shown to reduce erythrocyte membrane damage. In certain embodiments, the antioxidant may be a flavonol. In other aspects, the flavonoid may be rutin or epicatechin. Ascorbic acid is very effective anti-oxidant, but can also function as pro-oxidant. However, since relatively high concentrations (~10 mM, concentration necessary to be effective in stored blood) and presence of iron (free or heme) and oxygen are necessary for its pro-oxidant activity, the anaerobic conditions of the present disclosure should provide a low effective concentration of use without concern for an pro-oxidant activity.

Leukoreduction

As shown in FIG. 1, the whole blood, packed RBCs, or suspension of RBCs may undergo leukoreduction 400. Leukoreduction is the general process of removing white blood cells from whole blood or red blood cells. As shown, the leukoreduction may occur prior to or after depleting oxygen, carbon dioxide or oxygen and carbon dioxide (O/CD) to form O/CD depleted RBCs, and before, during or after storing in said anaerobic storage environment.

Figure 4A:
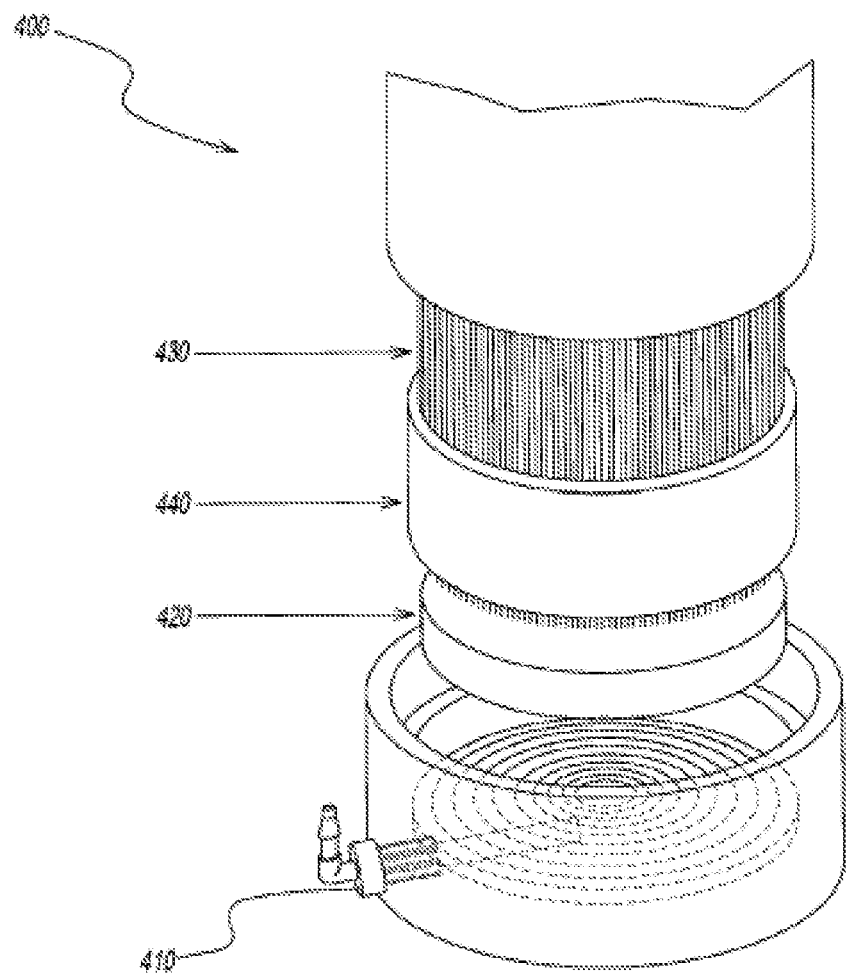
FIGS. 4a and 4b illustrate a partial detailed perspective view of an RBC inlet portion of the combination leukoreduction filter and $O_2/CO_2$ depletion device according to the system of FIG. 5.
Figure 4B:
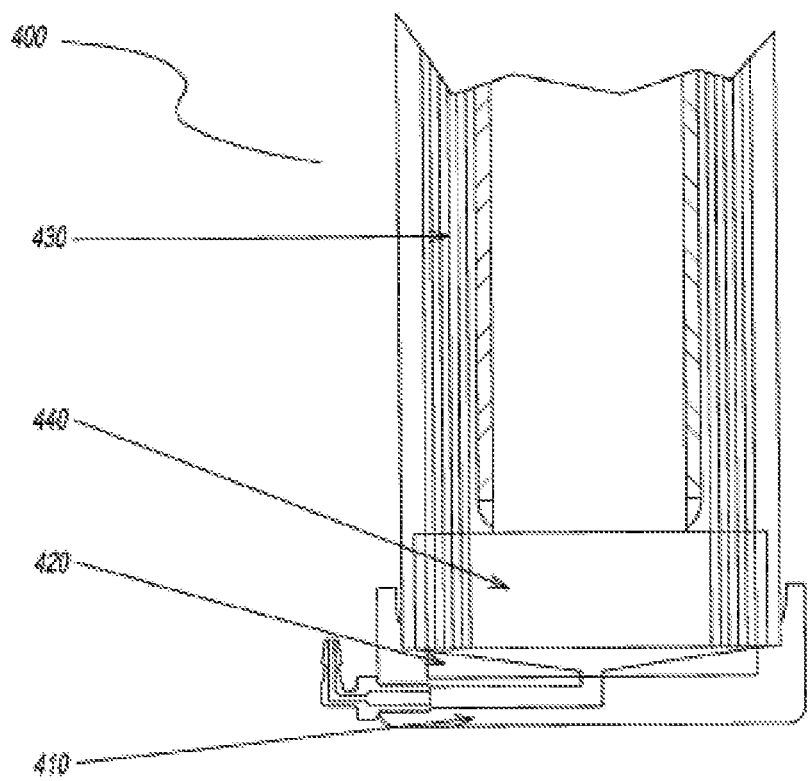

In accordance with certain aspects, referring to FIGS. 4a and 4b, a combination leukoreduction filter and OCDD 400 is shown. Combination leukoreduction and OCDD filter 400 includes an inlet flow distributor 410, a leukoreduction media 420, a plurality of hollow fibers and/or gas-permeable films or fibers 430, and a fiber/film support 440 to hold the plurality of fibers and/or gas-permeable films or fibers 430. Plurality of hollow fibers and/or gas-permeable films or fibers 430 are for the purpose of removing oxygen and or carbon dioxide from red blood cells and will be discussed further below in conjunction with OCDD 101.

Leukoreduction media 420 is preferably a fibrous or a felt-like filtering material that captures leukocytes (e.g., Pall Corporation), prior to such leukocytes travelling through plurality of hollow fibers and/or gas-permeable films or fibers 430 for oxygen, carbon dioxide, or oxygen and carbon dioxide depletion. In some aspects according to the present disclosure, the leukoreduction media may be a LeukoGuard-6® type filter media. In an aspect the leukoreduction media 420 may be Leukotrap® Affinity Plus Prion and Leukocyte Reduction Filter media. In an aspect the leukoreduction media 420 may be Leukotrap® media. Leukoreduction media 420 may comprise a fibrous medium, for example a medium prepared from melt-blown fibers, as disclosed in, for example, U.S. Pat. Nos. 4,880,548; 4,925,572; 5,152,905, 5,443,743, 6,231,770, and 7,361,277, each which are incorporated by reference in their entireties. Each of the media, which can be preformed media, can include a plurality of layers, as disclosed in the U.S. Patents listed above. Fiber/film support 440 supports the plurality of fibers/films 430 in a vertical configuration and may be made from a material such as polyurethane or a similar material. Either whole blood or RBCs flow through media 420 leukoreduction process.

Method 10 shows that leukoreduction filter 400 or the process of leukoreducing can optionally occur at whole blood stage or after RBCs have been separated from the plasma and platelets, before oxygen and carbon dioxide have been removed or after oxygen and/or carbon dioxide depletion in OCDD. In either case, leukoreduction can occur before storage of RBCs in a blood storage bag 200.

The benefits of leukoreduction are several. Leukoreduction may reduce the likelihood of fever in recipients, enhance RBC storage characteristics and reduce the transmission of viruses contained in leukocytes. Leukocytes in blood products can cause immunosuppressive effects and can pre-dispose recipients to an increased risk of infections, and may serve as vehicles of pathogen transmissions. Leukoreduction may reduce RBC storage lesions, reduce primary alloimmunization and reduce the total number of transfusion reactions in a recipient. By removing leukocytes from the RBCs before storage in storage bag 200, the deleterious effects of leukocytes highlighted above can be avoided and the quality of stored RBCs may be thereby increased or enhanced.

Oxygen/Carbon Dioxide Removal

Figure 5:
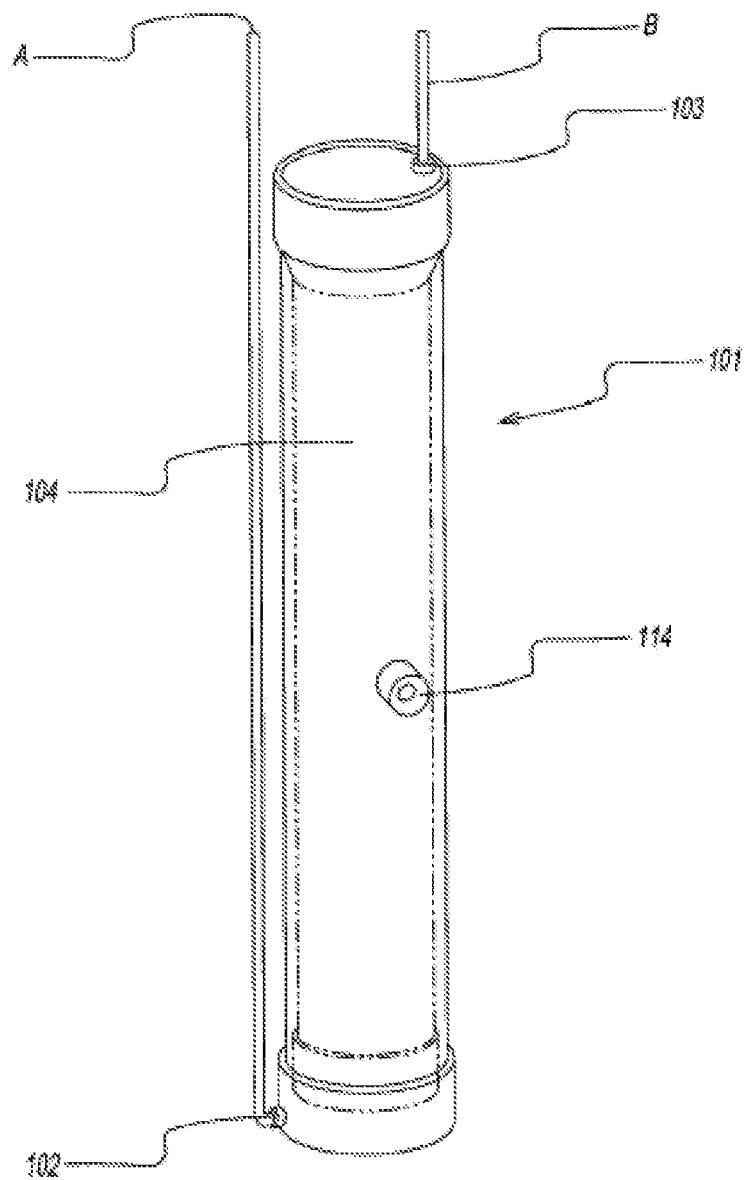
FIG. 5 illustrates a pre-storage oxygen, carbon dioxide oxygen and carbon dioxide depletion device of the present disclosure.
Figure 6:
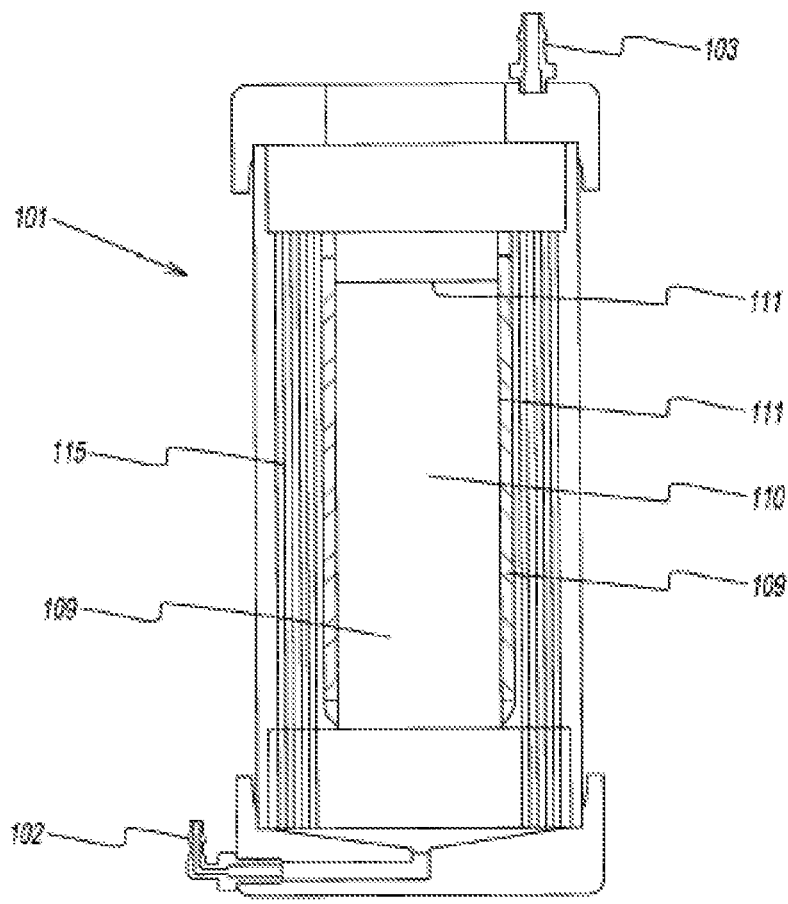
FIG. 6 illustrates a cross-section view of the depletion device of the device of FIG. 5.

In some aspects according to the present disclosure, RBCs may be treated to remove oxygen, carbon dioxide or oxygen and carbon dioxide in OCDD 101, as shown in FIGS. 2, 5 and 6. OCDD 101 may have a housing 104, an inlet port 102 and an exit port 103, through which RBCs enter and exit OCDD 101, respectively. OCDD 101 of FIG. 6 represents one embodiment of OCDD and contains an oxygen sorbent 110 at core 109. OCDD 101 may alternatively contain a carbon dioxide sorbent or a combination of oxygen and carbon dioxide sorbent. OCDD 101 may be comprised of a disposable housing having a series of hollow fibers and/or gas-permeable films or fibers 115 (or membranes) that are oxygen, carbon dioxide, or oxygen and carbon dioxide permeable. Optionally, housing 104 also has a vent 114 for air to enter when draining the device after completing the depletion process to allow maximal RBC recovery.

O/CD sorbent 110 may be a mixture of non-toxic inorganic and/or organic salts and ferrous iron or other materials with high reactivity toward oxygen, carbon dioxide, or oxygen and carbon dioxide. O/CD sorbent 110 may be made from particles that have significant reaction capacity for $O_2$ (e.g., more than 5 ml $O_2$/g) and can maintain the inside of OCDD 101 less than, e.g., 0.01% which corresponds to $pO_2$ less than 0.08 mmHg. O/CD sorbent 110 may be either free or contained in an oxygen permeable enclosure, container, envelope, etc. For example, oxygen scavengers and carbon dioxide scavengers are provided by Multisorb Technologies (Buffalo, N.Y.), or MGC (New York, N.Y.). Oxygen sorbents may exhibit a secondary functionality of carbon dioxide scavenging. Carbon dioxide scavengers include metal oxides and metal hydroxides. Metal oxides react with water to produce metal hydroxides. The metal hydroxide reacts with carbon dioxide to form water and a metal carbonate. Such materials can be blended to a desired ratio to achieve desired results.

In certain aspects, OCDD 101 of the present disclosure is configured to throughput and deplete approximately 100 mL of oxygen from a unit of blood. Alternatively, after passage of RBCs through OCDD, the oxygen saturation levels are reduced to less than 3 Torr in the RBCs. Alternatively, carbon dioxide levels are depleted in the RBCs to levels of approximately 10 Torr.

Again referring to FIGS. 5 and 6, hollow fibers and/or gas-permeable films or fibers 115 may be constructed as membranes in a flat sheet form. Hollow fibers and/or gas-permeable films or fibers 115 may be non-porous materials that are capable of high O/CD permeability rates (polyolefins, silicones, epoxies, polyesters etc) and membrane are hydrophobic porous structures. These may be constructed of polymers (polyolefins, Teflon, PVDF, polysulfone) or inorganic materials (ceramics).

Figure 7A:
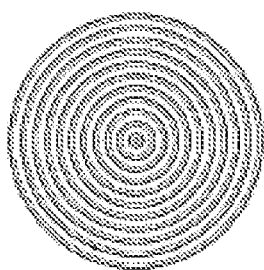
FIGS. 7A through 7D illustrate cross-section views of embodiments of depletion devices.
Figure 7B:
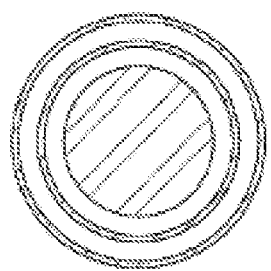
Figure 7C:
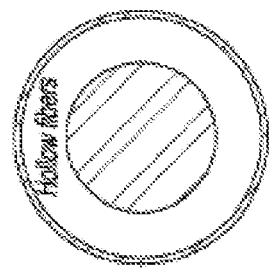
Figure 7D:
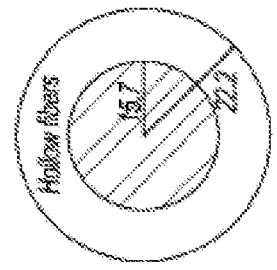

Referring to FIGS. 7B through 7D, alternative OCDD configurations (cross sectional views) are shown, with alternating sorbent 110 with hollow fibers 115 (embodiment of FIG. 6 is represented in FIG. 7A). In the embodiment of FIG. 6 and FIG. 7A, the characteristic diffusion time of oxygen is approximately 7.5 seconds. The placement of sorbent material relative to hollow fibers is critical because the diffusion time is proportional to the inverse square of distance from sorbent to the fiber. If the distance between the sorbent and fiber is reduced by one half the diffusion time is reduced by one quarter.

TABLE 2

| Example Specification | Eternal Gas Pathways | Eternal Gas Pathways |
|---|---|---|
| Example Serial #: | Device 70 | |
| Fiber Type: | Celgard 200/150-66FPI | Celgard 200/150-66FPI |
| Number of Fibers/unit: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |
| Active Fiber Surface Area (m$^2$): | 0.4084 | 0.8796 |

In the oxygen/carbon dioxide depletion devices disclosed herein, a plurality of gas permeable films/membranes may be substituted for the plurality of hollow fibers/films. The films and fibers may be packed in any suitable configuration within the cartridge, such as linear or longitudinal, spiral, or coil, so long as they can receive and convey red blood cells.

The lowest oxygen saturation is achieved using devices in which the sorbent is placed close to fibers to enable rapid diffusion time. Additional factors that increase oxygen and/ or carbon dioxide diffusion are larger active surface area of fibers exposed to sorbent materials.

Figure 8:
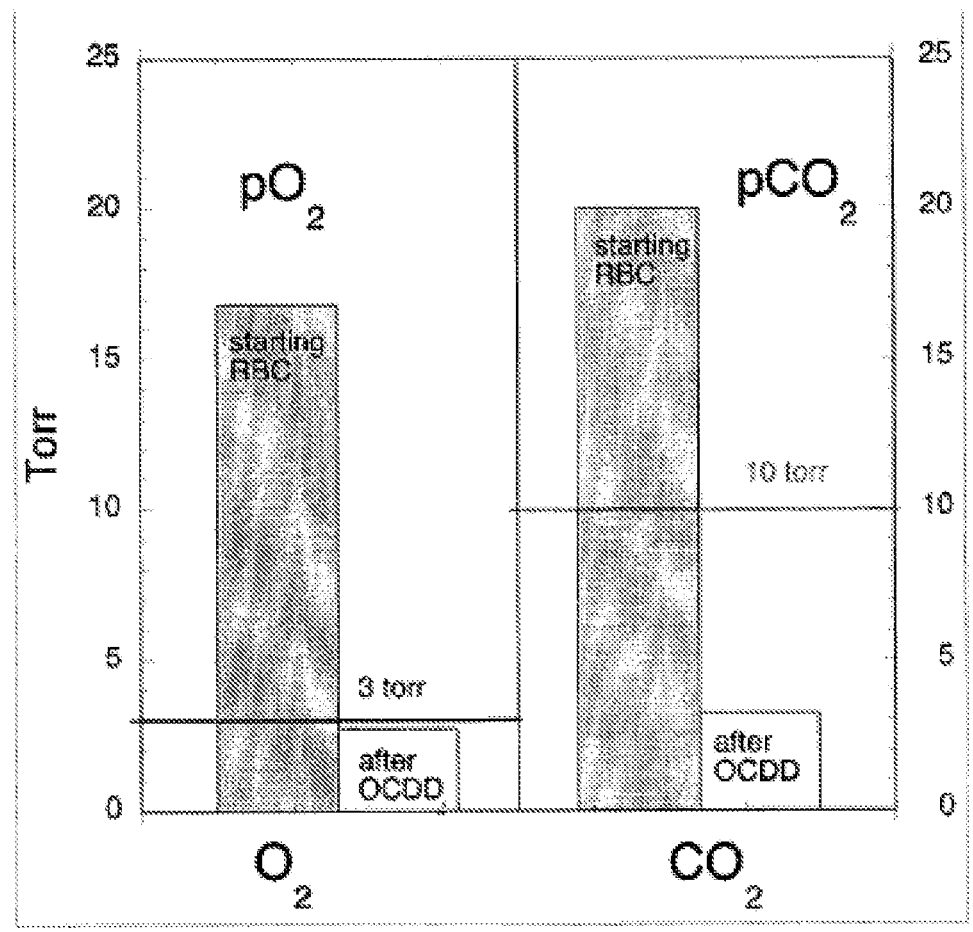
FIG. 8 illustrates the starting and ending partial pressures of oxygen and carbon dioxide, respectively, in red blood cells.

Referring to FIG. 5 and FIG. 8, the graph shows the effect of OCDD 101 on the partial pressure of RBCs that pass therethrough. At point A, prior to entry in OCDD 101, the partial pressure of oxygen in the RBCs is 16.8 Torr and at point B, the partial pressure of oxygen in the after oxygen and carbon dioxide depletion device is approximately 3 Torr. The partial pressure of carbon dioxide is approximately 20 Torr at point A and the partial pressure after RBCs pass through OCDD is approximately 3 Torr.

Figure 9:
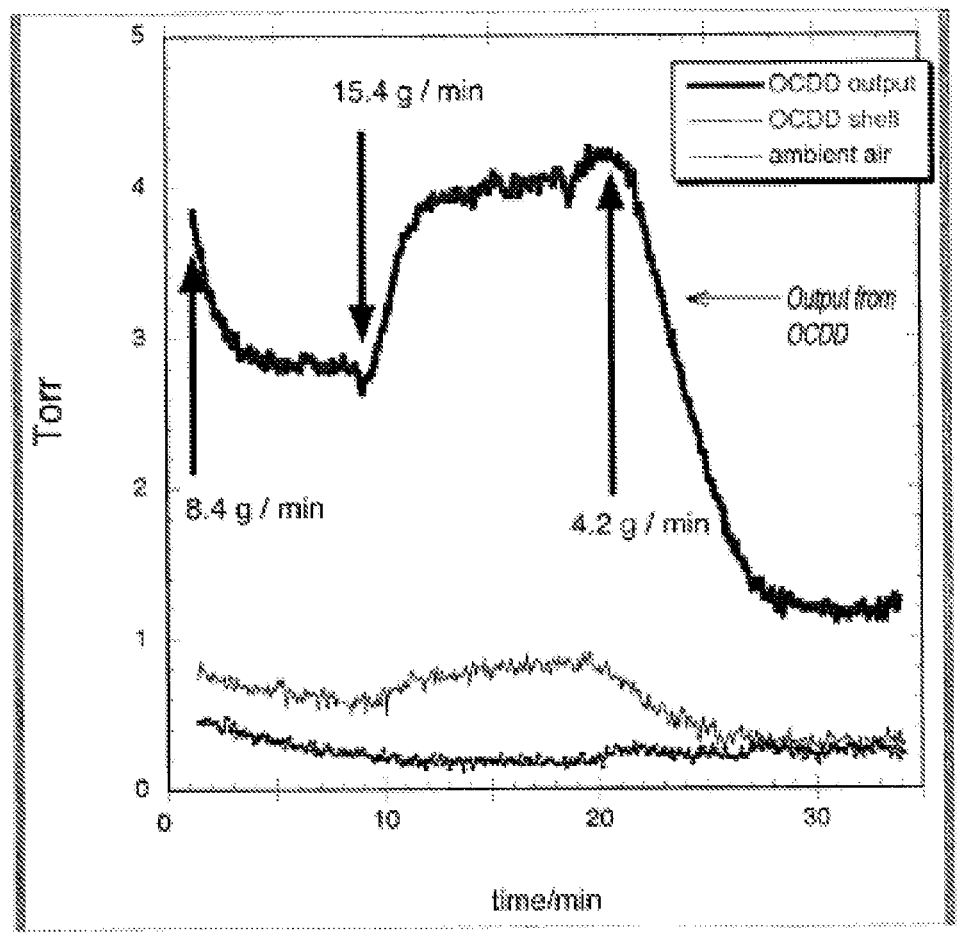
FIG. 9 illustrates the ending partial pressure of oxygen in RBCs as a function of flow rate of RBCs and how depletion varies according to flow rate of RBCs when device similar to FIG. 5 was fed with RBC suspension of 16.5 Torr.

FIG. 9 shows the partial pressure of oxygen in RBCs as a function of mass flow rate of the RBCs through OCDD 101. The partial pressure of oxygen in the gas surrounding hollow fiber as measured from the vent port 114 ranges from 1 to 0.5 Torr depending on the flow rate of the RBCs therethrough. FIG. 8 reveals the oxygen depletion that is provided by OCDD 101. The oxygen sensor at the outlet is enclosed in a bag flushed with nitrogen gas to increase the sensitivity of the pO$_2$ measurement of blood; pO$_2$ surrounding the sensor is shown as 'ambient air' in FIG. 9.

The OCDD functions to deplete oxygen from RBCs from oxy-hemoglobin because more than 99% of such oxygen is hemoglobin-bound in venous blood. Preferably, the degree of oxygen saturation is to be reduced to less than 3 Torr within 48 hours of blood collection. The oxygen depletion is preferably accomplished at room temperature. The affinity of oxygen to hemoglobin is highly dependent on the temperature, with a partial pressure of 26 Torr at 37° C. dropping to ~4 Torr at 4° C. Furthermore, this increase in O$_2$ affinity (K$_a$ hemoglobin-oxygen binding constant) is mainly due to reduction in O$_2$ release rate (k$_{off}$), resulting in an impractically low rate of oxygen removal once RBC is cooled to 4° C. Thus, it places a constraint on oxygen stripping such that it may be preferable to accomplish it before RBC are cooled to storage temperatures of 1° C. to 6° C.

As an alternative to or in addition to oxygen depletion, carbon dioxide depletion has the beneficial effect of elevating DPG levels in red blood cells. Carbon dioxide exists inside RBCs and in plasma in equilibrium with HCO$_3^-$ ion (carbonic acid). Carbon dioxide is mainly dissolved in RBC/plasma mixture as carbonic acid and rapid equilibrium between CO$_2$ and carbonic acid is maintained by carbonic anhydrase inside RBC. Carbon dioxide is freely permeable through RBC membrane, while HCO$_3^-$ inside RBC and plasma is rapidly equilibrated by anion exchanger (band 3) protein. When CO$_2$ is removed from RBC suspension, it results in the known alkalization of RBC interior and suspending medium. This results from removal of HCO$_3^-$ inside and outside RBC; cytosolic HCO$_3^-$ is converted to CO$_2$ by carbonic anhydrase and removed, while plasma HCO$_3^-$ is removed via anion exchange inside RBC. Higher pH inside RBC is known to enhance the rate of glycolysis and thereby increasing ATP and DPG levels. ATP levels are higher in Ar/CO$_2$ (p<0.0001). DPG was maintained beyond 2 weeks in the Argon purged arm only (p<0.0001). Enhanced glycolysis rate is also predicted by dis-inhibition of key glycolytic enzymes via metabolic modulation and sequesterization of cytosolic-free DPG upon deoxygenation of hemoglobin as a result of anaerobic condition. DPG was lost at the same rate in both control and Ar/CO$_2$ arms (p=0.6) despite thorough deoxygenation of hemoglobin, while very high levels of ATP were achieved with OFAS3 additive.

By depleting carbon dioxide in the OCDD, the pH of RBCs in cytosol is increased. Further, 2, 3-DPG levels are increased for the first 3 weeks of storage and ATP level is maintained at high levels. These factors enhance the viability of RBCs prior to being stored at oxygen depleted storage in Phase B.

Figure 10:
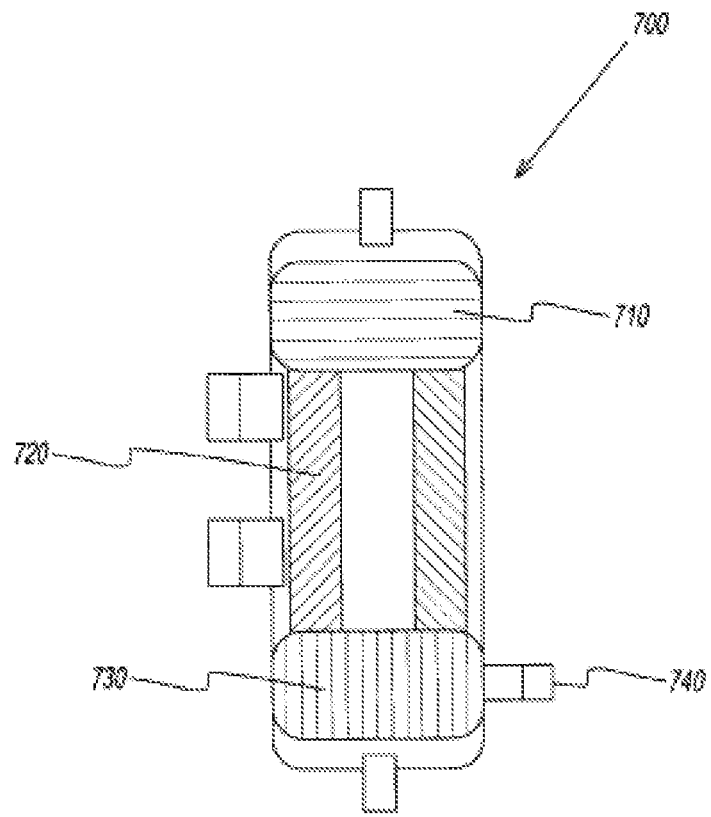
FIG. 10 illustrates alternative oxygen/carbon dioxide depletion device incorporating leukoreduction and plasma separation components.

Referring to FIG. 10, a further embodiment of OCDD device 750 is shown, in which flow of oxygen free gas or oxygen free gas with carbon dioxide through the body of the device (two ports protruding on the left side of cylinder) can be used to combination with a leukoreduction filter 710, OCDD 720, a plasma separator 730. Multifunction OCDD 750 eliminates the need for centrifugation of the whole blood, received from donor 15, which is currently a necessity by using a centrifuge. By combining these three devices into a single device, the need for a separate centrifuge, a highly costly and cumbersome device, is eliminated. Plasma flows through port 740 to a further collection bag for further processing. Accordingly, in this embodiment, whole blood can be collected from a donor, leukocytes can be removed, oxygen and or carbon dioxide can be removed and plasma and platelets can be removed to pass RBCs through device. The RBCs are then deposited into collection bag 200 after additive solution is added through the device for storage or transfusion to a recipient. Multifunction OCDD 750 as part of collection system 10 and system 100 permit rapid transformation of whole blood to stored RBCs for immediate storage or transfusion to a recipient.

Editing

Before oxygen and/or carbon dioxide are removed from the RBCs, the whole blood or RBCs may be edited. Editing RBCs is the process of identifying and removing blood cells that have a poor likelihood of surviving the transfusion process or will likely die shortly after transfusion. Editing moribund RBCs, or dead or dying red blood cells, may be employed by using, for example, a filter-like editing device 500. Editing can occur at various times during the storage process, e.g., as shown in FIG. 1. For example, editing can occur with whole blood or RBCs, before being O/CD depleted and prior to storage in an anaerobic storage environment. While FIG. 1 shows the editing step being performed by editing device before oxygen and or carbon dioxide have been removed, editing can alternatively be performed at different stages of the storage process. For example, editing can be performed immediately before transfusion after storage in storage bag 200.

Editing can be important because a leading cause of morbidity and mortality to transfused patients is the non-viable portion of the blood that is transfused independent of any pathogen transmission. RBCs that are compromised or that will be removed by the spleen by the reticuloendothelial system shortly after transfusion may threaten to overwhelm the already compromised recipient. Up to 25% of transfused cells are removed by recipient in the first twenty four hours after transfusion. These removed cells are harmful because they contribute immediately to the excess iron burden of the recipient, which may be a critical parameter for chronically or massively transfused patients. Also, these cells may cause capillary blockage due to reduced deformability or aggregate formation, leading to poor tissue perfusion and even organ failure. Thus, substantial benefits are expected if one can remove these less viable RBCs prior to transfusion.

There are several techniques that may be used to edit the red blood cells. The first technique is a centrifugation process to separate old and young RBCs before storage based on characteristic buoyancies of young and old RBCs.

A second technique applies a biomechanical stress, such as an osmotic shock, to hemolyze weak cells before or after storage in combination with a buffer exchange step. The applied biomechanical stress immediately identifies those cells that are weak to rapidly contrast with the stronger RBCS to enable mechanical separation. The weak RBCs are those that contribute to recipient morbidity and mortality, particularly, with individuals with already compromised or overloaded immune systems. Up to 25% of RBCs that arrive to a recipient are already dead and can have deleterious effects on the recipient. By editing the RBCs, that number can be reduce by 50% to 75%.

A third technique applies to the deformability of the RBCs. Bump array microfluidic devices containing staggered pillars (Huang, L. R., et al., "Continuous particle separation through deterministic lateral displacement,". Science 304(5673): 987-90 (2004) herein incorporated by reference in its entirety), allow deformable RBCs to pass through the pillars while deformable RBCs can not pass through the pillars and are bumped into separate channels.

A further technique for editing the RBCs uses a filter system to remove RBC exhibiting a specific surface marker. RBCs exhibiting known surface markers such as phosphatidiyserine or aggregated protein 3 can be trapped by a filter surface modified with high affinity ligand (e.g., Annexin IV or antibodies against specific surface marker protein).

An additional technique uses the same high affinity ligands in the second technique, conjugated to make a multimeric molecule such that RBCs exhibiting target surface markers forms aggregate. This can then separated by filtration or centrifugation.

Irradiation

A further processing step that RBCs may be subjected to is irradiation, e.g., by either gamma or X-ray radiation. Irradiation of RBCs is of significance to avoid transfusion related complications. Transfusion-associated graft-versus-host disease (TA-GVHD) is a rare but nearly always fatal complication associated with transfusion therapy in severely immuno-compromised blood recipients (for example, bone marrow transplant recipient, patients receiving aggressive chemotherapy, premature neonates). Prevention of TA-GVHD requires complete removal of, or cessation of the proliferative potential of T-lymphocytes from donor blood. For instance, leukoreduction filters are not adequate in prevention of TA-GVHD because leukoreduction filters may not completely eliminate lymphocytes. Thus, lymphocyte inactivation by X-/gamma-irradiation may be preferred for TA-GVHD prevention.

Gamma-irradiation abrogates proliferation of T-lymphocytes by damaging the DNA directly and via reactive oxygen species (ROS), namely hydroxyl radicals produced during gamma-radiolysis of water. Although RBCs do not contain DNA, ROS generated by gamma-irradiation have been shown to cause significant damage to the RBCs. The major damage observed includes: i) increased hemolysis; ii) increased K+ leak; iii) reduction in post-transfusion survival; and iv) reduced deformability. Such damage is similar to, but an exaggerated form of, storage-induced damage of RBC. The compromised status of RBC is well known to the physicians who administer such compromised RBCs, and FDA mandates restricted use of such RBCs in terms of shortened shelf life after gamma-irradiation (14 days) and/or 28 days total shelf life for irradiated units.

The irradiation of blood components has received increased attention due to increasing categories of patients eligible to receive such blood to prevent transfusion-associated graft versus host disease. However, irradiation also leads to enhancement of storage lesions, which could have deleterious effects when such blood is transfused. It is well known in the field that the main deleterious side-effect of radiation on RBC is oxidative damage caused by ROS.

Radiation damage to RBC in the presence of oxygen can occur in two ways;
 i) By ROS generated during and immediately after irradiation. ROS can attack proteins and lipids in vicinity, as well as to initiate peroxidation cycle of lipid and protein using oxygen to fuel.
 ii) Met-Hb and its denaturation products generated in i) above act as catalysts to further cause ROS-mediated oxidative damage during subsequent refrigerated storage of RBC. This is an enhanced version of storage lesion development using $O_2$.

ROS is a major culprit in causing deterioration of RBCs during refrigerated storage at blood banks Storing RBCs under anaerobic conditions significantly reduces such damages caused by ROS. Accordingly, deleterious or negative effects of gamma- and X-ray irradiation steps to RBCs, are substantially offset by the protective benefits oxygen and/or carbon dioxide removal and the subsequent anaerobic storage. Therefore, irradiation of RBCs is preferably performed after oxygen removal in OCDD 100 of FIG. 2. Additionally, gamma irradiation and X-ray irradiation can occur when RBCs are stored in storage bag 200 or subsequent to storage prior to oxygen addition before transfusion.

While oxygen, carbon dioxide or oxygen and carbon dioxide removal take place before irradiation, if irradiation occurs before oxygen removal (FIG. 1), oxygen removal should take place within twenty four hours thereafter to limit effects of on RBCs.

Pathogen Inactivation

After RBCs have been collected, treatment for the removal of infectious agents that may be present in donor blood and potentially passed to recipient 50 receiving transfusions, may be effected. Infectious agents include microorganisms such as viruses, especially retroviruses, bacteria, fungi and non-microbial agents such as self-replicating proteins (prions) and nucleic acids. A process called pathogen inactivation or reduction removes such dangerous infectious agents from the RBCs. However, the chemical processes of pathogen inactivation or reduction are also potentially damaging to the RBCs.

A pathogen inactivation process may involve chemical and light or riboflavin and light therapy. In an aspect, pathogen inactivation or reduction may be performed before storage in the anaerobic storage environment for whole blood, and for RBCs that have been separated from whole blood, before passage through OCDD or after passage through OCDD and before storage.

Since RBCs are stored in an anaerobic environment, growth of aerobic bacteria and parasites are prevented. Bacteria such as Yersinia enterocolotica, Serratia liquefaciencs and Staphylococcus strains are anaerobic and require oxygen for growth and multiplication. Parasites such as Plasmodium falciparum (malaria protozoan), babsea (babesiosis) and Trypanosoma cruzi (Chagas disease) are documented infections in the US following blood donations. These microaeophilic organisms and are exposed to varying oxygen concentrations during their life cycle. They survive well in reduced oxygen environments, but may not adapt to the anaerobic conditions developed during RBC storage.

Due to the reduction of ROS production under anaerobic state, gamma or X-ray may be used at increased dosage and/or time compared to T cell inactivation for pathogen inactivation.

Blood Storage Bag

Figure 11A:
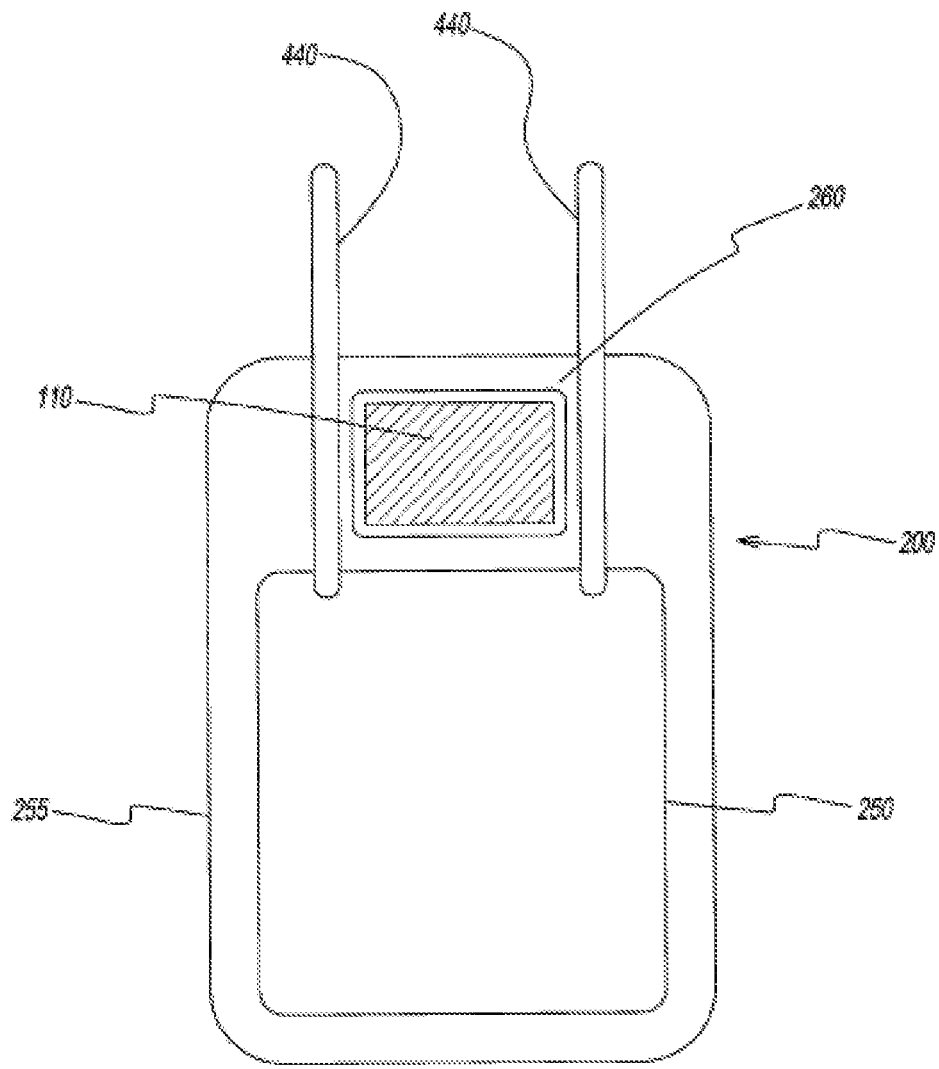
FIGS. 11a and 11b illustrate alternative blood bags according to the present disclosure.

Referring to FIGS. 2 and 11a, a blood storage bag 200 according to an embodiment of the present disclosure is provided. Blood bag 200 has an inner blood-compatible bag 250 (preferably polyvinyl chloride (PVC)), and an outer barrier film bag 255. The material of bag 250 is compatible with RBCs. Disposed between inner bag 250 and outer oxygen barrier film bag 255 is a pocket that contains a sorbent 110. Barrier film bag 255 is laminated to the entire surface of inner bag 250. Sorbent 110 is contained in a sachet 260, which is alternately referred to as a container, enclosure, envelope, pouch, pocket, etc. Sorbent 110 is optimally located between tubing 440 that leads into and from bag 200 and port 415, and specifically between inner bag and outer oxygen barrier film bag 255. This location will ensure that oxygen disposed between these two bags will be scavenged or absorbed. Sorbent is ideally located in a sachet 260 and not in contact with RBCs. Sorbent may include oxygen sorbents, and may also be combined with carbon dioxide sorbents, enabling sorbent 110 to deplete both oxygen and carbon dioxide at the same time.

Figure 11B:
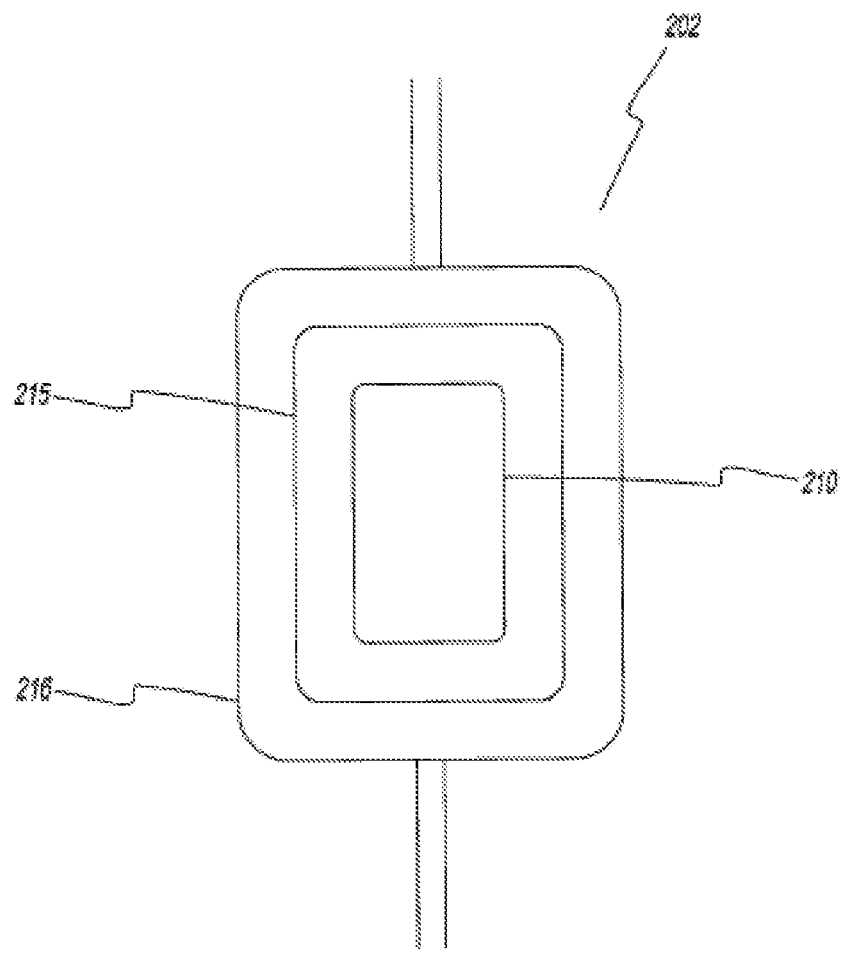

Referring to FIG. 11b, storage bag 202, is similar to bag 200; however, bag 202 is a laminated bag. Bag 202 has an inner PVC blood bag 210, an outer barrier bag 216, and a sorbent layer 215 between blood bag 210 and outer barrier bag 216.

Figure 12A:
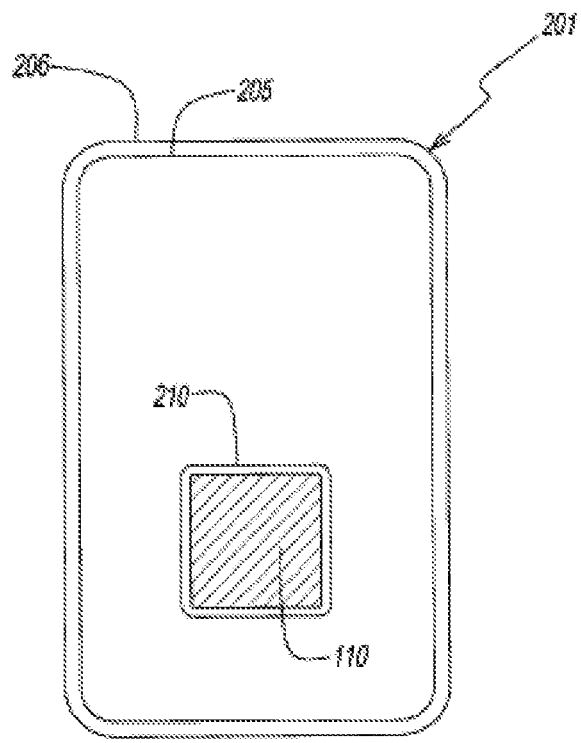
FIGS. 12A through 12B illustrate embodiments of a blood storage bag according to the present disclosure.

In FIG. 12A, a small sachet 210 contains sorbent 110. Small sachet 210 is enclosed inside of PVC bag 205 and is preferably made from a silicone or siloxane material with high oxygen permeability of biocompatible material. Sachet 210 has a wall thickness of less than 0.13 mm thickness ensures that $O_2$ permeability ceases to become the rate-limiting step. PVC bag 205 may also contain carbon dioxide sorbent. Again, sorbent 110 may be an oxygen, carbon dioxide and oxygen and carbon dioxide sorbent.

Figure 12B:
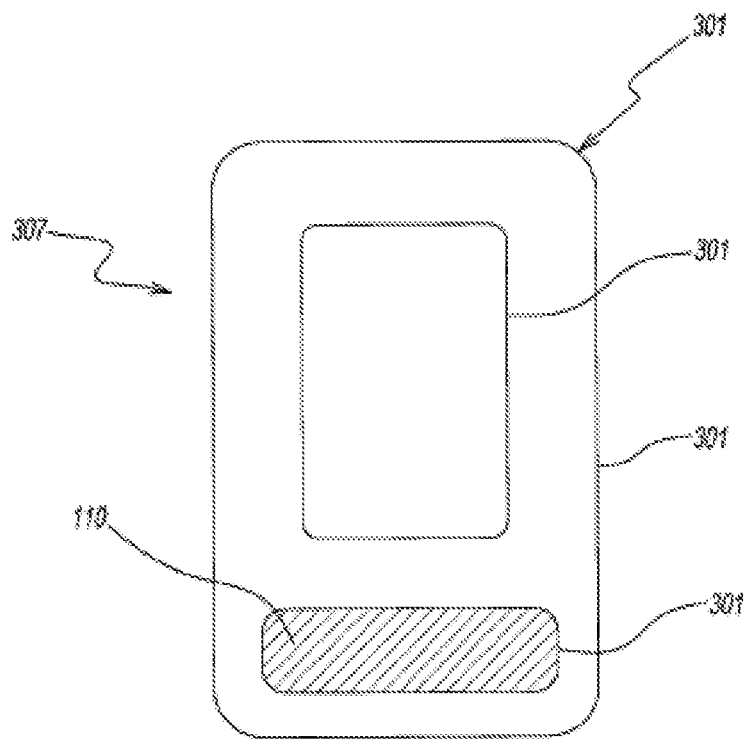

In FIG. 12B, RBCs are stored in storage bag 307 that has a secondary bag 301 in order to maintain an anaerobic storage environment for RBC storage. Secondary bag 301 may have a transparent oxygen barrier films (e.g., nylon polymer) that compensate for the inability of PVC blood bag 305 operate as a sufficient oxygen barrier to maintain RBCs in an anaerobic state. Secondary bag 301 may be made with an oxygen barrier film, preferably a nylon polymer or other transparent, flexible film with low oxygen permeability. Bag 307 contains a sorbent sachet 310 containing a sorbent 110 that is an oxygen, carbon dioxide or oxygen and carbon dioxide sorbent.

Referring to FIGS. 12A and 12B, blood storage bags 201 and 301 are configured to store RBCs for extended storage periods of time in an anaerobic storage environment. Inner blood storage bags 205 and 305 are preferably made from DEHP-plasticized PVC and are in contact with RBCs. DEHP-plasticized PVC is approximately 200 fold less permeable to oxygen compared to silicone. Inner storage bags can also be made from non DEHP plasticized PVC or other non DEHP plasticized polymer. DEHP has a protective effect on the RBC membrane, but this effect is unnecessary when the RBCs are stored anaerobically.

However, PVC is insufficient as an oxygen barrier to maintain the anaerobic state of RBCs throughout the storage duration. Therefore, blood storage bags 201 and 301 may be fabricated with outer transparent oxygen barrier film 206, 306 (e.g. nylon polymer, aluminum oxide coated nylon etc.) laminated to the outer surface inner blood bag 205 and 305. This approach, as well as one shown in FIG. 1, uses accepted plastic materials for blood contact surface (for case of DEHP/PVC, supplying DEHP for cell stabilization) at the same time prevents oxygen entry into the bag during extended storage.

Alternatively, transparent organic oxygen sorbent film may be laminated between 205/206 or 305/306 in place of 210/110 or 310.

OCDD 101 and various storage bags of the present disclosure can be used in varying combinations. For example, OCDD 101 of FIG. 1 can be used with blood bag of FIG. 11, 11b, 12A or 12B. Other combinations and configurations are fully within the scope of the present disclosure.

During storage in bag 200 different components may be added to RBCs stored anaerobically and during carbon dioxide depletion. In addition to additives, metabolic supplements may also be added to red blood cells. Metabolic supplements can be provided to RBCs specified times and rates or frequencies by a metering device placed within the main storage bag, or added through pre-connected PVC bags. Metabolic supplements are added to RBCs during storage at 4° C. Red blood cell storage extends well beyond the current 6-week limit for 12 or up to 20 weeks at 4° C., with levels of 2-3 DPG and ATP that are above those found in freshly drawn blood. The metabolic supplement includes pyruvate, inosine, adenine, and optionally dibasic sodium phosphate and/or monobasic sodium phosphate. Additionally, nutrient supplementation may optionally include supplements that provide antioxidants to the storage medium, including, but not limited to analogues of reduced glutathione, vitamin C and vitamin E. Current refrigeration storage technology is essentially a premature aging process of RBCs in contrast to the metabolism protection system of the present disclosure. Current refrigerated storage of red blood cells does not maintain appropriate cellular glutathione levels. Glutathione supplementation may extend the storage time of RBCs. The amounts and timing of glutathione supplementation may conveniently be determined and optimized as necessary.

Figure 13:
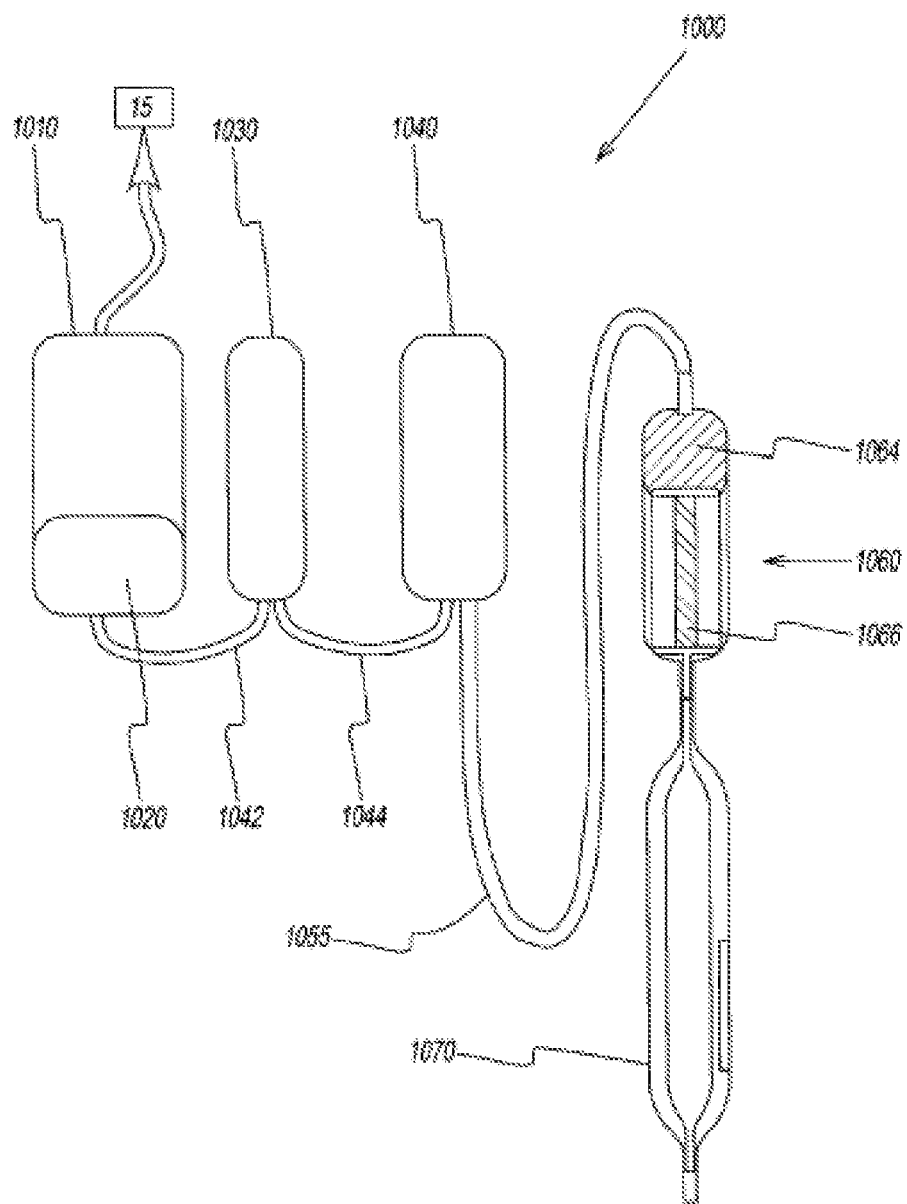
FIG. 13 illustrates an alternative configuration according to the present disclosure.
Figure 14:
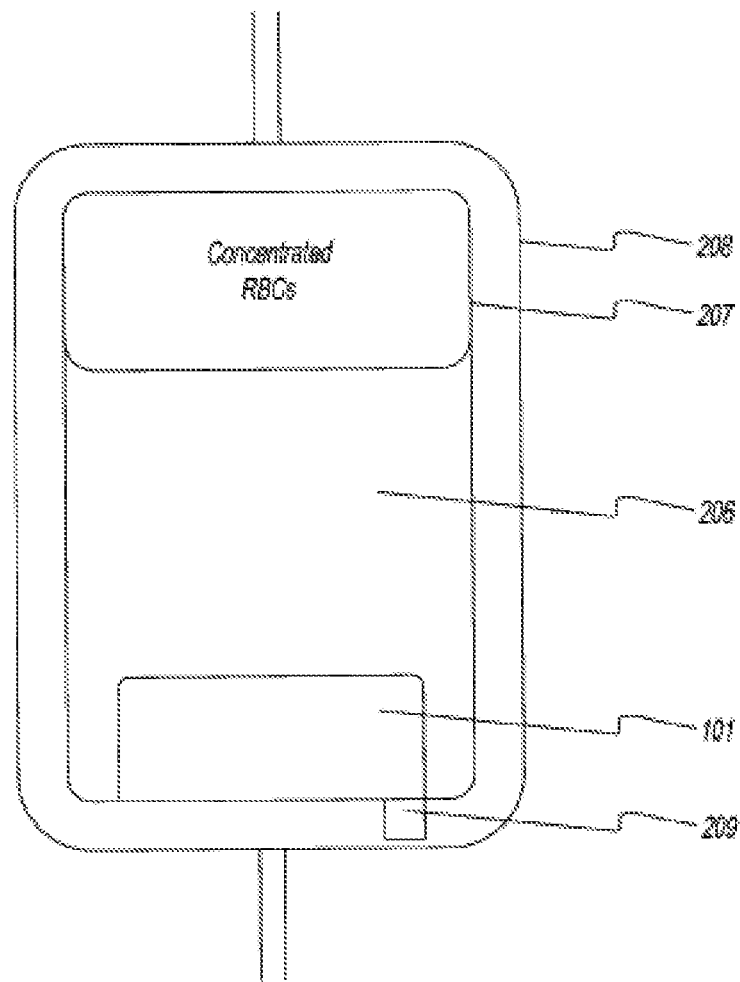
FIG. 14 illustrates an aspect for volume reduction.

Referring to the drawings and in particular to FIG. 13, another embodiment of a disposable blood anaerobic storage system is shown and referenced using reference numeral 1000. The blood storage system includes a blood collection bag 1010, a combination oxygen/carbon dioxide depletion device 1060 that includes a leukoreduction filter 1064 and a oxygen and/or carbon dioxide depletion portion 1066, and an anaerobic blood storage bag 1070. System 1000 also includes a collection bag 1030 for liquid plasma and/or platelets. Combination OCDD 1060 not only removes oxygen and carbon dioxide from red blood cells traveling therethrough, but also filters excessive white blood cells from the red blood cells. This embodiment of FIG. 14 offers a single-use, disposable, low cost system. Tubing connects the various components of the blood storage system 1000. Tube 1042 connection bag 1010 connects collection bag 1010 and bag 1030 and tubing 1044 connects bag 1030 and bag 1040. Tube 1055 cnnects combination OCDD 580 with additive bag 1040.

In certain embodiments of the present disclosure, the system recognizes that blood cells in storage continue to metabolize. It is desirable to reduce their metabolic rate as low as possible over time of storage, and yet maintain healthy viable cells that are of high quality for transfusion. In an embodiment, the present disclosure uniquely protects essential metabolism, prolongs the shelf life of refrigerated erythrocytes, and provides high quality blood product. Further, refrigeration reversibly disables the enzymes essential for met-Hb reduction in vivo, increases the solubility of damaging $O_2$ (almost by a factor of 2) in the environment of the red blood cells, and permits the level of ATP to decrease by diminishing the glycolytic rate (at 4° C. the rate is about 1% of that found at 37° C.). Reduction of red cell ATP concentration results in echinocyte (i.e. an unstable form of red blood cells) formation, increased rates of membrane vesiculation, loss of red cell surface area, and accelerated sequestration by splenic macrophages. Vesiculation continues throughout the cold storage period, is exacerbated by echinocyte formation, and decreases red blood cell survival by decreasing red blood cell membrane area.

Oxygen removal can be conducted at any temperature that maintains good viability of the RBC. Preferably, oxygen is removed between about 1° C. and about 37° C. provided that RBC viability is maintained. Once in an embodiment of a blood storage device of the present disclosure, the RBC can be stored under refrigeration in the manner consistent with common industry practice for storage of blood products, preferably at a temperature between 1° C. and 10° C., and more preferably at about 4° C. Such storage periods range from about 6 to about 20 weeks and longer. Preferred storage periods are about 6 to about 15 weeks duration or longer provided RBC quality is maintained.

Pre-Transfusion

Prior to transfusion of stored RBCs to a patient or recipient, various processes can be affected to maximize acceptance of RBCs by the recipient and to optimize the condition of the RBCs.

In those patients who are either small or whose circulatory systems cannot process a great influx of RBCs, the volume of the RBCs must be reduced immediately prior to transfusion. Such patient who may face such an issue include those suffering from congestive heart failure or neonates. Volume reduction can be accomplished using a variety of methods.

When RBCs are stored for a length of time, the RBCs may generally be stored in a storage bag, such as bags of FIGS. 11a, 11b, 12A, and 12B. In some aspects, storage bags can have a hydrophilic membrane compartment in the top ½ of the bag, such as that of bag 208 of FIG. 14. In an aspect, bag 208 may have a hydrophilic membrane 207 having a membrane pore size must be less than $\sqrt[3]{4}$ micron to retain the RBCs cells and to prevent them from flowing through. When membrane 207 filled with a concentration of RBC with low hematocrit, plasma and additive solution will pass through the membrane into the lower compartment 206 concentrating RBCs in membrane 207. The top portion of the lower compartment needs a check valve 209 so the fluid will not escape during transfusion. Bag 208 may have a sorbent 101, as discussed above, for purposes of continued depletion of oxygen, carbon dioxide, and oxygen and/or carbon dioxide.

More conventionally, a portion of RBC of low hematocrit can flow into a small hollow fiber/film device having hydrophilic fibers/films, such as the fibers/films of OCCD 100. A portion of the RBC will flow into the fiber/film lumens and liquid and the liquid portion will pass through the fiber/film wall. A differential pressure across the fiber/film wall will be used to control RBC and fluid flow. This is another method of concentrating the RBCs in advance of transfusion.

Alternatively, RBCs may be concentrated by passage through several microfluidic chips that use the inertia of the RBCs. The microfliudic chips harness the inertia of the RBCs by forcing the RBCs to flow through a plurality of narrow channels such that only one cell is able to pass through each of the plurality of channels at a time. The cells are in the center of the channel, they exit through a center outlet port, and fluid, plasma and additives can exit in ports adjacent to the center port. The microfluidic chip may be scaled up for volumes. Microfluidic chips may contain at least one network unit disposed in a substrate. Microfluidic devices have an aspiration pressure to enables movement of RBCs through the network unit.

A further processing step that is necessary immediately prior to transfusion is the introduction of nitric oxide (NO) to the RBCs to enhance vasoregulatory function. There is increasing awareness that blood transfusion using banked blood is not only providing fully perceived benefits, but in some cases, harmful to some recipients. One of the major reasons behind lower-than-expected efficacy of transfused blood is postulated to be the loss of vasoregulatory function of RBC caused by degradation of nitric oxide (NO) sequestered in hemoglobin (Hb) molecules within RBC. A recent report showed that as short as 3 hours after blood collection, NO in RBC was lost, and its vasoregulatory activity can be restored with addition of NO replenishing compounds. Accordingly, the introduction of NO to RBCs during storage in blood bag 200, immediately prior to transfusion and after storage will assist the recipient in receiving optimal benefits from the transfusion. Because of increased stability of NO in anaerobic conditions, nitric oxide is added to the anaerobic environment of storage bag 200 prior to transfusion, for example. Additionally, NO can be added in the post-storage phase C prior to the addition of oxygen before transfusion. NO addition requires prior oxygen removal due to its inherent instability in the presence of oxygen. Additionally, NO must be added immediately before transfusion in the form of NO gas, NO precursor reagents, or nitrite. NO can be added to RBCs in storage bag 200 using a small bag or cartridge to inject above materials in form of a gas or nitrate or other precursor chemical as part of a transfusion set.

Immediately before transfusion, oxygen can be supplied to RBCs to oxygenate RBCs. Addition of oxygen must be accomplished during post-storage phase C after gamma and x-ray irradiation and nitric oxide addition, preferably immediately before transfusion at the bedside. The presence of oxygen with the processes of gamma and X-ray irradiation and the addition of nitric oxide are deleterious to the RBCs as discussed above.

The benefits of oxygen removal and or carbon dioxide removal from RBCs before storage in combination with and other therapies has a positive effect on the outcome of the stored RBCs in advance of transfusion.

Figure 15:
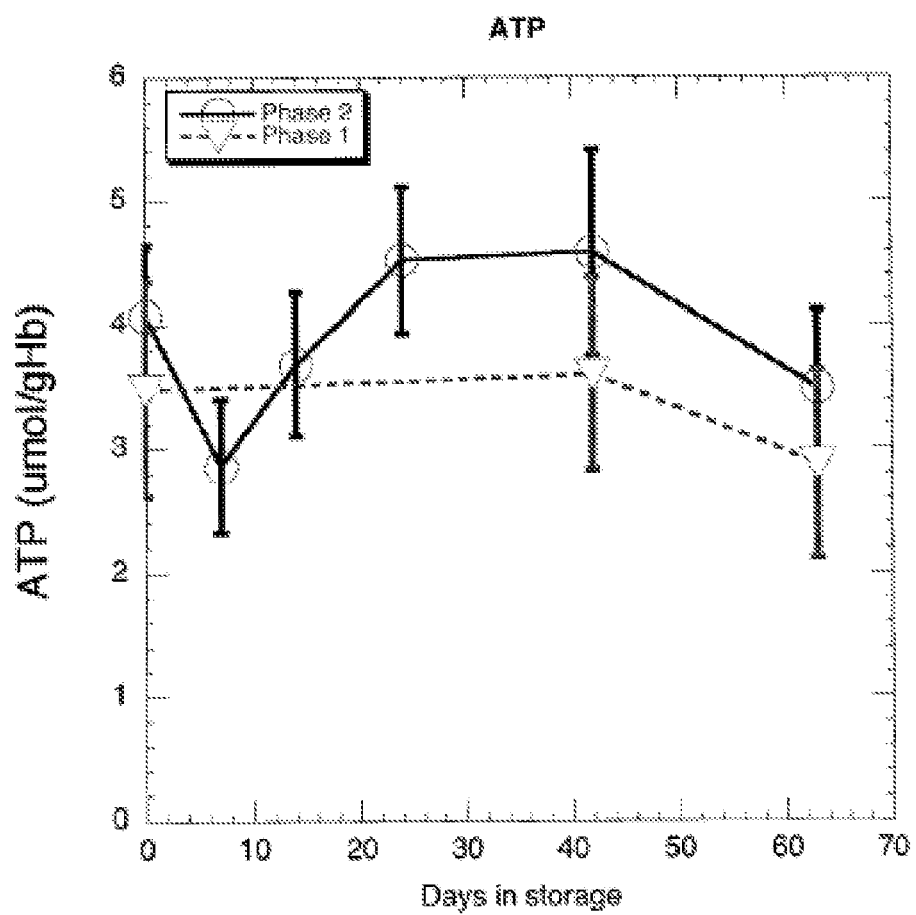
FIG. 15 illustrates a comparison of ATP of RBCs stored in accordance with the present disclosure.
Figure 16:
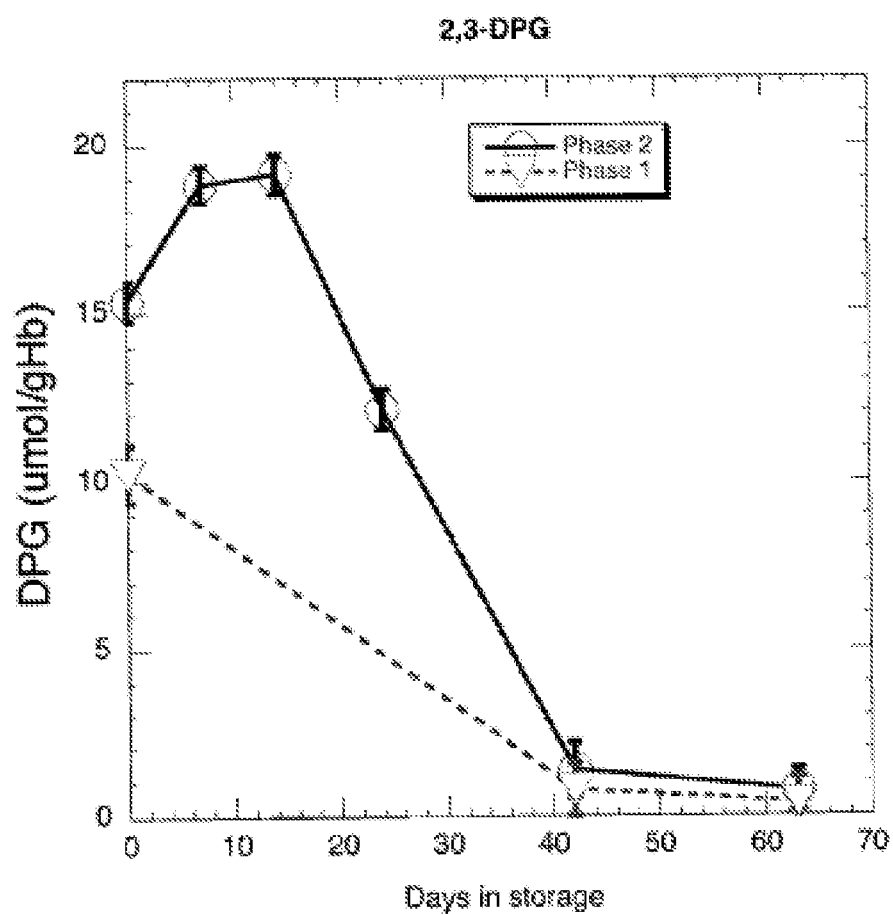
FIG. 16 illustrates a comparison of 2,3 DPG of RBCs stored in accordance with the present disclosure.
Figure 17:
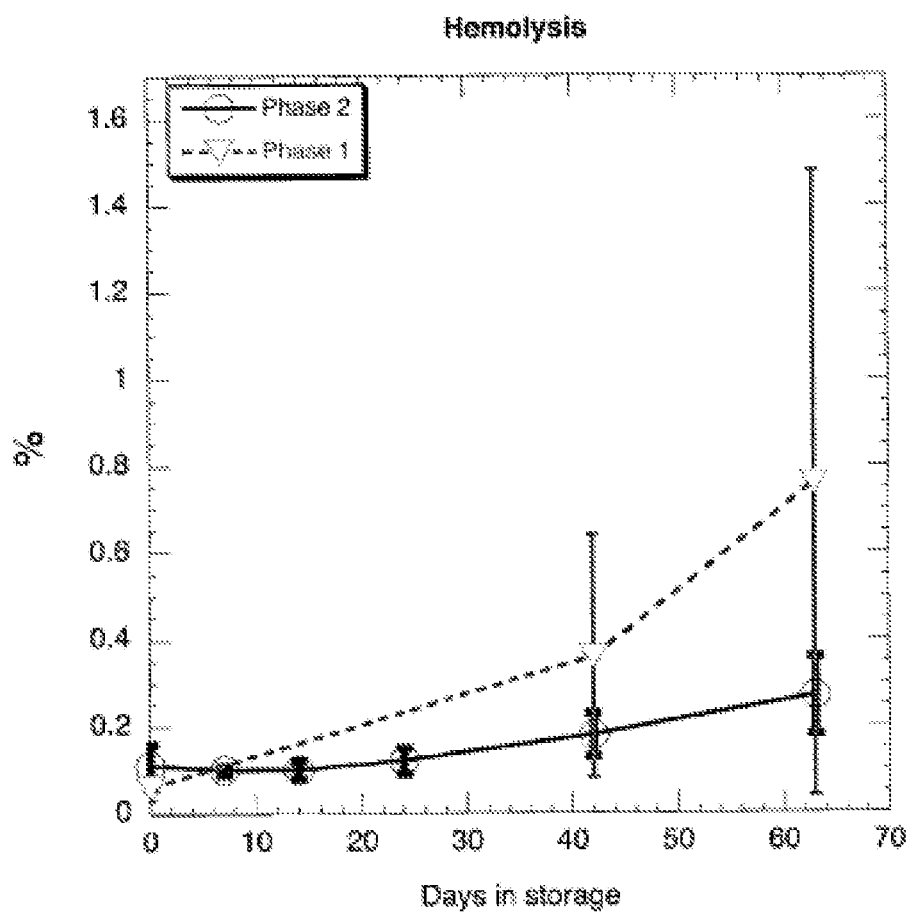
FIG. 17 illustrates a comparison of hemolysis of RBCs stored in accordance with the present disclosure.

FIGS. 15, 16 and 17 show the benefits offered by the proposed storage system and process of the present disclosure. In Phase I, represented by dotted line, RBCs are flushed with an inert gas to remove oxygen and are stored in an anaerobic canister for 9 weeks. In Phase 2, represented by solid line, RBCs are oxygen, carbon dioxide, or oxygen and carbon dioxide depleted in OCDD 100 and are stored in anaerobic storage bag 200 for 9 weeks. Phase 2 shows that ATP levels of RBCs are significantly higher at weeks 3 through 9. By maintaining high levels of ATP, RBCs maintain the ability of dilate the pre-capillary arteriole maintain a high metabolic level. Further, ATP can be boosted and significantly stimulated during the first four weeks of storage by initially depleting oxygen levels and maintaining carbon dioxide levels in the presence of a wide range of additives. FIG. 15 shows that the shelf-life of RBCs is substantially enhanced by reducing oxidative damage at 1-6° C. and maintaining high levels of ATP for an extended period.

FIG. 16 shows that under Phase 2 anaerobic conditions, 2,3 DPG is maintained at a high level by depleting carbon dioxide at the onset of storage. The transfusion of high 2,3 DPG blood with full oxygen carrying capacity comparable to fresh blood provides significant benefits to patients with critical and immediate oxygen needs. The rate at which 2,3, DPG declined after week 3 is typical.

Referring to FIG. 17, hemolysis is significantly lower during Phase 2 as compared to hemolysis during Phase 1. In particular, hemolysis is significantly lower at weeks 6 through 9 of storage. Hemolysis is a concern for all transfused patients and is particularly a concern for patients under chronic transfusion therapy. Patients with inherited hemoglobinopathies such as sickle cell disease (SCD), alpha- and beta-thalassemia, require repeated periodic transfusions of 30 or more units per year. These patients' RBCs have defective hemoglobin that does not function properly in gas transport, and often have RBCs of limited life span. These patients' own RBCs, together with RBCs from chronic transfusion therapy, can overload the body's capacity for iron. Long-term iron overload is highly toxic, and the complications that arise from it become a main source of morbidity unless patients are placed under continuous iron chelation therapy. One of the major sources of excess iron for chronically transfused patients is hemoglobin originating from non-viable RBCs (as a result of accumulated storage lesions) that are destroyed immediately after transfusion. By reducing the number of non-viable RBCs, anaerobic storage of RBCs with higher 24-hr recovery reduces addition of excess iron to these patients.

RBC storage life can be measured by the extent of vesicle formation, extent of hemolysis, and total cellular ATP levels. Long storage life is obtained when the tesicle formation is low, hemolysis is low and high ATP levels are sustained, preferably above about 2-3 .mu.mol ATP per g Hb. All of these parameters may be measured by the conventional methods known to those of skill in the art. For example, samples of cells can be assayed for the extent of hemolysis by calculating the fraction of supernatant hemoglobin relative to total hemoglobin. To measure ATP levels, for example, RBCs can be assayed for ATP according to the methods described in Technical Bulletins 336-W and 35— (Sigma Chemical Co., St. Louis, Mo.).

As used herein, improved or prolonged shelf life or improved storage of RBCs refers to the preservation of viable RBCs for an extended period of time relative to the current standard of about 6 weeks. In certain embodiments of the present disclosure, substantial oxygen removal provides RBCs with an extended storage life of about 7-15 weeks. In other embodiments according to the present disclosure, substantial oxygen removal provides RBCs with an extended storage life up to 20 weeks or greater, particularly when cells are suspended in the storage solutions provided by the present disclosure. In another aspect, substantial oxygen removal provides RBCs with an extended storage life of about 10-15 weeks. In other aspects, the extended storage life may be 10 to 20 weeks or 10 to 25 weeks. In a further aspect, storage life can be prolonged by preventing 2,3-DPG feedback inhibition of the RBC glycolytic pathway.

The in vitro parameters measured after storage of RBCs provide a means to measure in vivo survival of RBCs. The conventional means to assess in vivo survival is to determine the percentage of cell survival 24 hours post transfusion in a recipient. Typically in the USA, the average percentage of cell survival needs to be about or better than 75% to provide an acceptable RBC product. The three parameters, vesicle production, extent of hemolysis, and ATP levels, may be routinely used individually in the art to predict in vivo cell survival.

Figure 18:
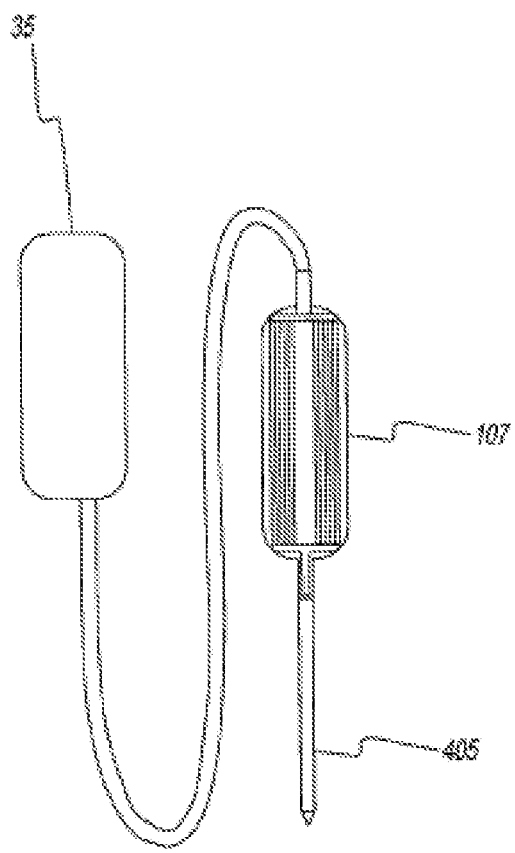
FIG. 18 illustrates a transfusion kit having an oxygenation device to oxygenate RBCs in advance of transfusion.

Referring to FIG. 18, immediately before RBCs are to be transfused, such RBCs can be placed in a further bag 35 in connected to a device 107 to add back oxygen prior to transfusion. Significantly, oxygen may be added back to RBCs after any gamma or x-ray irradiation or addition of nitric oxide to avoid the development of deleterious storage legions addressed above. Device 107 is like device OCDD, however, it does not have $O_2/CO_2$ sorbent material, but instead contains pure oxygen or air in the inner space containing hollow fibers. This use is for special cases, such as massive transfusions, where the capacity of the lung to re-oxygenate transfused blood may not be adequate, or sickle cell anemia. Once the oxygen is added back, transfusion using needle 405 can occur.

Figure 19:
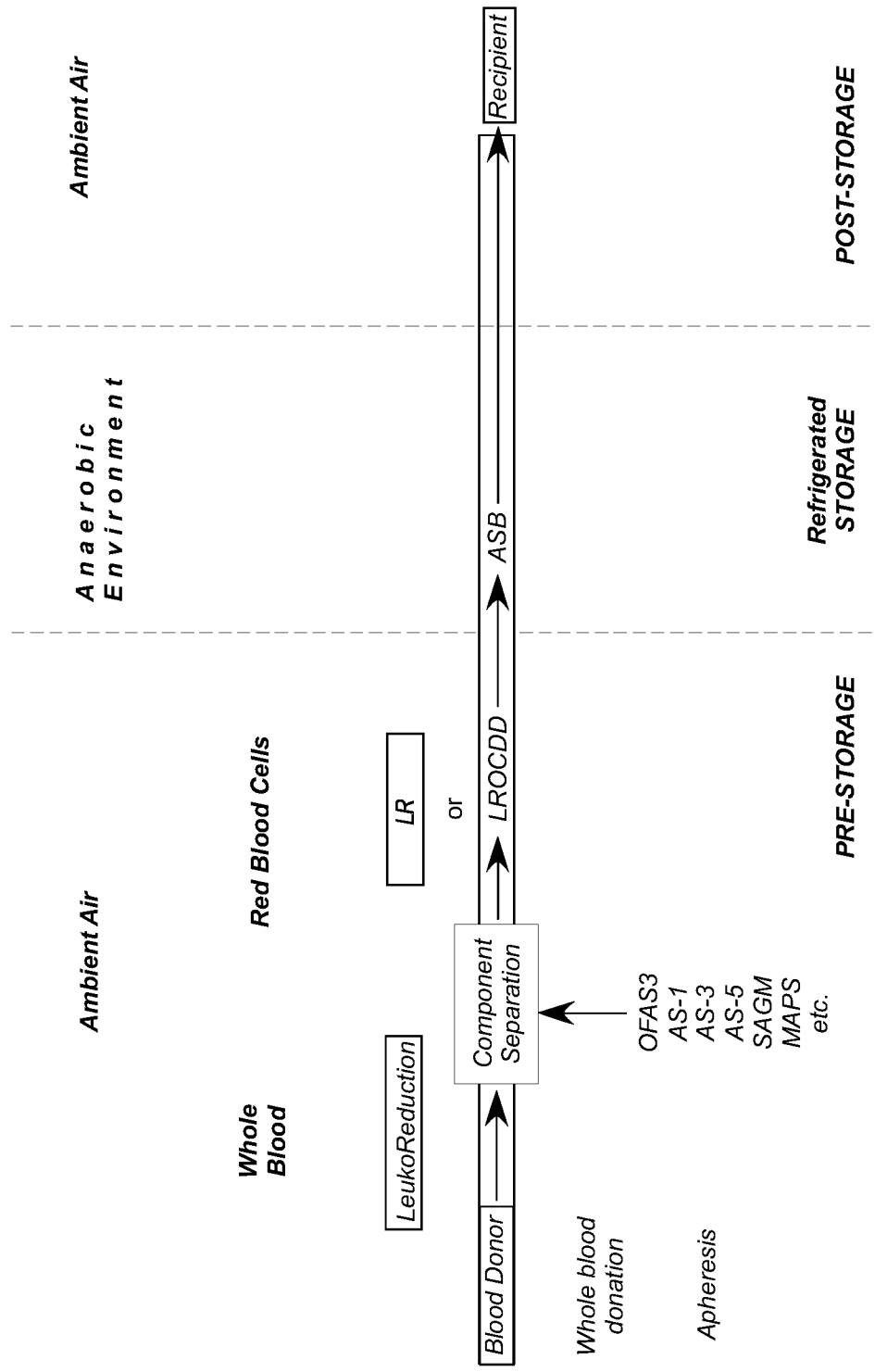
FIG. 19 illustrates an alternative configuration according to the present disclosure, including leukoreduction, oxygen, carbon dioxide or oxygen and/or carbon dioxide depletion.

Referring to FIG. 19, a possible configuration of FIG. 1 shows oxygen depletion of RBCs and leukoreduction of RBCs prior to storage an anaerobic storage bag. FIG. 19 shows whole blood that may be obtained from a donor or by apherisis, may be separated into components of plasma, platelets and RBCs. An additive solution may be added to RBCs that are either leukoreduced prior to oxygen, carbon dioxide or oxygen and carbon dioxide depletion or leukoreduced after oxygen, carbon dioxide or oxygen and carbon dioxide depletion.

Figure 20:
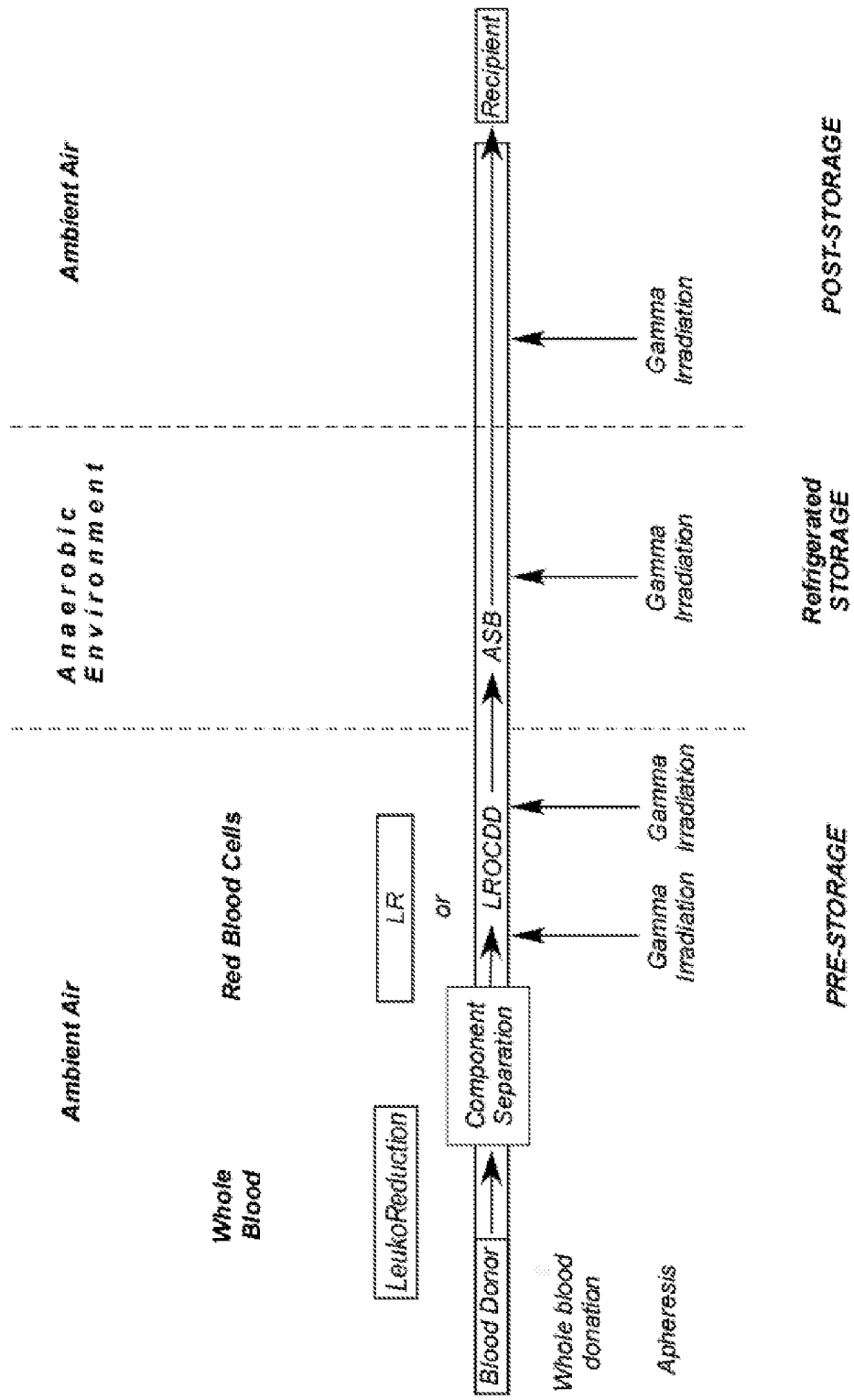
FIG. 20 illustrates an alternative configuration according to the present disclosure, including leukoreduction, oxygen, carbon dioxide or oxygen and/or carbon dioxide depletion and irradiation at different times during aerobic and anaerobic conditions of RBCs.

FIG. 20 illustrates a configuration of the flowchart of FIG. 1, including leukoreduction, oxygen, carbon dioxide or oxygen and/or carbon dioxide depletion. FIG. 20 illustrates the step of leukoreduction during the whole blood or after component separation at which time RBCs can be leukoreduced. Additionally, leukoreduction can be conducted using a combination leukoreduction device 1060 that is also an oxygen and carbon dioxide depletion device. Gamma irradiation or x-ray irradiation can occur at various times during Phase A, Phase B or Phase C. Gamma and x-ray irradiation can occur during anaerobic conditions after the removal of oxygen in OCDD device 100, during storage in anaerobic storage bag 200 or in post-storage phase before the addition of oxygen prior to transfusion. Irradiation is preferably performed in an anaerobic environment because an anaerobic environment minimizes oxidative damage by removing fuel of oxidative reactions. Alternatively, when gamma or x-ray irradiation occur before anaerobic conditions are present, RBCs must undergo oxygen depletion shortly thereafter and preferably within 24 hours.

Figure 21:
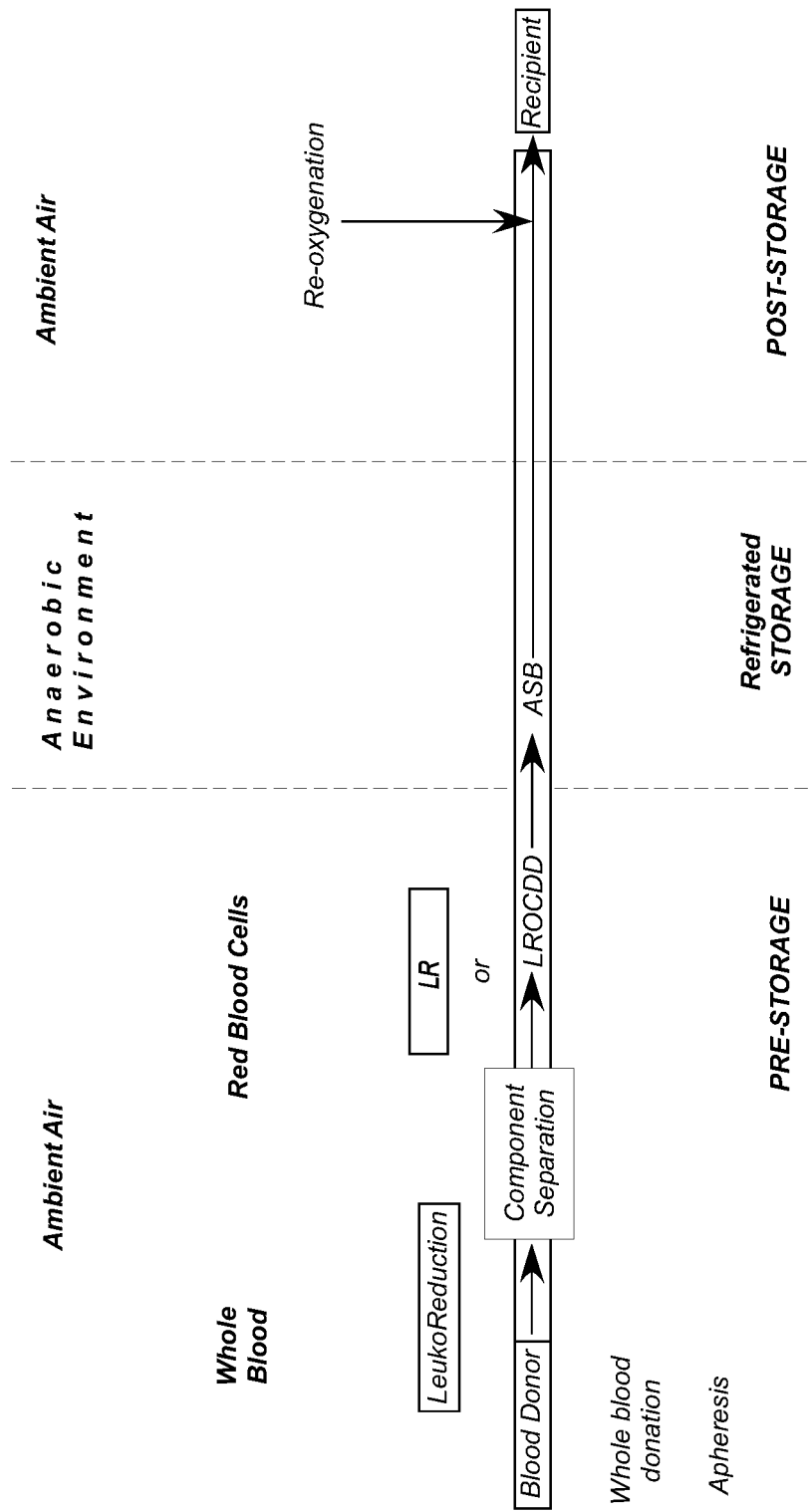
FIG. 21 illustrates an alternative configuration according to the present disclosure, including leukoreduction, oxygen, carbon dioxide or oxygen and/or carbon dioxide depletion and re-oxygenation immediately prior to transfusion to a recipient.

FIG. 21 illustrates a configuration of the flowchart of FIG. 1, including leukoreduction, oxygen, carbon dioxide or oxygen and/or carbon dioxide depletion and re-oxygenation immediately prior to transfusion to a recipient. Addition of oxygen immediately prior to transfusion is beneficial to recipient of RBCs. Oxygen addition is particularly beneficial to recipients of massive transfusions such as those who suffer from sickle cell disease.

Figure 22:
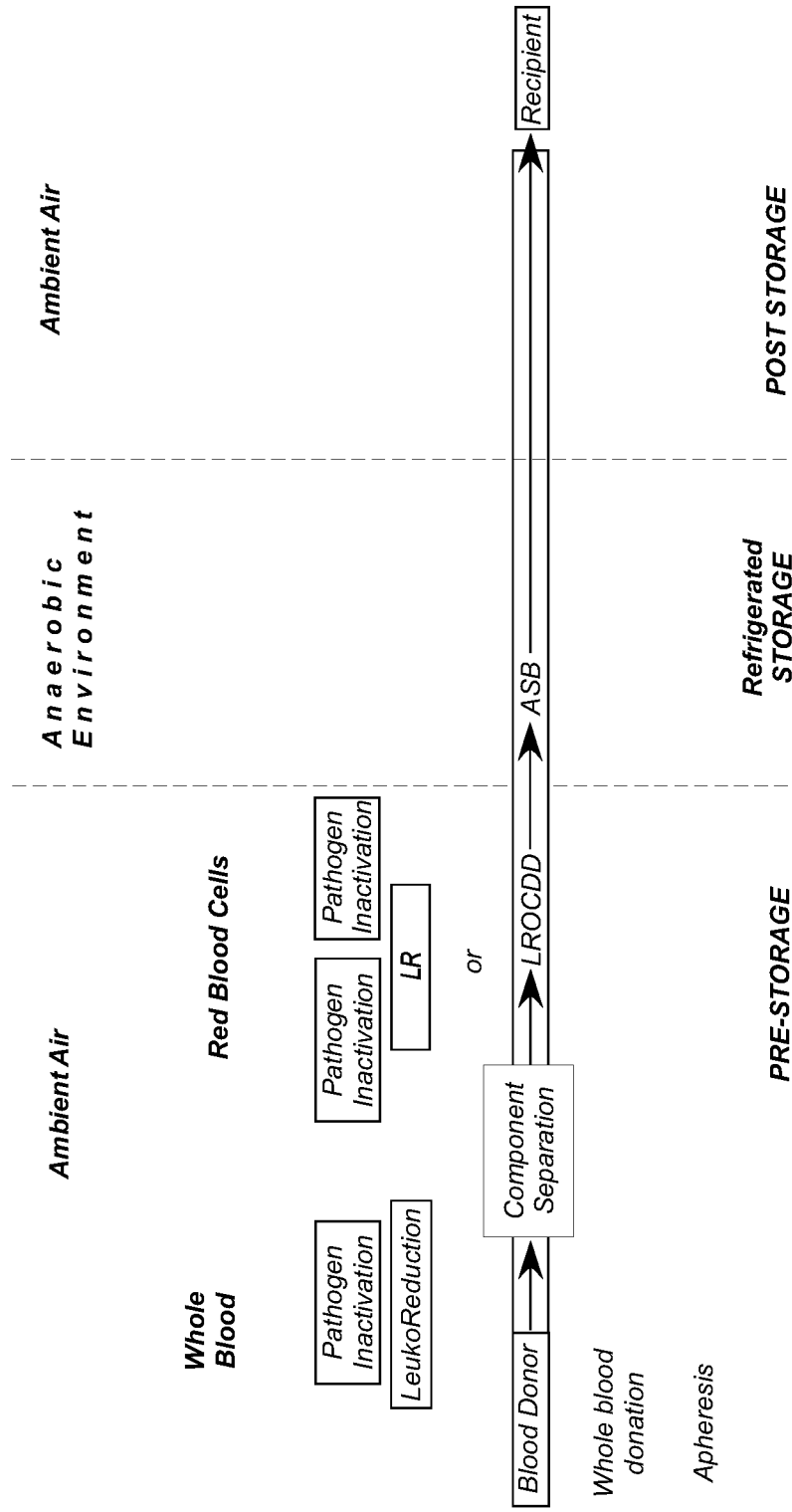
FIG. 22 illustrates an alternative configuration according to the present disclosure, including leukoreduction, oxygen, carbon dioxide or oxygen and/or carbon dioxide depletion, and pathogen inactivation at various possible times during collection and storage.

FIG. 22 illustrates a configuration of the flowchart of FIG. 1, including leukoreduction, oxygen, carbon dioxide or oxygen and/or carbon dioxide depletion, and pathogen inactivation at various possible times during collection and storage. Pathogen inactivation may harm RBCs by generating reactive oxygen species during the process. Anaerobic environments reduce ROS RBC damage during subsequent storage period.

Figure 23:
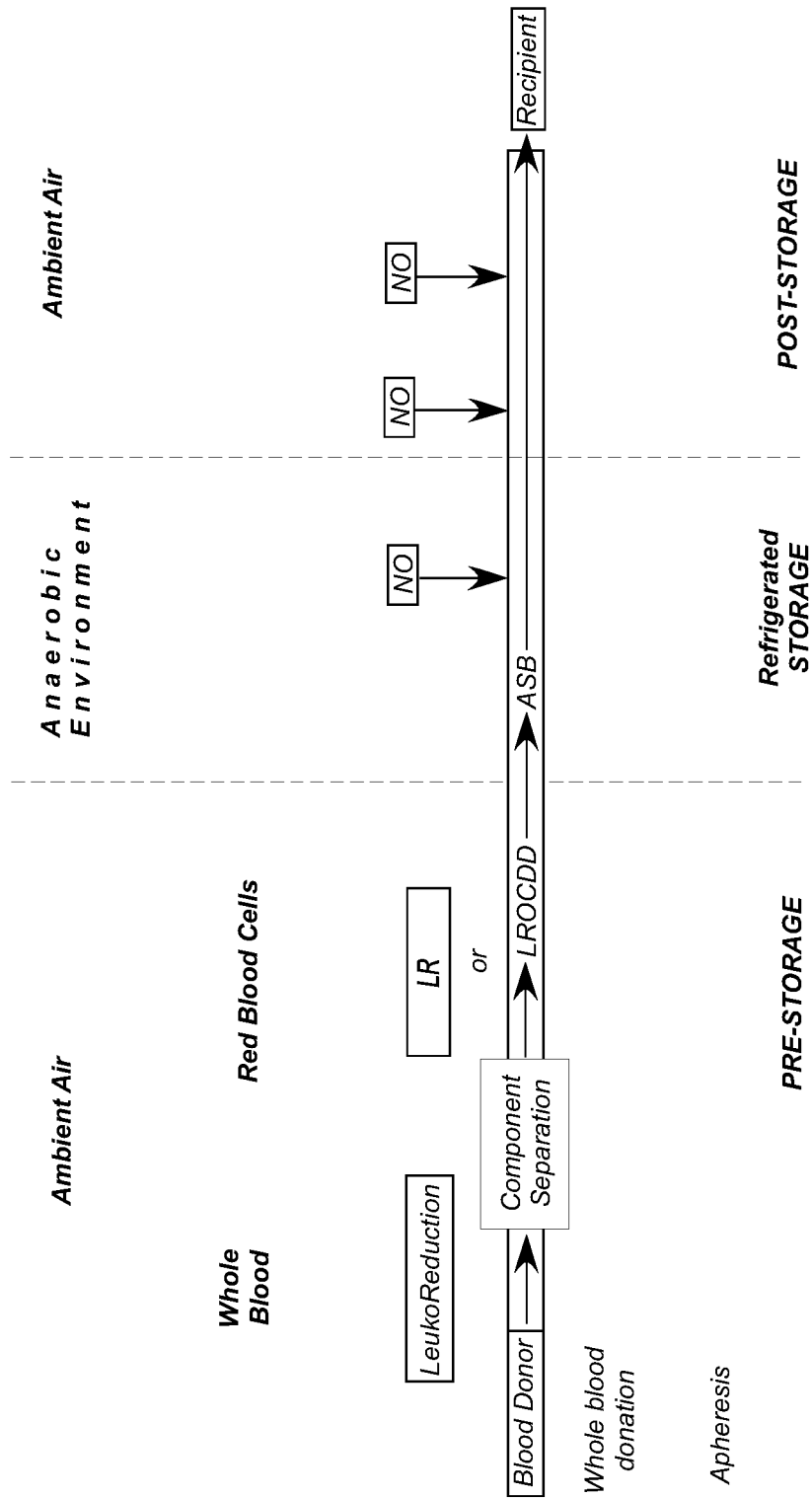
FIG. 23 illustrates an alternative configuration according to the present disclosure, including leukoreduction, oxygen, carbon dioxide or oxygen and/or carbon dioxide depletion, and nitric oxide addition at various possible times during storage.

FIG. 23 illustrates a configuration of flowchart of FIG. 1, including leukoreduction, oxygen, carbon dioxide or oxygen and/or carbon dioxide depletion, and nitric oxide addition at various possible times during storage. Nitric oxide can be added as NO-precursors, NO gas or nitrate to anaerobic RBCs. The nitric oxide and hemoglobin-NO compound are less labile under anaerobic conditions.

In each of FIGS. 19 through 23, other processes described in FIG. 1 and throughout present disclosure could also be provided to such figures.

Although the foregoing describes various embodiments by way of illustration and example, the skilled artisan will appreciate that various changes and modifications may be practiced within the spirit and scope of the present application.

What is claimed is:

1. A method of preparing red blood cells for transfusion in the treatment of an inherited hemoglobinopathy in a subject in need thereof comprising:
   obtaining whole blood;
   separating red blood cells from said whole blood to form packed red blood cells;
   depleting oxygen and carbon dioxide from said packed red blood cells prior to storage to prepare depleted packed red blood cells; and
   storing said depleted packed red blood cells in an anaerobic storage bag comprising an outer bag having a barrier film that is impermeable to oxygen and carbon dioxide, and an inner bag in contact with said red blood cells, wherein said depleted packed red blood cells are maintained in an anaerobic condition, to form stored depleted red blood cells.

2. The method of claim 1, further comprising oxygenating said stored depleted red blood cells.

3. The method of claim 1, further comprising transfusing said red blood cells into a subject in need thereof.

4. The method of claim 1, wherein said inherited hemoglobinopathy is thalassemia.

5. The method of claim 1, wherein said inherited hemoglobinopathy is alpha-thalassemia.

6. The method of claim 1, wherein said inherited hemoglobinopathy is beta-thalassemia.

7. The method of claim 1, wherein said stored depleted red blood cells comprise an initial oxygen saturation of less than 3 Torr.

8. The method of claim 1, wherein said subject in need thereof requires 30 or more units of blood per year.

9. The method of claim 1, wherein said stored depleted red blood cells have higher 24-hr recovery and reduced excess iron when transfused into said subject in need thereof, compared to red blood cells not oxygen depleted.

10. The method of claim 1, further comprising reducing iron overload in said subject in need thereof.

11. The method of claim 1, wherein said stored oxygen depleted red blood cells are stored for up to 42 days.

12. The method of claim 1, wherein said anaerobic storage bag further comprises a sorbent comprising an oxygen sorbent, a carbon dioxide sorbent, or a combination thereof, disposed between said inner bag and said outer bag.

13. The method of claim 1, further comprising adding an additive solution to said packed red blood cells to form a suspension of packed red blood cells.

14. The method of claim 13, wherein said additive solution comprises AS-1, AS-3, AS-5, SAGM, PAGG-SM, PAGG-GM, MAP, SOLX, ESOL, EAS61, OFAS1, OFAS3, or any combinations thereof.

15. The method of claim 1, wherein said anaerobic storage bag is irradiated by gamma or x-ray irradiation.

16. The method of claim 1, further comprising gamma or x-ray irradiating said depleted packed red blood cells before transfusion.

17. The method of claim 1, wherein said red blood cells reduce complications from chronic transfusion therapy in said subject in need thereof.

18. The method of claim 17, wherein said red blood cells have higher 24-hr recovery and reduced excess iron when transfused into said subject in need thereof, compared to red blood cells not oxygen depleted.

19. The method of claim 3, wherein said red blood cells reduce morbidity from chronic transfusion therapy in a subject in need thereof.

20. The method of claim 19, wherein said stored depleted red blood cells have higher 24-hr recovery and reduced excess iron when transfused into said subject in need thereof, compared to red blood cells not oxygen depleted.

* * * * *